United States Patent
Avkin-Nachum et al.

(10) Patent No.: US 10,059,942 B2
(45) Date of Patent: Aug. 28, 2018

(54) THERAPEUTIC OLIGONUCLEOTIDES COMPRISING PYRAZOLOTRIAZINE NUCLEOTIDE ANALOGUES

(71) Applicants: QBI ENTERPRISES LTD., Nes Ziona (IL); BIO-LAB LTD., Jerusalem (IL)

(72) Inventors: Sharon Avkin-Nachum, Nes Zionna (IL); Jean-Christophe Truffert, Saint-Prest (FR); Myriam Lefoix, Le Bardon (FR); Jean Hildesheim, Jerusalem (IL); Tirtsa Kleinman, Jerusalem (IL)

(73) Assignees: BIO-LAB LTD., Jerusalem (IL); QBI ENTERPRISES LTD., Nes Ziona (IL)

( * ) Notice: Subject to any disclaimer, the term of this patent is extended or adjusted under 35 U.S.C. 154(b) by 0 days.

(21) Appl. No.: 14/403,581

(22) PCT Filed: May 30, 2013

(86) PCT No.: PCT/IL2013/050465
§ 371 (c)(1),
(2) Date: Nov. 25, 2014

(87) PCT Pub. No.: WO2013/179292
PCT Pub. Date: Dec. 5, 2013

(65) Prior Publication Data
US 2015/0166990 A1    Jun. 18, 2015

Related U.S. Application Data

(60) Provisional application No. 61/653,432, filed on May 31, 2012.

(51) Int. Cl.
*C12N 15/113* (2010.01)
*A61K 31/7115* (2006.01)

(52) U.S. Cl.
CPC ........ *C12N 15/113* (2013.01); *A61K 31/7115* (2013.01); *C12N 2310/14* (2013.01); *C12N 2310/314* (2013.01); *C12N 2310/321* (2013.01); *C12N 2310/333* (2013.01); *C12N 2310/336* (2013.01); *C12N 2310/344* (2013.01); *C12N 2320/51* (2013.01); *C12N 2320/53* (2013.01); *C12N 2330/30* (2013.01)

(58) Field of Classification Search
CPC ........................ C12N 15/113; A61K 31/7115
See application file for complete search history.

(56) References Cited

U.S. PATENT DOCUMENTS

| 5,652,099 A | 7/1997 | Conrad |
| 6,268,132 B1 * | 7/2001 | Conrad .................. C07H 19/04 |
| | | 435/6.16 |

FOREIGN PATENT DOCUMENTS

| WO | WO 2004/042029 | 5/2004 |
| WO | WO 2010/011895 | 1/2010 |

OTHER PUBLICATIONS

Stambasky et al (Chem. Rev. (2009), 109, pp. 6729-6764).*
Frank Seela et al: "Pyrazolo[3,4-d] [1,2,3]triazine DNA: Synthesis and Base Pairing of 7-Deaza-2,8-diaza-2'-deoxyadenosine", The Journal of Organic Chemistry, vol. 69, No. 14, Jun. 17, 2004 (Jun. 17, 2004) pp. 4695-4700.
Raboisson P et al: "A General Approach toward the Synthesis of C-Nucleoside Pyrazolo[1,5-a]-1,3,5-triazines and Their 3',5'-Bisphosphate C-Nucleotide Analogues as the First Reported in Vivo Stable P2Y1-Receptor Antagonists", The Journal of Organic Chemistry, American Chemical Society [Not]Etc.,vol. 67, Oct. 16, 2002 (Oct. 16, 2002), pp. 8063-8071.

* cited by examiner

Primary Examiner — J. E. Angell
(74) Attorney, Agent, or Firm — JMB Davis Ben-David

(57) ABSTRACT

Disclosed herein are double-stranded RNA nucleic acid molecules, which include at least one pyrazolotriazine nucleotide analog and have been modified to exhibit one of the following, increased on-target activity, increased target specificity, enhanced nuclease stability, reduced off target activity and/or reduced immunogenicity when compared to an unmodified or similarly modified dsRNA; pharmaceutical compositions comprising such molecules and methods of use thereof in therapy.

12 Claims, 12 Drawing Sheets
Specification includes a Sequence Listing.

EGFP_1_S500
Position 18 2'OMe A

EGFP_1_S1957
Position 18 unmodified rA

EGFP_1_S1913
Position 18 PT dA

EGFP_1_S2141
Position 18 PT rA

EGFP_1_S1913
Position 18 PT dA

Sense

EGFP_1_S1992
Position 18 dA

Sense

EGFP_1_S500

EGFP_1_S1911
Position 1 AS PT dA

EGFP_1_S1910
Position 1 AS PT dA, 5'Pi

In HCT116 extract

In Skov3 extract

SEQUENCE LISTING

```
<160> NUMBER OF SEQ ID NOS: 31

<210> SEQ ID NO 1
<211> LENGTH: 2341
<212> TYPE: RNA
<213> ORGANISM: Homo_sapiens

<400> SEQUENCE: 1
gggaggccgg augugagugg agcggccauu uccuguuucu cugcaguuuu ccucagcuuu      60 ggguggugge cgcugccggg caucggcuuc caguccgcgg agggcgaggc ggcguggaca     120
gcggccccgg cacccagcgc cccgccgccc gcaagccgcg cgcccguccg ccgcgccccg     180
agcccgccgc uuccuaucuc agcgcccugc cgccgccgcc gcggcccagc gagcggcccu     240
gaugcaggcc aucaagugug uggugguggg agacggagcu guagguaaaa cuugccuacu     300
gaucaguuac acaaccaaug cauuuccugg agaauauauc ccuacugucu uugacaauua     360
uucugccaau guuaugguag augggaaaacc ggugaaucug ggcuuauggg auacagcugg     420
acaagaagau uaugacagau uacgccccccu auccuauccg caaacagaug uguucuuaau     480
uugcuuuucc cuugugaguc cugcaucauu ugaaaaugue cgugcaaagu gguauccuga     540
ggugcggcac cacugucccca acacucccau cauccuagug ggaacuaaac uugaucuuag     600
ggaugauaaa gacacgaucg agaaacugaa ggagaagaag cugacucccca ucaccuaucc     660 gcagggucua gccauggcua aggagauugg ugcuguaaaa uaccuggagu gcucggcgcu     720
cacacagcga ggccucaaga caguguuuga cgaagcgauc cgagcaguccc ucugcccgcc     780 ucccgugaag aagaggaaga gaaaaugccu gcuguuguaa augucucagc cccucguucu     840 uggccuguc ccuuggaacc uuuguacgcu uugcucaaaa aaaaacaaaa aaaaaaaca     900 aaaaaaaaa acaacggugg agccuucgca cucaaugcca acuuuuuguu acagauuaau     960
uuuuccauaa aaccauuuuu ugaaccaauc aguaauuuua agguuuuguu uguucuaaau    1020
guaagaguuc agacucacau ucuauuaaaa uuuagcccua aaaugacaag ccuucuuaaa    1080
gccuuauuuu ucaaaagcgc cccccccauu cuuguucaga uuaagaguug ccaaaauacc    1140
uucugaacua cacugcauug uugugccgag aacaccgagc acugaacuuu gcaaagaccu    1200
ucgucuuuga gaagacggua gcuucugcag uuaggaggug cagacacuug cucuccuaug    1260
```

| | | |
|---|---|---|
| uaguucucag augcguaaag cagaacagcc ucccgaauga agcguugcca uugaacucac | 1320 | |
| cagugaguua gcagcacgug uucccgacau aacauuguac uguaauggag ugagcguagc | 1380 | |
| agcucagcuc uuuggaucag ucuuugugau uucauagcga guuucugac cagcuuuugc | 1440 | |
| ggagauuuug aacagaacug cuauuuccuc uaaugaagaa uucuguuuag cuguggugu | 1500 | |
| gccggguggg gugugugugu ucaaaggaca aagacaguau uuugacaaaa uacgaagugg | 1560 | |
| agauuuacac uacauuguac aaggaaugaa agugucacgg uaaaaacuc uaaaagguua | 1620 | |
| auuucuguca aaugcaguag augaugaaag aaagguuggu auuaucagga aauguuuucu | 1680 | |
| uaagcuuuuc cuuucucuua caccugccau gccuccccaa auugggcauu uaauucaucu | 1740 | |
| uuaaacuggu uguucuguua gucgcuaacu aguaagugc uuucuuaua gaaccccuuc | 1800 | |
| ugacugagca auaugccucc uuguauuaua aaaucuuucu gauaaugcau uagaagguuu | 1860 | |
| uuuugucgau uaguaaaagu gcuuccaug uuacuuuauu cagagcuaau aagugcuuuc | 1920 | |
| cuuaguuuuc uaguaacuag guguaaaaau caugcuguugc agcuuauag uuuuuaaaau | 1980 | |
| auuuuagaua auucuuaaac uaugaaccuu cuuaacauca cugucuugcc agauuaccga | 2040 | |
| cacugucacu ugaccaauac ugacccucuu uaccucgccc acgcggacac acgccuccug | 2100 | |
| uagucgcuuu gccuauugau guuccuuugg gucugugagg uucuguaaac ugugcuagug | 2160 | |
| cugacgaugu ucuguacaac uuaacucacu ggcgagaaua cagcguggga cccuucagcc | 2220 | |
| acuacaacag aauuuuuuaa auugacaguu gcagaauugu ggaguguuuu uacauugauc | 2280 | |
| uuuugcuaau gcauuagca uuauguuuug cauguaugac uuaauaaauc cuugaaucau | 2340 | |
| a | 2341 | |

<210> SEQ ID NO 2
<211> LENGTH: 720
<212> TYPE: RNA
<213> ORGANISM: Artificial
<220> FEATURE:
<223> OTHER INFORMATION: Chemically synthesized

<400> SEQUENCE: 2

| | | |
|---|---|---|
| auggugagca agggcgagga gcuguucacc gggguggugc ccauccuggu cgagcuggac | 60 | |
| ggcgacguaa acggccacaa guucagcgug uccggcgagg gcgagggcga ugccaccuac | 120 | |
| ggcaagcuga cccugaaguu caucugcacc accggcaagc ugcccgugcc cuggcccacc | 180 | |
| cucgugacca cccugaccua cggcgugcag ugcuucagcc gcuaccccga ccacaugaag | 240 | |
| cagcacgacu ucuucaaguc cgccaugccc gaaggcuacg uccaggagcg caccaucuuc | 300 | |
| uucaaggacg acggcaacua caagacccgc gccgagguga aguucgaggg cgacacccug | 360 | |
| gugaaccgca ucgagcugaa gggcaucgac uucaaggagg acggcaacau ccugggggcac | 420 | |
| aagcuggagu acaacuacaa cagccacaac gucuauauca uggccgacaa gcagaagaac | 480 | |
| ggcaucaagg ugaacuucaa gauccgccac aacaucgagg acggcagcgu gcagcucgcc | 540 | |
| gaccacuacc agcagaacac ccccaucggc gacggccccg ugcugcugcc cgacaaccac | 600 | |
| uaccugagca cccaguccgc ccugagcaaa gaccccaacg agaagcgcga ucacaugguc | 660 | |
| cugcuggagu ucgugaccgc cgccgggauc acucucggca uggacgagcu guacaaguaa | 720 | |

<210> SEQ ID NO 3
<211> LENGTH: 5436
<212> TYPE: RNA
<213> ORGANISM: Homo_sapiens

<400> SEQUENCE: 3

```
ggccgcggcg gcggaggcag cagcggcggc ggcaguggcg gcggcgaagg uggcggcggc      60
ucggccagua cucccggccc ccgccauuuc ggacugggga cgagcgcggc gcaggcacug     120
aaggcggcgg cggggccaga ggcucagcgg cucccaggug cgggagagag gccugcugaa     180
aaugacugaa uauaaacuug ugguaguugg agcuggugc uaggcaaga ugccuugac        240 gauacagcua auucagaauc auuuugugga cgaauaugau ccaacaauag aggauuccua     300
caggaagcaa uaguaauug augggagaaac cugucucuug auauucucg acacagcagg      360 ucaagaggag uacagugcaa ugagggacca guacaugagg acuggggagg gcuucuuug     420 uguauuugcc auaauaaua cuaaaucauu ugaagauauu caccauuaua gagaacaaau      480
uaaaagaguu aaggacucug aagaguacc uauggucca uaggaaaua aaugugauuu       540 gccuucuaga acaguagaca caaaacaggc ucaggacuua gcaagaaguu auggaauucc     600
uuuuauugaa acaucagcaa agacaagaca gagaguggag gaugcuuuuu auacauggu     660 gagggagauc cgacaauaca gauugaaaaa aaucagcaaa aagagaaaga cuccuggcug    720
ugugaaaauu aaaaaaugca uuauaaugua aucuggguguu ugaugaugcc uucuauacau    780
uaguucgaga aauucgaaaa cauaaagaaa agaugagcaa agaugguaaa aagaagaaaa    840
agaagucaaa gacaaagugu guaauuaugu aaauacaauu guacuuuuu ucuuaaggca     900 acuaguaca agugguaauu uuuguacauu acacuaaauu auuagcauuu guuuuagcau     960
uaccuaauuu uuuuccugcu ccaugcagac uguuagcuuu uaccuaaauu gcuuauuuua   1020
aaaugacagu ggaaguuuuuu uuuuccucua agugccagua uucccagagu uuuugguuuu  1080
gaacuagcaa ugccugugaa aaagaaacug aauaccuaag auuucugucu ugggguuuuuu  1140 ggugcaugca guugauuacu ucuuauuuuu cuuaccaauu gugaauguug gugugaaaca  1200
aauuaaugaa gcuuugaauu caucccuauu cuguguuuua ucuagucaca uaaauggauu  1260
aauuacuaau uucaguugag accuucuaau ugguuuuac ugaaacauug agggaacaca    1320 aauuuaugg cuuccugaug augauucuuc uaggcaucau guccuauagu uugucaucc    1380 ugaugaaugu aaaguuacac uguucacaaa gguuuugucu ccuuuccacu gcauuaguc    1440 auggucacuc uccccaaaau auuauauuuu uucuauaaaa agaaaaaaau ggaaaaaaau   1500
uacaaggcaa uggaaacuau uauaaggcca uuuccuuuuc acauuagaua aauuacuaua   1560
aagacuccua auagcuuuuc cuguuaaggc agacccagua ugaaugggg auuauuauag    1620 caaccauuuu ggggcuauau uuacaugcua cuaaauuuuu auaauaauug aaaagauuuu   1680
aacaaguaua aaaaauucuc auaggaauua aauguagucu cccuguguca gacugcucuu   1740
ucauaguaua acuuuaaauc uuuucuucaa cuugagucuu ugaagauagu uuuaauucug   1800
cuugugacau uaaaagauua uuugggccag uuauagcuua uuagguguug aagagaccaa   1860
gguugcaagg ccaggcccug ugugaaccuu ugagcuuuca uagagaguuu cacagcaugg  1920 acugugucc cacggucauc caguuuguc augcauuggu uaucaaaau ggggagggac     1980 uagggcaguu uggauagcuc aacaagauac aaucucacuc uguggguguuc cugcugacaa  2040 aucaagagca uugcuuuugu uucuuaagaa aacaaacucu uuuuuaaaaa uuacuuuuaa  2100
auauuaacuc aaaaguugag auuuggggu ggugugugc caagcauua auuuuuuuuu      2160 uaaacaauga aguaaaaag uuuuacaauc ucagguuug gcuaguucuc uuaacacugg    2220
uuaaauuaac auugcauaaa cacuuuucaa gucugaucca uauuuaauaa ugcuuuaaaa  2280
uaaaaauaaa aacaauccuu uugauaaauu uaaaauguua cuuauuuuaa aauaaaugaa  2340
```

```
gugagauggc auggugaggu gaaaguauca cuggacuagg aagaagguga cuuagguucu    2400
agauaggugu cuuuuaggac ucugauuuug aggacaucac uuacuaucca uucuucaug    2460
uuaaaagaag ucaucucaaa cucuuaguuu uuuuuuuua caacuaugua auuuauauuc    2520
cauuuacaua aggauacacu uauuugucaa gcucagcaca aucguaaau uuuuaaccua    2580
uguuacacca ucuucagugc cagucuuggg caaaauugug caagaggugu aguuuauauu    2640
ugaauaucca uucucguuuu aggacucuuc uuccauauua gugucaucuu gccucccuac    2700
cuuccacaug ccccaugacu ugaugcaguu uuaauacuug uaauucccu aaccauaaga    2760
uuuacugcug cuguggauau uccaugaag uuucccacu gagucacauc agaaaugccc    2820
uacaucuuau uccucaggg cucaagagaa ucgacagau accauaaagg gauuugaccu    2880
aaucacuaau uucaggugg uggcugaugc uuugaacauc ucuugcugc ccaauccauu    2940
agcgacagua ggauuuuuca aaccugguau gaauagacag aacccuaucc aguggaagga    3000
gaauuuaaua aagauagcgc ugaagaauu ccuuagguaa ucuauaacua ggacuacucc    3060
ugguaacagu aauacauucc auuguuuag uaaccagaaa ucuucaugca augaaaaaua    3120
cuuuaauuca ugaagcuuac uuuuuuuuuu uggugucaga gucucgcucu ugucacccag    3180
gcuggaaugc aguggcgcca ucucagcuca cugcaaccuc caucucccag guucaagcga    3240
uucucgugcc ucggccuccu gaguagcugg gauuacaggc gugugccacu acaucaacu    3300
aauuuuugua uuuuuaggag agacggggu ucacccuguu ggccaggcug gucucgaacu    3360
ccugaccuca agugauucac ccaccuuggc ucuaaaaccc uguuuugcag aacucauuua    3420
uucagcaaau auuauugag ugccuaccag augccaguca ccgcacaagg cacuggguau    3480
augguauccc caaacaagag acauaauccc gguccuuagg uagugcuagu guggucugua    3540
auaucuuacu aaggccuuug guaucgacc cagagauaac acgaugcgua uuuuaguuuu    3600
gcaaagaagg gguuuggucu cugugccagc ucuauaauug uuuugcuacg auuccacuga    3660
aacucuucga ucaagcuacu uuauguaaau cacuucauug uuuuaaagga auaaacuuga    3720
uuauauuguu uuuuuauuug gcauaacugu gauucuuuua ggacaauuac uguacacauu    3780
aagguguaug ucagauauuc auauugaccc aaauguguaa uauuccaguu uucucugcau    3840
aaguaauuaa aauauacuua aaauuaaua guuuuaucug gguacaaaua aacaggugcc    3900
ugaacuaguu cacagacaag gaaacuucua uguaaaauc acuaugauuu cugaauugcu    3960
augugaaacu acagaucuuu ggaacacugu uuagguaggg uguuaagacu acacaguac    4020
cucguuucua cacagagaaa gaaauggcca acuucagga acugcagugc uuaugagggg    4080
auauuuaggc cucuugaauu uuugaugua augggcauuu uuuuaaggua gugguuaauu    4140
accuuuaugu gaacuuugaa ugguuuaaca aagauuugu uuuuguagag auuuuaaagg    4200
gggagaauuc uagaaauaaa uguuaccaa uuauuacagc cuuaaagaca aaauccuug    4260
uugaaguuuu uuuaaaaaa gcuaaauuac auagacuuag gcauuaacau guuuguggaa    4320
gaauauagca gacguauauu guaucauuug agugaauguu cccaaguagg cauucuaggc    4380
ucuauuuaac ugagucacac ugcauaggaa uuagaaccu aacuuuuaua gguuaucaaa    4440
acuguuguca ccauugcaca auuuugccu aauauauaca uagaaacuuu gggggcaug    4500
uuaaguuaca guuugcacaa guucaucuca uuuguauucc auugauuuuu uuuucuucu    4560
aaacauuuuu ucuucaaaca guauauaacu uuuuuaggg gauuuuuuuu uagacagcaa    4620
aaacuaucug aagauuccca uuugucaaaa aguaaugauu ucuugauaau uguguaguaa    4680
uguuuuuuag aacccagcag uuaccuaaaa gcugaauuua uauuuaguaa cuucugugu    4740
```

| | | | | |
|---|---|---|---|---|
| aauacuggau | agcaugaauu | cugcauugag | aaacugaaua | gcugucauaa | aaugaaacuu | 4800 |
| ucuuucuaaa | gaaagauacu | cacaugaguu | cuugaagaau | agucauaacu | agauuaagau | 4860 |
| cuguguuuua | guuuaauagu | uugaagugcc | uguuugggau | aaugauaggu | aauuuagaug | 4920 |
| aauuuagggg | aaaaaaaagu | uaucugcaga | uauguugagg | gcccaucucu | cccccacac | 4980 |
| ccccacagag | cuaacugggu | uacaguguuu | uauccgaaag | uuccaauuc | cacugucuug | 5040 |
| uguuuucaug | uugaaaauac | uuuugcauuu | uccuuugag | ugccaauuuc | uuacuaguac | 5100 |
| uauucuuaa | uguaacaugu | uuaccuggaa | uguauuuaa | cuauuuugu | auaguguaaa | 5160 |
| cugaaacaug | cacauuuugu | acauugcu | uucuuugu | ggacauagc | agugugaucc | 5220 |
| aguuguuuuc | caucauuugg | uugcgcugac | cuaggaaugu | uggucauauc | aaacauuaaa | 5280 |
| aaugaccacu | cuuuuaauug | aaauuaacuu | uuaaaguguu | uauaggaguau | ugcugugaa | 5340 |
| gugaucuaaa | auuuguaaua | uuuuugucau | gaacuguacu | acuccuaauu | auuguaaugu | 5400 |
| aauaaaaaua | guuacaguga | caaaaaaaaa | aaaaaa | | | 5436 |

<210> SEQ ID NO 4
<211> LENGTH: 5312
<212> TYPE: RNA
<213> ORGANISM: Homo_sapiens

<400> SEQUENCE: 4

| | | | | | | |
|---|---|---|---|---|---|---|
| ggccgcggcg | gcggaggcag | cagcggcggc | ggcaguggcg | gcggcgaagg | uggcggcggc | 60 |
| ucggccagua | cucccggccc | ccgccauuuc | ggacugggag | cgagcgcggc | gcaggcacug | 120 |
| aaggcggcgg | cggggccaga | ggcucagcgg | cucccaggug | cgggagagag | gccugcugaa | 180 |
| aaugacugaa | uauaaacuug | ugguaguugg | agcgguggc | guaggcaaga | gugccuugac | 240 |
| gauacagcua | auucagaauc | auuuugugga | cgaauaugau | ccaacaauag | aggauuccua | 300 |
| caggaagcaa | guaguaauug | auggagaaac | cugucucuug | gauauucucg | acacagcagg | 360 |
| ucaagaggag | uacagugcaa | ugagggacca | guacaugagg | acuggggagg | gcuuucuuug | 420 |
| uguauuugcc | auaauaauaa | cuaaaucauu | ugaagauauu | caccauuaua | gagaacaaau | 480 |
| uaaaagaguu | aaggacucug | aagauguacc | uauggucoua | guaggaaaua | aaugugauuu | 540 |
| gccuucuaga | acaguagaca | caaaacaggc | ucaggacuua | gcaagaaguu | auggaauucc | 600 |
| uuuuauugaa | acaucagcaa | agacaagaca | gggugugaa | gaugccuucu | auacauuagu | 660 |
| ucgagaaauu | cgaaaacaua | agaaaagau | gagcaaagau | gguaaaaaga | agaaaaagaa | 720 |
| gucaaagaca | aagugugaa | uuaguguaaa | uacaauugua | cuuuuucuu | aaggcauacu | 780 |
| aguacaagug | guaauuuuug | uacauuacac | uaaauuauua | gcauugguu | uagcauuacc | 840 |
| uaauuuuuu | ccugcuccau | gcagacuguu | agcuuuacc | uuaaaugcuu | auuuaaaau | 900 |
| gacaguggaa | guuuuuuuu | ccucuaagug | ccaguauuc | cagaguuuug | guuuugaac | 960 |
| uagcaaugcc | ugugaaaaag | aaacugaaua | ccuaagauuu | cugucuuggg | guuuuuggug | 1020 |
| caugcaguug | auuacuucuu | auuuucuua | ccaauguga | auguggugu | gaaacaaauu | 1080 |
| aaugaagcuu | uugaaucauc | ccuauucugu | guuuaucua | gucacauaaa | uggauuaauu | 1140 |
| acuaauuuca | guugagaccu | ucuaauuggu | uuuuacugaa | acauugaggg | aacacaaauu | 1200 |
| uaugggcuuc | cugaugauga | uucuucuagg | caucaugucc | uauaguuugu | caucccugau | 1260 |
| gaauguaaag | uuacacuguu | cacaaaggu | ugucuccuu | uccacugcua | uuagucaugg | 1320 |
| ucacucuccc | caaaauauua | uauuuuucu | auaaaaagaa | aaaauggaa | aaaauuaca | 1380 |

-continued

```
aggcaaugga aacuauuaua aggccauuuc cuuuucacau uagauaaauu acuauaaaga      1440
cuccuaauag cuuuuccugu uaaggcagac ccaguaugaa augggggauua uuauagcaac     1500 cauuuugggg cuauauuuac augcuacuaa auuuuuauaa uaauugaaaa gauuuuaaca     1560
aguauaaaaa auucucauag gaauuaaaug uagucucccu ugucagacu gcucuuucau      1620 aguauaacuu uaaaucuuuu cuucaacuug agucuuugaa gauaguuuua auucugcuug     1680
ugacauuaaa agauuauuug ggccaguauau agcuuauuag guguugaaga gaccaagguu    1740
gcaaggccag gcccugugug aaccuuugag cuuucauaga gaguuucaca gcauggacug     1800 ugucccacg gucauccagu guugucaugc auugguuagu caaaaugggg agggacuagg      1860
gcaguuugga uagcucaaca agauacaauc ucacucugug guggccugc ugacaaauca      1920 agagcauugc uuuuguuucu uaagaaaaca aacucuuuuu uaaaaauuac uuuuaaauau     1980
uaacucaaaa guugagauuu uggggugug gugugccaag acauuaauuu uuuuuuaaa      2040 caaugaagug aaaaaguuuu acaaucucua gguuuggcua guucucuuaa cacugguuaa    2100
auuaacauug cauaaacacu uuucaagucu gauccauauu uaauaaugcu uuaaaauaaa    2160
aauaaaaaca auccuuuuga uaaauuuaaa auguuacuua uuuuaaauua aaugaaguga   2220
gauggcaugg ugaggugaaa guaucacugg acuaggaaga aggugacuua gguucuagau   2280
aggugucuuu uaggacucug auuuugagga caucacuuac uauccauuuc uucauguuaa    2340
aagaagucau cucaaacucu uaguuuuuu uuuuuacaac uauguaauuu auauuccauu     2400
uacauaagga uacacuuauu ugucaagcuc agcacaaucu guaaauuuuu aaccuauguu    2460
acaccaucuu cagugccagu cuugggcaaa auugugcaag aggugaaguu uauauuugaa   2520
uauccauucu cguuuuagga cucuucuucc auauuagugu caucuugccu cccuaccuuc    2580
cacaugcccc augacuugau gcaguuuuaa uacuuguaau uccccuaacc auaagauuua    2640
cugcugcugu ggauaucucc augaaguuuu cccacugagu cacaucagaa augcccuaca    2700
ucuuauuucc ucagggcuca agagaaucug acagauacca uaaagggauu ugaccuaauc    2760 acuauuuuc agguggugg cugaugcuuug aacaucucuu ugcugcccaa uccauuagcg     2820
acaguaggau uuuucaaacc ugguaugaau agacagaacc cuauccagug gaaggagaau    2880
uuaauaaaga uagugcugaa agaauuccuu agguaaucua uaacuaggac uacuccuggu    2940
aacaguaaua cauuccauug uuuuaguaac cagaaaucuu caugcaauga aaaauacuuu    3000
aauucaugaa gcuuacuuuu uuuuuuggu gucagagucu cgcucuuguc acccaggcug    3060
gaaugcagug gcgccaucuc agcucacugc aaccuccauc ucccagguuc aagcgauucu    3120
cgugccucgg ccuccugagu agcugggauu acaggcgugu gccacuacac ucaacuaauu    3180
uuuguauuuu uaggagagac gggguuucac ccuguuggcc aggcuggucu cgaacuccug    3240
accucaagug auucacccac cuuggccuca uaaaccuguu uugcagaacu cauuuauuca    3300
gcaaauauuu auugagugcc uaccagaugc cagucaccgc acaaggcacu ggguauaugg    3360
uauccccaaa caagagacau aaucccgguc cuuaggcuagu gcuaguguggg ucuguaauau  3420 cuuacuaagg ccuuugguau acgacccaga gauaacacga ugcguauuuu aguuuugcaa    3480
agaagggguu uggucucugu gccagcucua uaauuguuuu gcuacgauuc cacugaaacu    3540
cuucgaucaa gcuacuuuau guaaaucacu ucauuguuuu aaaggaauaa acuugauuau   3600
auuguuuuuu uauuuggcau aacugugauu cuuuuaggac aauuacugua cacauuaagg    3660
uguaugucag auauucauau ugacccaaau guguaauauu ccaguuuucu cugcauaagu    3720
aauuaaaaua uacuuaaaaa uuaauaguuu uaucggguua caaauaaaca ggugccugaa    3780
```

| | |
|---|---|
| cuaguucaca gacaaggaaa cuucuaugua aaaucacua ugauuucuga auugcuaugu | 3840 |
| gaaacuacag aucuuuggaa cacuguuuag guagggguguu aagacuuaca caguaccucg | 3900 |
| uuucuacaca gagaaagaaa uggccauacu ucaggaacug cagugcuuau gaggggauau | 3960 |
| uuaggccucu ugaauuuuug auguagaugg gcauuuuuu aagguagugg uuaauuaccu | 4020 |
| uuaugugaac uuugaauggu uuaacaaaag auuuguuuu guagagauuu uaaaggggga | 4080 |
| gaauucuaga aauaaauguu accaauuau uacagccuua aagacaaaaa uccuuguuga | 4140 |
| aguuuuuuua aaaaagcua aauuacauag acuuaggcau uaacauguuu guggaagaau | 4200 |
| auagcagacg uauauuguau cauuugagug aauguuccca aguaggcauu cuaggcucua | 4260 |
| uuuaacugag ucacacugca uaggaauuua gaaccuaacu uuuauagguu aucaaaacug | 4320 |
| uugucaccau ugcacaauuu uguccuaaua uauacauaga aacuuugugg ggcauguuaa | 4380 |
| guuacaguuu gcacaaguuc aucucauuug uauuccauug auuuuuuuu ucuucuaaac | 4440 |
| auuuuucuu caaacaguau auaacuuuuu uaagggauu uuuuuaga cagcaaaaac | 4500 |
| uaucugaaga uuuccauuug ucaaaaguaa augauuucuu gauaauugug uaguaauguu | 4560 |
| uuuuagaacc cagcaguuac cuuaaagcug aauuuauauu uaguaacuuc uguguuaaua | 4620 |
| cuggauagca ugaauucugc auugagaaac ugaauagcug ucauaaaaug aaacuuucuu | 4680 |
| ucuaaagaaa gauacucaca ugaguucuug aagaauaguc auaacuagau uaagaucugu | 4740 |
| guuuuaguuu aauaguuuga agugccuguu ugggauaaug auagguaauu uagaugaauu | 4800 |
| uaggggaaaa aaaaguuauc ugcagauaug uugagggccc aucucuccc ccacaccccc | 4860 |
| acagagcuaa cugggguuaca guguuuuauc cgaaaguuuc caauuccacu gucuugaguu | 4920 |
| uucauguuga aaauacuuuu gcauuuuucc uuugagugcc aauuucuuac uaguacuauu | 4980 |
| ucuuaaugua acauguuuac cuggaaugua uuuuaacuau uuuuguauag uguaaacuga | 5040 |
| aacaugcaca uuuugacau ugugcuucu uuugugggac auaugcagug ugauccaguu | 5100 |
| guuuuccauc auuuggguugc gcugaccuag gaaugugugu cauaucaaac auuaaaaaug | 5160 |
| accacucuuu uaauugaaau uaacuuuuaa auguuuauag gaguaugugc ugugaaguga | 5220 |
| ucuaaaauuu guauauuuu ugucaugaac uguacuacuc cuaauuauug uaauguaaua | 5280 |
| aaaauaguua cagugacaaa aaaaaaaaaa aa | 5312 |

<210> SEQ ID NO 5
<211> LENGTH: 2204
<212> TYPE: RNA
<213> ORGANISM: Homo_sapiens

<400> SEQUENCE: 5

| | |
|---|---|
| gagcggugcg gaggcucugc ucggaucgag gucugcagcg cagcuucggg agcaugagug | 60 |
| cugcagugac ugcagggaag cuggcacggg caccggccga cccugggaaa gccggggucc | 120 |
| ccggaguugc agcucccgga gcucggcgg cggcuccacc ggcgaaagag aucccggagg | 180 |
| uccuagugga cccacgcagc cggcggcgcu augugcgggg ccgcuuuuug ggcaagggcg | 240 |
| gcuuugccaa gugcuucgag aucucggacg cggacaccaa ggaguguuc gcgggcaaga | 300 |
| uugugccuaa gucucugcug cucaagccgc accagaggga gaagaugucc auggaaauau | 360 |
| ccauucaccg cagccucgcc caccagcacg ucguaggauu ccacggcuuu uucgaggaca | 420 |
| acgacuucgu guucguggug uuggagcucu gccgccggag gucucuccug gagcugcaca | 480 |
| agaggaggaa agcccugacu gagccugagg cccgauacua ccuacggcaa auugugcuug | 540 |

```
gcugccagua ccugcaccga aaccgaguua uucaucgaga ccucaagcug ggcaaccuuu    600
uccugaauga agaucuggag gugaaaauag gggauuuugg acuggcaacc aaagucgaau    660
augacgggga gaggaagaag acccugugug ggacuccuaa uuacauagcu cccgaggugc    720
ugagcaagaa agggcacagu ucgaggugg augugggguc cauugggugu aucauguaua     780
ccuuguuagu gggcaaacca ccuuuugaga cuucuugccu aaaagagacc uaccuccgga    840
ucaagaagaa ugaauacagu auucccaagc acaucaaccc cguggccgcc ucccucaucc    900
agaagaugcu ucagacagau cccacugccc gcccaaccau aacgagcug cuuaaugacg     960 aguucuuuac uucuggcuau aucccugccc gucccccau caccugccug accauuccac    1020
caagguuuuc gauugcuccc agcagccugg accccagcaa ccggaagccc cucacaguccc  1080 ucaauaaagg cuuggagaac ccccugccug agcgucccg ggaaaaagaa gaaccagugg    1140
uucgagagac aggugaggug gucgacugcc acccagaga caugcugcag cagcugcaca    1200
gugucaaugc cuccaagccc ucggagcgug ggcuggucag gcaagaggag gcugaggauc    1260
cugccugcau ccccaucuuc uggucagca aguggggga cuauucgac aaguacggcc      1320 uuggguauca gcucugugau aacagcgugg gggugcucuu caagacuca acacgccuca    1380 uccucuacaa ugauggugac agccugcagu acauagagcg ugacggcacu gaguccuacc   1440
ucaccgugag uccccaucccc aacuccuuga ugaagaagau cacccuccuu aaauauuucc  1500
gcaauuacau gagcgagcac uugcugaagg caggugccaa caucacgccg cgcgaaggug   1560
augagcucgc ccggcugccc uaccuacgga ccugguccg caccccgcagc gccaucaucc   1620 ugcaccucag caacggcagc gugcagauca acuucuucca ggaucacacc aagcucaucu   1680
ugugcccacu gauggcagcc gugaccuaca ucgacgagaa gcgggacuuc cgcacauacc   1740 gccuagucu ccuggaggag uacggcugcu gcaaggagcu ggccagccgg uccgcuacg     1800 cccgcacuau gguggacaag cugcugagcu cacgcucggc cagcaaccgu cucaaggccu   1860
ccuaauagcu gcccucccccu ccggacuggu gccuccuca cucccaccug caucgggggc   1920
ccauacuggu uggcucccgc ggugccaugu cugcagugug ccccccagcc ccgguggcug   1980
ggcagagcug caucauccuu gcagguggg guugcugugu aaguuauuuu uguacauguu    2040
cggguguggg uucuacagcc uugucccccu ccccccucaac cccaccauau gaauuguaca   2100
gaauauuucu auugaauucg gaacugtccu uccuuggcu uuaugcacau uaaacagaug    2160
ugaauauuca aaaaaaaaa aaaaaaaaaa aaaaaaaaa aaaa                      2204
```

<210> SEQ ID NO 6
<211> LENGTH: 19
<212> TYPE: RNA
<213> ORGANISM: Artificial
<220> FEATURE:
<223> OTHER INFORMATION: Chemically synthesized

<400> SEQUENCE: 6
cgugcaaagu gguauccug                                                  19

<210> SEQ ID NO 7
<211> LENGTH: 19
<212> TYPE: RNA
<213> ORGANISM: Artificial
<220> FEATURE:
<223> OTHER INFORMATION: Chemically synthesized

<400> SEQUENCE: 7
caggauacca cuuugcacg                                                  19

```
<210> SEQ ID NO 8
<211> LENGTH: 19
<212> TYPE: RNA
<213> ORGANISM: Artificial
<220> FEATURE:
<223> OTHER INFORMATION: Chemically synthesized

<400> SEQUENCE: 8
gccacaacgu cuauaucau                                                    19

<210> SEQ ID NO 9
<211> LENGTH: 19
<212> TYPE: RNA
<213> ORGANISM: Artificial
<220> FEATURE:
<223> OTHER INFORMATION: Chemically synthesized

<400> SEQUENCE: 9
augauauaga cguuguggc                                                    19

<210> SEQ ID NO 10
<211> LENGTH: 19
<212> TYPE: RNA
<213> ORGANISM: Artificial
<220> FEATURE:
<223> OTHER INFORMATION: Chemically synthesized

<400> SEQUENCE: 10
gcaucgagcu gaagggcau                                                    19

<210> SEQ ID NO 11
<211> LENGTH: 19
<212> TYPE: RNA
<213> ORGANISM: Artificial
<220> FEATURE:
<223> OTHER INFORMATION: Chemically synthesized

<400> SEQUENCE: 11
augcccuuca gcucgaugc                                                    19

<210> SEQ ID NO 12
<211> LENGTH: 19
<212> TYPE: RNA
<213> ORGANISM: Artificial
<220> FEATURE:
<223> OTHER INFORMATION: Chemically synthesized

<400> SEQUENCE: 12
guaaggcaga cccaguaua                                                    19

<210> SEQ ID NO 13
<211> LENGTH: 19
<212> TYPE: RNA
<213> ORGANISM: Artificial
<220> FEATURE:
<223> OTHER INFORMATION: Chemically synthesized

<400> SEQUENCE: 13
uauacugggu cugccuuac                                                    19

<210> SEQ ID NO 14
<211> LENGTH: 19
<212> TYPE: RNA
<213> ORGANISM: Artificial
<220> FEATURE:
```

<223> OTHER INFORMATION: Chemically synthesized

<400> SEQUENCE: 14
agaagaugcu ucagacagu                                               19

<210> SEQ ID NO 15
<211> LENGTH: 19
<212> TYPE: RNA
<213> ORGANISM: Artificial
<220> FEATURE:
<223> OTHER INFORMATION: Chemically synthesized

<400> SEQUENCE: 15
acugucugaa gcaucuucu                                               19

<210> SEQ ID NO 16
<211> LENGTH: 26
<212> TYPE: DNA
<213> ORGANISM: Artificial
<220> FEATURE:
<223> OTHER INFORMATION: Chemically Synthesized

<400> SEQUENCE: 16
tcgagcgtgc aaagtggtat cctggc                                       26

<210> SEQ ID NO 17
<211> LENGTH: 26
<212> TYPE: DNA
<213> ORGANISM: Artificial
<220> FEATURE:
<223> OTHER INFORMATION: Chemically Synthesized

<400> SEQUENCE: 17
ggccgccagg ataccacttt gcacgc                                       26

<210> SEQ ID NO 18
<211> LENGTH: 72
<212> TYPE: DNA
<213> ORGANISM: Artificial
<220> FEATURE:
<223> OTHER INFORMATION: Chemically Synthesized

<400> SEQUENCE: 18
tcgagatgta acctgtgtat ccttgtccat gtaacctgtg tatccttgtc catgtaacct   60
gtgtatcctt gc                                                      72

<210> SEQ ID NO 19
<211> LENGTH: 72
<212> TYPE: DNA
<213> ORGANISM: Artificial
<220> FEATURE:
<223> OTHER INFORMATION: Chemically Synthesized

<400> SEQUENCE: 19
ggccgcaagg atacacaggt tacatggaca aggatacaca ggttacatgg acaaggatac   60
acaggttaca tc                                                      72

<210> SEQ ID NO 20
<211> LENGTH: 26
<212> TYPE: DNA
<213> ORGANISM: Artificial
<220> FEATURE:
<223> OTHER INFORMATION: Chemically Synthesized

<400> SEQUENCE: 20

-continued

```
tcgaggccac aacgtctata tcatgc                                          26
```

<210> SEQ ID NO 21
<211> LENGTH: 26
<212> TYPE: DNA
<213> ORGANISM: Artificial
<220> FEATURE:
<223> OTHER INFORMATION: Chemically Synthesized

<400> SEQUENCE: 21

```
ggccgcatga tatagacgtt gtggcc                                          26
```

<210> SEQ ID NO 22
<211> LENGTH: 72
<212> TYPE: DNA
<213> ORGANISM: Artificial
<220> FEATURE:
<223> OTHER INFORMATION: Chemically Synthesized

<400> SEQUENCE: 22

```
tcgagcggtg atgcagtata tcaaccttcg gtgatgcagt atatcaacct tcggtgatgc     60
agtatatcaa gc                                                         72
```

<210> SEQ ID NO 23
<211> LENGTH: 72
<212> TYPE: DNA
<213> ORGANISM: Artificial
<220> FEATURE:
<223> OTHER INFORMATION: Chemically Synthesized

<400> SEQUENCE: 23

```
ggccgcttga tatactgcat caccgaaggt tgatatactg catcaccgaa ggttgatata     60
ctgcatcacc gc                                                         72
```

<210> SEQ ID NO 24
<211> LENGTH: 26
<212> TYPE: DNA
<213> ORGANISM: Artificial
<220> FEATURE:
<223> OTHER INFORMATION: Chemically Synthesized

<400> SEQUENCE: 24

```
tcgagagaag atgcttcaga cagagc                                          26
```

<210> SEQ ID NO 25
<211> LENGTH: 26
<212> TYPE: DNA
<213> ORGANISM: Artificial
<220> FEATURE:
<223> OTHER INFORMATION: Chemically Synthesized

<400> SEQUENCE: 25

```
ggccgctctg tctgaagcat cttctc                                          26
```

<210> SEQ ID NO 26
<211> LENGTH: 72
<212> TYPE: DNA
<213> ORGANISM: Artificial
<220> FEATURE:
<223> OTHER INFORMATION: Chemically Synthesized

<400> SEQUENCE: 26

```
tcgaggtgcg acctcgcaga cagagtccgt gcgacctcgc agacagagtc cgtgcgacct     60
```

```
cgcagacaga gc                                                            72

<210> SEQ ID NO 27
<211> LENGTH: 72
<212> TYPE: DNA
<213> ORGANISM: Artificial
<220> FEATURE:
<223> OTHER INFORMATION: Chemically Synthesized

<400> SEQUENCE: 27
ggccgctctg tctgcgaggt cgcacggact ctgtctgcga ggtcgcacgg actctgtctg         60
cgaggtcgca cc                                                            72

<210> SEQ ID NO 28
<211> LENGTH: 26
<212> TYPE: DNA
<213> ORGANISM: Artificial
<220> FEATURE:
<223> OTHER INFORMATION: Chemically Synthesized

<400> SEQUENCE: 28
tcgagttaag gcagacccag tatggc                                             26

<210> SEQ ID NO 29
<211> LENGTH: 26
<212> TYPE: DNA
<213> ORGANISM: Artificial
<220> FEATURE:
<223> OTHER INFORMATION: Chemically Synthesized

<400> SEQUENCE: 29
ggccgccata ctgggtctgc cttaac                                             26

<210> SEQ ID NO 30
<211> LENGTH: 72
<212> TYPE: DNA
<213> ORGANISM: Artificial
<220> FEATURE:
<223> OTHER INFORMATION: Chemically Synthesized

<400> SEQUENCE: 30
tcgagagcat tacttcccag tatcttccag cattacttcc cagtatcttc cagcattact         60
tcccagtatc gc                                                            72

<210> SEQ ID NO 31
<211> LENGTH: 72
<212> TYPE: DNA
<213> ORGANISM: Artificial Sequence
<220> FEATURE:
<223> OTHER INFORMATION: Chemically Synthesized

<400> SEQUENCE: 31
ggccgcgata ctgggaagta atgctggaag atactgggaa gtaatgctgg aagatactgg         60
gaagtaatgc tc                                                            72
```

THERAPEUTIC OLIGONUCLEOTIDES COMPRISING PYRAZOLOTRIAZINE NUCLEOTIDE ANALOGUES

RELATED APPLICATIONS

This is the U.S. National Stage of International Application No. PCT/IL2013/050465, filed May 30, 2013, which was published in English under PCT Article 21(2), and which claims the benefit of U.S. Provisional Application Ser. No. 61/653,432 filed May 31, 2012, entitled "Therapeutic Oligonucleotides Comprising Nucleotide Analogues," which is incorporated herein by reference in its entirety and for all purposes.

SEQUENCE LISTING

This application incorporates-by-reference nucleotide and/or amino acid sequences which are present in the file named "244_PCT1_ST25.txt", which is 27 kilobytes in size, and which was created May 28, 2013 in the IBM-PCT machine format, having an operating system compatibility with MS-Windows.

FIELD OF THE INVENTION

Disclosed herein are nucleic acid molecules comprising at least one pyrazolotriazine nucleotide analogue, pharmaceutical compositions comprising same and methods of use thereof for the modulation of gene expression. The nucleic acid molecules include double-stranded RNA (dsRNA), including siRNA, and saRNA useful in the treatment of subjects suffering from diseases or conditions and/or symptoms associated with such diseases or conditions or at risk of contracting diseases or conditions in which it is beneficial to modulate gene expression.

BACKGROUND OF THE INVENTION

International Patent Publication Nos. WO 2008/104978, WO 2009/044392, WO 2011/066475, WO 2011/084193 and WO 2011/085056 to a co-assignee of the present disclosure are hereby incorporated by reference in their entirety.

There remains a need for active and effective dsRNA therapeutic agents, which exhibit at least one of increased nuclease stability, increased target specificity, reduced immunogenicity or reduced off-target effects while retaining therapeutic activity.

SUMMARY OF THE INVENTION

The dsRNA nucleic acid molecules disclosed herein possess structures and modifications which, for example increase stability, reduce immunogenicity, reduce off-target effects, improve cellular uptake or enhance loading into the RISC complex when compared to an unmodified dsRNA molecule. The chemical modifications are useful in generating nucleic acid molecules for modulating target gene expression. Co-pending patent application to some of the co-inventors discloses novel pyrazolotriazine (PT) nucleotide analogues according to the general formula I and DNA oligonucleotides comprising same

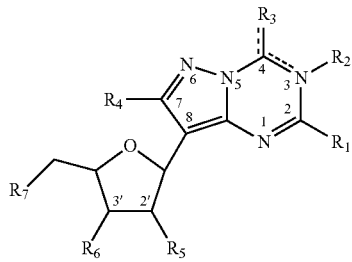

wherein $R_1$ and $R_4$ each independently is selected from H, halogen, —CN, —SCN, —NO$_2$, —O-hydrocarbyl, —S-hydrocarbyl, —CO—H, —CO-hydrocarbyl, —NR$_8$R$_9$, heteroaryl, or hydrocarbyl optionally substituted by one or more groups each independently is halogen, —CN, —SCN, or —NO$_2$, wherein $R_8$ and $R_9$ are each independently H, hydrocarbyl, or an amine protecting group; or $R_8$ and $R_9$ together with the nitrogen atom to which they are attached form a saturated or unsaturated heterocyclic ring optionally containing 1-2 further heteroatoms selected from oxygen, nitrogen or sulfur;

$R_2$ is H or absent;

$R_3$ is O or —NR$_{10}$R$_{10'}$, wherein $R_{10}$ and $R_{10'}$ are each independently H, hydrocarbyl, —CO— hydrocarbyl, or an amine protecting group; and $R_5$ is H, halogen, —O⁻, or —OR$_{11}$;

$R_6$ is —O⁻, or —OR$_{11}$;

$R_7$ is —OR$_{11}$, or a phosphate moiety;

$R_{11}$ each independently is H, (C$_1$-C$_8$)alkyl, (C$_1$-C$_8$)alkylene-OR$_{12}$, (C$_1$-C$_8$)alkylene-SR$_{12}$, (C$_1$-C$_8$)alkylene-NR$_{12}$R$_{13}$, a hydroxyl protecting group, or a phosphoramidite moiety of the formula —P(OR$_{14}$)NR$_{15}$R$_{16}$, wherein $R_{14}$ is H or cyano-(C$_1$-C$_8$)alkyl, preferably cyanoethyl, and $R_{15}$ and $R_{16}$ each independently is H or (C$_1$-C$_8$)alkyl, preferably isopropyl;

$R_{12}$ and $R_{13}$ each independently is H or (C$_1$-C$_8$)alkyl; and the dotted line represents a potential double bond between the carbon atom at position 4 and either the nitrogen atom at position 3 or the residue $R_3$, provided that, when $R_2$ is H, there is a double bond between the carbon atom at position 4 and $R_3$, and when $R_2$ is absent, there is a double bond between the carbon atom at position 4 and the nitrogen atom at position 3, but excluding the analogues wherein $R_5$ and $R_6$ each independently is —OH or —O⁻, and the analogues wherein $R_5$ is H and $R_1$ is hydrocarbyl.

In one aspect provided herein are dsRNA molecules useful for the modulation of gene expression. In various embodiments, provided are double-stranded dsRNA molecules comprising at least one pyrazolotriazine (PT) nucleotide analogue. In some embodiments the double-stranded RNA molecule includes saRNA. In some embodiments, the double-stranded RNA molecule includes siRNA. The at least one PT nucleotide analogue is present in the sense strand, in the antisense strand or in the both the sense strand and the antisense strand.

In various embodiments provided herein is a double-stranded RNA molecule comprising a PT nucleotide analog of the general formula II:

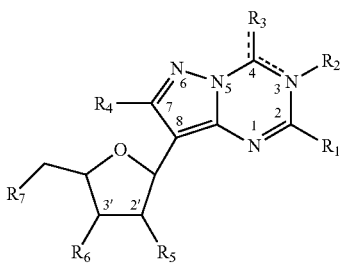

(II)

wherein $R_1$ and $R_4$ each independently is selected from H, halogen, —CN, —SCN, —NO$_2$, —O-hydrocarbyl, —S-hydrocarbyl, —CO—H, —CO-hydrocarbyl, —NR$_8$R$_9$, heteroaryl, or hydrocarbyl optionally substituted by one or more groups each independently a halogen, —CN, —SCN, or —NO$_2$, wherein $R_8$ and $R_9$ are each independently H or hydrocarbyl, or $R_8$ and $R_9$ together with the nitrogen atom to which they are attached form a saturated or unsaturated heterocyclic ring optionally containing 1-2 further heteroatoms selected from oxygen, nitrogen or sulfur;

$R_2$ is H or absent;

$R_3$ is O or —NR$_{10}$R$_{10'}$, wherein $R_{10}$ and $R_{10'}$ are each independently H, hydrocarbyl or —CO— hydrocarbyl;

$R_5$ is H, halogen, —O$^-$ or —OR$_{11}$;

$R_6$ is —O$^-$ or —OR$_{11}$, $R_7$ is OR$_{11}$, a monophosphate moiety or a phosphate linking moiety; and $R_{11}$ each independently is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein $R_{12}$ and $R_{13}$ each independently is H or (C$_1$-C$_8$) alkyl; and the dotted line represents a potential double bond between the carbon atom at position 4 and either the nitrogen atom at position 3 or the radical R3, provided that when $R_2$ is H, there is a double bond between the carbon atom at position 4 and $R_3$, and when $R_2$ is absent, there is a double bond between the carbon atom at position 4 and the nitrogen atom at position 3.

In some embodiments the PT nucleotide analogue comprises an adenine PT nucleotide analogue of Formula IIa, or a guanine PT nucleotide analogue of Formula IIb, as follows in Table 1:

is H, $R_{10}$ is H; $R_4$ is H; $R_5$ is H, halogen or —OR$_{11}$, wherein $R_{11}$ is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein $R_{12}$ and $R_{13}$ each is independently H or (C$_1$-C$_8$)alkyl; $R_6$ is —O$^-$ or —OH; and $R_7$ is OH or a phosphate linking moiety. In some embodiments $R_{11}$ is H, CH$_3$ or (CH$_2$)$_2$—OCH$_3$. In some embodiments $R_{11}$ is H (i.e. $R_5$ is hydroxy; 2'OH). In some embodiments $R_{11}$ is CH$_3$ (i.e. $R_5$ is methoxy, 2'OMe). In some embodiments $R_{11}$ is (CH$_2$)$_2$—OCH$_3$ (i.e. $R_5$ is methoxyethoxy; 2'MOE).

In some preferred embodiments the pyrazolotriazine (PT) nucleotide analogue is a deoxyadenosine PT nucleotide analogue of formula IIa wherein $R_1$ is H, $R_{10}$ is H; $R_4$ is H; $R_5$ is H or halogen; $R_6$ is —O$^-$ or —OH; and $R_7$ is OH or a phosphate moiety. In some embodiments $R_5$ is H. In some embodiments $R_5$ is halogen, preferably fluoro (F).

In some preferred embodiments the pyrazolotriazine (PT) nucleotide analogue is a guanosine PT nucleotide analogue of formula IIb wherein each of $R_4$, $R_8$ and $R_9$ is H, $R_5$ is —OR$_{11}$, wherein $R_{11}$ is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein $R_{12}$ and $R_{13}$ each is independently H or (C$_1$-C$_8$) alkyl; $R_6$ is —O$^-$ or —OH; and $R_7$ is OH or a phosphate moiety. In some embodiments $R_{11}$ is H, CH$_3$ or (CH$_2$)$_2$—OCH$_3$. In some embodiments $R_{11}$ is H (i.e. $R_5$ is hydroxy; 2'OH). In some embodiments $R_{11}$ is CH$_3$ (i.e. $R_5$ is methoxy, 2'-OMethyl). In some embodiments $R_{11}$ is (CH$_2$)$_2$—OCH$_3$ (i.e. $R_5$ is methoxyethoxy; 2'MOE).

In some preferred embodiments the pyrazolotriazine (PT) nucleotide analogue is a deoxyguanosine PT nucleotide analogue of formula IIb (i.e. $R_2$ is H and $R_3$ is O) wherein each of $R_4$, $R_8$ and $R_9$ is H, $R_5$ is H, halogen or —OR$_{11}$; $R_6$ is —O$^-$ or —OH; and $R_7$ is OH or a phosphate linking moiety. In some embodiments $R_5$ is H. In some embodiments $R_5$ is halogen, preferably fluoro (F).

In some embodiments provided are double-stranded RNA molecules, wherein:

(a) the double-stranded RNA molecule includes a sense strand and an antisense strand wherein each strand is independently 15 to 49 nucleotides in length;

(b) the sense strand and/or the antisense strand includes at least one pyrazolotriazine nucleotide analogue;

(c) a 15 to 49 ribonucleotide sequence of the antisense strand is complementary to a sequence of an mRNA of a target gene; and

TABLE 1

Adenine and guanine PT nucleotide analogues of formulas IIa and IIb

| IIa | IIb |
|---|---|

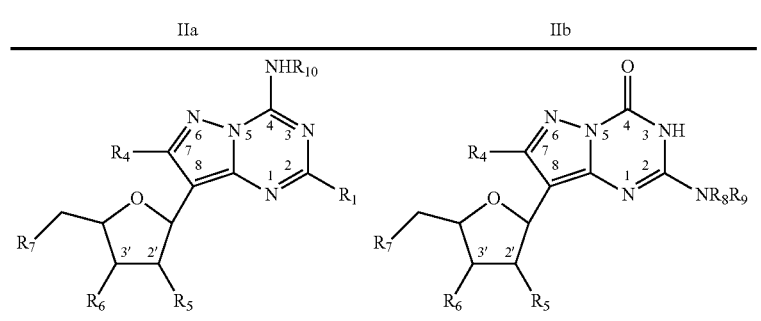

In some preferred embodiments the pyrazolotriazine (PT) nucleotide analogue is an adenine PT nucleotide analogue of formula IIa (i.e. $R_2$ is absent and $R_3$ is NHR$_{10}$) wherein $R_1$ (d) a 15 to 49 nucleotide sequence of the sense strand is complementary to the antisense strand and includes a 15 to 49 nucleotide sequence of an mRNA of a target gene.

In some embodiments the double-stranded ribonucleic acid molecule has a structure set forth below in structure A1:

(A1)

wherein each of N and N' is an unmodified ribonucleotide, a modified ribonucleotide, or an unconventional moiety;
wherein at least one of N or N' comprises a pyrazolotriazine (PT) nucleotide analogue;
wherein each of (N)x and (N')y is an oligonucleotide in which each consecutive N or N' is joined to the next N or N' by a covalent bond;
wherein each of Z and Z' is independently present or absent, but if present independently includes 1-5 consecutive nucleotides, pyrazolotriazine nucleotide analogues or non-nucleotide moieties or a combination thereof, or a vitamin or a drug moiety covalently attached at the 3' terminus of the strand in which it is present;
wherein z" may be present or absent, but if present is a capping moiety, a vitamin or a drug moiety covalently attached at the 5' terminus of (N')y;
wherein each of x and y is independently an integer between 15 and 49; and
wherein the sequence of (N')y is complementary to the sequence of (N)x and wherein at least a portion of the sequence of (N)x is complementary to a consecutive sequence in a target RNA; with the proviso that not each N and N' is a deoxyribonucleotide.

In some embodiments the covalent bond joining each consecutive N or N' is a phosphodiester bond.

In some embodiments x=y and each of x and y is 19, 20, 21, 22 or 23. In preferred embodiments x=y=19.

In some embodiments Z is present and comprises 2 pyrazolotriazine nucleotide analogues. In some embodiments Z' is present and comprises 2 pyrazolotriazine nucleotide analogues. In some embodiments Z and Z' are present and each comprises 2 pyrazolotriazine nucleotide analogues.

In some embodiments, x=y=19 and a pyrazolotriazine nucleotide analogue is present at position 1 of the antisense strand. In some embodiments, x=y=19 and a pyrazolotriazine nucleotide analogue is present at position 3, 4, 5, 6, 7 or 8 of the antisense strand. In some embodiments, x=y=19 and a pyrazolotriazine nucleotide analogue is present at position 3 of the antisense strand. In some embodiments, x=y=19 and a pyrazolotriazine nucleotide analogue is present at position 4 of the antisense strand. In some embodiments, x=y=19 and a pyrazolotriazine nucleotide analogue is present at position 5 of the antisense strand. In some embodiments, x=y=19 and a pyrazolotriazine nucleotide analogue is present at position 6 of the antisense strand. In some embodiments, x=y=19 and a pyrazolotriazine nucleotide analogue is present at position 7 of the antisense strand. In some embodiments, x=y=19 and a pyrazolotriazine nucleotide analogue is present at position 8 of the antisense strand. In some embodiments the sense strand comprises a PT nucleotide analogue at the 3' terminus. In some embodiments sense strand includes a PT nucleotide analogue at the 3' terminal position or 3' penultimate position. In some embodiments, x=y=19 and a pyrazolotriazine nucleotide analogue is present at position (5'>3') 17, 18 or 19 of the sense strand.

In some embodiments of Structure A1 the sense strand comprises at least one pyrazolotriazine nucleotide analogue. In some embodiments the antisense strand comprises at least one pyrazolotriazine nucleotide analogue. In some embodiments each of the sense strand and the antisense strand comprises at least one pyrazolotriazine nucleotide analogue.

In various embodiments the 5' terminus of the antisense strand comprises a PT nucleotide analogue of general formula IIa selected from compounds 3, 7, 9, 13, 15, 19, 21, 25, 27 or 31. In various embodiments the 5' terminus of the antisense strand comprises a PT nucleotide analogue of general formula IIa selected from compounds 3, 7, 9, 13, 15, 19, 21, 25, 27 or 31. In various embodiments the 5' terminus of the sense strand comprises a PT nucleotide analogue of general formula IIb selected from compounds 33, 37, 39, 43, 45, 49, 51, 55, 57 or 61.

In various embodiments the 3' terminus of the sense strand comprises a PT nucleotide analogue of general formula IIa selected from compounds 5, 11, 17, 23 or 29. In various embodiments the 3' position of the antisense strand comprises a PT nucleotide analogue of general formula IIa selected from compounds 5, 11, 17, 23 or 29. In various embodiments the 3' position of the sense strand comprises a PT nucleotide analogue of general formula IIb selected from compounds 35, 41, 47, 53 or 59. In various embodiments the 3' position of the antisense strand comprises a PT nucleotide analogue of general formula IIb selected from compounds 35, 41, 47, 53 or 59.

In various embodiments the sense strand comprises a PT nucleotide analogue of general formula IIa selected from compounds 7, 13, 19, 25 or 31 in an internal position. In various embodiments the antisense strand comprises a PT nucleotide analogue of general formula IIa selected from compounds 7, 13, 19, 25 or 31 in an internal position. In various embodiments the sense strand comprises a PT nucleotide analogue of general formula IIb selected from compounds 37, 43, 49, 55 or 61 in an internal position. In various embodiments the antisense strand comprises a PT nucleotide analogue of general formula IIb selected from compounds 37, 43, 49, 55 or 61 in an internal position.

In some embodiments all of the adenosines in the sense strand are substituted with adenosine and/or deoxyadenosine pyrazolotriazine nucleotide analogues. In some embodiments all of the adenosines in the antisense strand are substituted with adenosine and/or deoxyadenosine pyrazolotriazine nucleotide analogues. In some embodiments all of the adenosines in the sense strand and in the antisense strand are substituted with adenosine and/or deoxyadenosine pyrazolotriazine nucleotide analogues.

In some embodiments, the ribonucleotide in position 1 (5'>3') of the antisense strand is substituted with an adenosine or deoxyadenosine PT nucleotide analogue as described herein.

In some embodiments, the ribonucleotide in position 3, 4, 5, 6, 7, 8 or 9 (5'>3') of the antisense strand is substituted with a PT nucleotide analogue as described herein. In some embodiments, the ribonucleotide in position 3 (5'>3') of the antisense strand is substituted with an adenosine or deoxyadenosine PT nucleotide analogue. In some embodiments, the ribonucleotide in position 4 (5'>3') of the antisense strand is substituted with an adenosine or deoxyadenosine PT nucleotide analogue. In some embodiments, the ribonucleotide in position 5 (5'>3') of the antisense strand is substituted with an adenosine or deoxyadenosine PT nucleotide analogue.

In some embodiments, the ribonucleotide in position 18 (5'>3') of the sense strand is substituted with a PT nucleotide analogue. In some embodiments the PT nucleotide analogue is an adenosine or deoxyadenosine PT nucleotide analog. In some embodiments the PT nucleotide analogue is a guanosine or deoxyguanosine PT nucleotide analog.

In some embodiments all of the guanosines in the sense strand are substituted with guanosine and/or deoxyguanosine pyrazolotriazine nucleotide analogues. In some embodiments all of the guanosines in the antisense strand are substituted with guanosine and/or deoxyguanosine pyrazolotriazine nucleotide analogues. In some embodiments all of the guanosines in the sense strand and in the antisense strand are substituted with guanosine or deoxyguanosine pyrazolotriazine nucleotide analogues.

In some embodiments the sequence of (N')y is fully complementary to the sequence of (N)x. In some embodiments the sequence of (N)x is fully complementary to a consecutive sequence in a target RNA.

In various embodiments provided herein is a double-stranded ribonucleic acid molecule wherein the guide strand (antisense strand) comprises a mismatch to the target mRNA at the 5' terminal nucleotide. Accordingly, in various embodiments provided is a double-stranded ribonucleic acid molecule having the following structure A2:

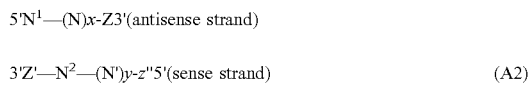

3'Z'—N²—(N')y-z"5'(sense strand)    (A2)

wherein each of N², N and N' is an unmodified or modified ribonucleotide, or an unconventional moiety;
wherein at least one of N¹, N², N or N' comprises a pyrazolotriazine nucleotide analogue;
wherein each of (N)x and (N')y is an oligonucleotide in which each consecutive N or N' is joined to the adjacent N or N' by a covalent bond;
wherein each of x and y is independently an integer between 17 and 24;
wherein the sequence of (N')y is complementary to the sequence of (N)x and wherein at least a portion of the sequence of (N)x is complementary to a consecutive sequence in a target RNA;
wherein N¹ is covalently bound to (N)x and is mismatched to the target RNA or is a complementary DNA moiety to the target RNA;
wherein N¹ is a moiety selected from the group consisting of natural or modified uridine, deoxyribouridine, ribothymidine, deoxyribothymidine, natural or modified adenosine, deoxyadenosine, adenosine pyrazolotriazine nucleic acid analogue, and deoxyadenosine pyrazolotriazine nucleic acid analogue; wherein z" may be present or absent, but if present is a capping moiety, a vitamin or a drug moiety covalently attached at the 5' terminus of N²—(N')y; and
wherein each of Z and Z' is independently present or absent, but if present is independently 1-5 consecutive nucleotides, pyrazolotriazine nucleotide analogues, consecutive non-nucleotide moieties or a combination thereof, or a vitamin or a drug moiety covalently attached at the 3' terminus of the strand in which it is present; with the proviso that not each N and N' is a deoxyribonucleotide.

In preferred embodiments the pyrazolotriazine nucleotide analogue in the dsRNA molecule comprises an adenine PT nucleotide analogue of Formula IIa or a guanine PT nucleotide analogue of Formula IIb.

In preferred embodiments of structure A2, x=y=18. In some embodiments the sense strand of a molecule of Structure A2 comprises at least one pyrazolotriazine nucleotide analogue. In some embodiments the antisense strand comprises at least one pyrazolotriazine nucleotide analogue. In some embodiments each of the sense strand and the antisense strand comprises at least one pyrazolotriazine nucleotide analogue. In various embodiments the 5' terminus of the sense strand comprises a PT nucleotide analogue of general formula IIa selected from compounds 3, 7, 9, 13, 15, 19, 21, 25, 27 or 31. In various embodiments the 5' terminus of the antisense strand comprises a PT nucleotide analogue of general formula IIa selected from compounds 3, 7, 9, 13, 15, 19, 21, 25, 27 or 31. In various embodiments the 5' terminus of the sense strand comprises a PT nucleotide analogue of general formula IIb selected from compounds 33, 37, 39, 43, 45, 49, 51, 55, 57 or 61.

In various embodiments the 3' terminus of the sense strand comprises a PT nucleotide analogue of general formula IIa selected from compounds 5, 11, 17, 23 or 29. In various embodiments the 3' position of the antisense strand comprises a PT nucleotide analogue of general formula IIa selected from compounds 5, 11, 17, 23 or 29. In various embodiments the 3' position of the sense strand comprises a PT nucleotide analogue of general formula IIb selected from compounds 35, 41, 47, 53 or 59. In various embodiments the 3' position of the antisense strand comprises a PT nucleotide analogue of general formula IIb selected from compounds 35, 41, 47, 53 or 59.

In various embodiments the sense strand comprises a PT nucleotide analogue of general formula IIa selected from compounds 7, 13, 19, 25 or 31 in an internal position. In various embodiments the antisense strand comprises a PT nucleotide analogue of general formula IIa selected from compounds 7, 13, 19, 25 or 31 in an internal position. In various embodiments the sense strand comprises a PT nucleotide analogue of general formula IIb selected from compounds 37, 43, 49, 55 or 61 in an internal position. In various embodiments the antisense strand comprises a PT nucleotide analogue of general formula IIb selected from compounds 37, 43, 49, 55 or 61 in an internal position.

In some embodiments the sequence of (N')y is fully complementary to the sequence of (N)x. In various embodiments sequence of N²—(N')y is complementary to the sequence of N¹—(N)x. In some embodiments (N)x comprises an antisense that is fully complementary to about 17 to about 24 consecutive nucleotides in a target RNA. In other embodiments (N)x comprises an antisense that is substantially complementary to about 17 to about 39 consecutive nucleotides in a target RNA.

In some embodiments N¹ and N² form a Watson-Crick base pair. In some embodiments N¹ and N² form a non-Watson-Crick base pair. In some embodiments a base pair is formed between a ribonucleotide and a deoxyribonucleotide.

In some embodiments x=y=18, x=y=19 or x=y=20. In preferred embodiments x=y=18.

In some embodiments N¹ is covalently bound to (N)x and is mismatched to the target RNA. In various embodiments N¹ is covalently bound to (N)x and is a DNA moiety complementary to the target RNA.

In some embodiments N¹ is covalently bound to (N)x and is a DNA moiety complementary to the target RNA.

In some embodiments N¹ is selected from adenosine, deoxyadenosine, natural or modified uridine, deoxyuridine, ribothymidine or deoxythymidine, adenosine pyrazolotriazine nucleotide analogue or deoxyadenosine pyrazolotriazine nucleotide analogue; and wherein the pairing nucleotide in the target RNA is adenosine. In preferred embodiments N¹ is selected from adenosine, deoxyadenosine or deoxyuridine.

In some embodiments N¹ is selected from adenosine, deoxyadenosine, a pyrazolotriazine nucleotide analogue of adenosine or deoxyadenosine, uridine, deoxyuridine, ribothymidine or deoxythymidine and wherein the pairing nucleotide in the target RNA is cytidine. In preferred embodiments N¹ is selected from adenosine, deoxyadenosine, a pyrazolotriazine nucleotide analogue of adenosine or deoxyadenosine, uridine or deoxyuridine.

In some embodiments $N^1$ is selected from adenosine, deoxyadenosine, a pyrazolotriazine nucleotide analogue of adenosine or deoxyadenosine, uridine, deoxyuridine, ribothymidine or deoxythymidine and wherein the nucleotide in the pairing nucleotide in the target RNA is guanosine.

In preferred embodiments $N^1$ is selected from adenosine, deoxyadenosine, a pyrazolotriazine nucleotide analogue of adenosine or deoxyadenosine, uridine or deoxyuridine.

In some embodiments $N^1$ is selected from deoxyadenosine, a pyrazolotriazine nucleotide analogue of adenosine or deoxyadenosine, deoxyuridine, ribothymidine or deoxythymidine and wherein the nucleotide in the pairing nucleotide in the target RNA is uridine. In preferred embodiments $N^1$ is selected from deoxyadenosine or deoxyuridine.

In some embodiments $N^1$ and $N^2$ form a base pair between uridine or deoxyuridine, and adenosine or deoxyadenosine. In other embodiments $N^1$ and $N^2$ form a base pair between deoxyuridine and adenosine.

In some embodiments of the double-stranded ribonucleic acid molecules, including Structures A1 and A2, the PT nucleotide analogue comprises a deoxyribose. In some embodiments of the double-stranded ribonucleic acid molecules, including Structures A1 and A2, the PT nucleotide analogue comprises an unmodified ribose or a modified ribose. In some embodiments the modified ribonucleotide comprises a modification at the 2' position of the sugar moiety and includes a 2' alkyl, 2' alkoxy, 2' amino or 2' fluoro modification. In some embodiments the 2' modification is a 2' alkoxy modification selected from 2' methoxy (2' OMe), 2' ethoxy (2' OEt) or 2' methoxyethoxy (2'MOE) modification.

In some embodiments of the double-stranded ribonucleic acid molecules, including Structures A1 and A2, the sense strand or the antisense strand or both strands comprise at least one adenine pyrazolotriazine nucleotide analogue. In some embodiments of the double-stranded ribonucleic acid molecules, including Structures A1 and A2, the sense strand or the antisense strand or both strands comprise at least one deoxyadenosine PT nucleotide analogue. In preferred embodiments the adenosine PT nucleotide analogue and the deoxyadenosine PT nucleotide analogue are of formula IIa.

In some embodiments of the double-stranded ribonucleic acid molecules, including Structures A1 and A2, the sense strand or the antisense strand or both strands comprise a guanosine pyrazolotriazine nucleotide analogue. In some embodiment of the double-stranded ribonucleic acid molecules, including Structures A1 and A2, the sense strand or the antisense strand or both strands comprise at least one deoxyguanosine pyrazolotriazine nucleotide analogue. In preferred embodiments the guanosine pyrazolotriazine nucleotide analogue and the deoxyguanosine pyrazolotriazine nucleotide analogue are of formula IIb.

In some embodiments of the double-stranded ribonucleic acid molecules, including Structures A1 and A2, the antisense strand comprises one or more deoxyadenosine pyrazolotriazine nucleic acid analogues and/or one or more adenosine pyrazolotriazine nucleic acid analogues in place of one or more adenosine ribonucleotides. In some embodiments (N)x comprises one or more deoxyguanosine pyrazolotriazine nucleic acid analogues and/or one or more guanosine pyrazolotriazine nucleic acid analogues in place of one or more guanosine ribonucleotides.

In some embodiments of the double-stranded ribonucleic acid molecules, including Structures A1 and A2, the sense strand comprises one or more deoxyadenosine pyrazolotriazine nucleic acid analogues and/or one or adenosine pyrazolotriazine nucleic acid analogues in place of one or more adenosine ribonucleotides. In some embodiments (N')y comprises one or more deoxyguanosine pyrazolotriazine nucleic acid analogues and/or one or more guanosine pyrazolotriazine nucleic acid analogues in place of one or more guanosine ribonucleotides. In preferred embodiments the sense strand ($N^2$—(N')y or (N')y comprises one or more pyrazolotriazine nucleic acid analogues and one or more modified ribonucleotide or unconventional moiety.

In some embodiments of the double-stranded ribonucleic acid molecules, including Structures A1 and A2, the sense strand includes at least one PT nucleotide analogue. In some embodiments of the double-stranded ribonucleic acid molecules, including Structures A1 and A2, the antisense strand includes at least one PT nucleotide analogue. In preferred embodiments y=19. In some embodiments the sense strand comprises 1, 2, 3, 4, 5, 6, 7, 8, 9, 10, 11, 12, 13 or 14 pyrazolotriazine nucleic acid analogues. In some embodiments the sense strand comprises 1, 2, 3, 4, 5, 6, 7 or 8 pyrazolotriazine nucleic acid analogues. In some embodiments the sense strand comprises at least one PT nucleotide analogue to replace an adenosine or guanosine ribonucleotide and further comprises at least one 2'OMe sugar modified pyrimidine ribonucleotide, and the antisense strand optionally comprises a pyrazolotriazine nucleic acid analogue in one of positions 5, 6, 7, 8 or 9 from the 5' terminus.

In some embodiments of the double-stranded ribonucleic acid molecules, including Structures A1 and A2, the sense strand includes at least one PT nucleotide analogue and at least one further modified ribonucleotide or unconventional moiety. In some embodiments the unconventional moiety is selected from a mirror nucleotide, a 2'5' linked nucleotide and a threose nucleic acid.

In some embodiments of the double-stranded ribonucleic acid molecules, including Structures A1 and A2, the antisense strand includes a pyrazolotriazine nucleic acid analogue in one of positions 5, 6, 7, 8 or 9 from the 5' terminus and further includes one or more 2'OMe sugar modified pyrimidine ribonucleotides. In some embodiments the sense strand includes 2-5 consecutive 2'5' linked nucleotides at the 3' terminus and optionally further includes at least one 2'OMe sugar modified pyrimidine ribonucleotide.

In some embodiments of the double-stranded ribonucleic acid molecules, including Structures A1 and A2, each N that is a purine, is substituted with a PT nucleotide analogue. In some embodiments of the double-stranded nucleic acid molecules, including Structures A1 and A2, at least one N which is a purine, is a PT nucleotide analogue and another N in at least one of positions 5, 6, 7, 8, or 9 from the 5' terminus of the antisense strand [(N)x of (A1) or $N^1$—(N)x of (A2)] is selected from a threose nucleic acid (TNA) moiety, a 2'5' linked nucleotide or a mirror nucleotide.

In some embodiments the antisense strand [e.g. (N)x of (A1) or $N^1$—(N)x of (A2)] comprises a PT nucleotide analogue in at least one of (5'>3') positions 1, 2, 3, 4, 5, 6, 7, 8, 9, 10, 11, 12, 13, 14, 15, 16, 17, 18 or 19, preferably in position 1 and further comprises a TNA moiety in (5'>3') position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments the antisense strand [e.g. (N)x of (A1) or $N^1$—(N)x of (A2)] comprises a PT nucleotide analogue in at least one of (5'>3') positions 1, 2, 3, 4, 5, 6, 7, 8, 9, 10, 11, 12, 13, 14, 15, 16, 17, 18 or 19, preferably in position 1 and further comprises a 2'5' linked nucleotide in (5'>3') position 5 from the 5' terminus. In some embodiments the antisense strand comprises a 2'5' linked nucleotide or PT nucleotide analogue in (5'>3') position 6 from the 5' terminus. In some embodiments the antisense strand comprises a 2'5' linked nucleotide in position 7 from the 5' terminus. In some embodiments the antisense strand comprises a 2'5' linked nucleotide in position 8 from the 5' terminus. In some embodiments the antisense strand comprises a 2'5' linked nucleotide in position 9 from the 5' terminus.

In some embodiments the antisense strand [e.g. (N)x of (A1) or $N^1$—(N)x of (A2)] comprises a PT nucleotide analogue in at least one of positions (5'>3') 1, 2, 3, 4, 5, 6, 7, 8, 9, 10, 11, 12, 13, 14, 15, 16, 17, 18 or 19, preferably in position 1 and further comprises a mirror nucleotide in (5'>3') position 5 from the 5' terminus. In some embodiments the antisense strand comprises a mirror nucleotide in position 6 from the 5' terminus. In some embodiments the antisense strand comprises a mirror nucleotide in position 7 from the 5' terminus. In some embodiments the antisense strand comprises a mirror nucleotide in position 8 from the 5' terminus. In some embodiments the antisense strand comprises a mirror nucleotide in position 9 from the 5' terminus.

In some embodiments the sense strand [e.g. (N')y of (A1) or $N^2$—(N')y of (A2)] comprises a PT nucleotide analogue in at least one position, preferably in position 1 and further comprises a threose nucleic acid moiety in position 9 from the 5' terminus. In some embodiments the sense strand comprises a PT nucleotide analogue in at least one position and further comprises a threose nucleic acid moiety in position 10 from the 5' terminus.

In some embodiments the sense strand [e.g. (N')y of (A1) or $N^2$—(N')y of (A2)] comprises a PT nucleotide analogue in at least one position preferably in position 1 and further comprises a 2'5' linked nucleotide in position 9 from the 5' terminus. In some embodiments the sense strand [(N')y of (A1) or $N^2$—(N')y of (A2)] comprises a PT nucleotide analogue in at least one position and further comprises a 2'5' linked nucleotide in position 10 from the 5' terminus.

In some embodiments the sense strand [e.g. (N')y of (A1) or $N^2$—(N')y of (A2)] comprises a PT nucleotide analogue in at least one position preferably in position 1 and further comprises a pseudoUridine in position 9 from the 5' terminus. In some embodiments the sense strand [(N')y of (A1) or $N^2$—(N')y of (A2)] comprises a PT nucleotide analogue in at least one position and further comprises a pseudoUridine in position 10 from the 5' terminus.

In some embodiments the sense strand [e.g. (N')y of (A1) or $N^2$—(N')y of (A2)] comprises a PT nucleotide analogue in at least one position preferably in position 1 and further comprises 2, 3, 4, 5, 6, 7, 8, 9 or 10 threose nucleic acid moieties at the 3' terminal or penultimate positions of the sense strand. In some embodiments the sense strand [e.g. (N')y of (A1) or $N^2$—(N')y of (A2)] comprises a PT nucleotide analogue in at least one position and further comprises 2, 3, 4, 5, 6, 7 or 8 consecutive threose nucleic acid moieties at the 3' terminal or penultimate positions of the sense strand. In some embodiments the sense strand [e.g. (N')y of (A1) or $N^2$—(N')y of (A2)] comprises a PT nucleotide analogue in at least one position and further comprises threose nucleic acid moieties in positions 18-19, 17-18, 16-17, or 15-16 from the 5' terminus. In some embodiments the sense strand [e.g. (N')y of (A1) or $N^2$—(N')y of (A2)] comprises a PT nucleotide analogue in at least one position and further comprises threose nucleic acid moieties in positions 15-17, 15-18 or 15-19 from the 5' terminus. In some embodiments the sense strand [e.g. (N')y of (A1) or $N^2$—(N')y of (A2)] comprises a PT nucleotide analogue replacing a purine ribonucleotide in at least one position and further comprises threose nucleic acid moieties in positions 11-19, 12-19, 13-19, 14-19, 15-19, 16-19 or 17-19, from the 5' terminus. In some embodiments the sense strand [e.g. (N')y of (A1) or $N^2$—(N')y of (A2)] comprises a PT nucleotide analogue replacing a purine ribonucleotide in at least one position and further comprises threose nucleic acid moieties in positions 11-18, 12-18, 13-18, 14-18, 15-18 or 16-18 from the 5' terminus.

In some embodiments the double-stranded ribonucleic acid molecule includes at least one PT nucleotide analogue in the sense strand or in the antisense strand or in both the sense strand, preferably in position 1 of the antisense strand and the dsRNA further includes a combination of the following modifications.

a) the antisense strand includes a 2'5' linked nucleotide, TNA moiety or a mirror nucleotide in at least one of positions 5, 6, 7, 8, or 9 from the 5' terminus; and
b) the sense strand includes at least one of a 2'5' linked nucleotide or a TNA moiety in positions 9 or 10 from the 5' terminus In some embodiments the double-stranded ribonucleic acid molecule includes at least one PT nucleotide analogue in the sense strand or in the antisense strand or in both the sense strand and the antisense strand and further includes a combination of the following modifications.

a) the antisense strand includes a 2'5' linked nucleotide, TNA moiety or a mirror nucleotide in at least one of positions 5, 6, 7, 8, or 9 from the 5' terminus; and
b) the sense strand includes 2, 3, 4, 5, 6, 7, 8, 9 or 10 consecutive TNA at the 3' penultimate position or 3' terminus.

In some embodiments in the double-stranded ribonucleic acid molecule the sense strand further includes a capping moiety covalently attached to the 5' terminus (z"). In some embodiments Z and or Z' is present and includes a nucleotide or non-nucleotide overhang covalently attached to the 3' terminus of the strand in which it is present. In some embodiments Z includes a dTdT dinucleotide overhang or a C3Pi-C3Pi non-nucleotide overhang. In some embodiments Z' includes a dTdT dinucleotide overhang or a C3Pi or C3OH non-nucleotide overhang.

In some embodiments the double-stranded ribonucleic acid molecule includes a threose nucleic acid moiety or a 2'5' linked nucleotide or a mirror nucleotide in at least one of positions 5, 6, 7, 8, or 9 from the 5' terminus of the antisense strand and 1, 2, 3, 4, 5, 6, 7, 8, 9 or 10 threose nucleic acid moieties at the 3' terminal or penultimate positions of the sense strand. The sense strand and/or the antisense strand optionally further include at least one 2'OMe sugar modified pyrimidine ribonucleotide. In some embodiments the sense strand includes at least one 2'OMe sugar modified pyrimidine ribonucleotide. In some embodiments the antisense strand includes at least one 2'OMe sugar modified pyrimidine ribonucleotide. In some embodiments both the sense strand and the antisense strand include at least one 2'OMe sugar modified pyrimidine ribonucleotide. In some embodiments the double-stranded molecule further includes a capping moiety covalently attached to the 5' terminus of the sense strand.

In another embodiment the double-stranded ribonucleic acid molecule includes a PT nucleotide analogue, and a threose nucleic acid moiety or a 2'5' linked nucleotide or a mirror nucleotide in at least one of positions 5, 6, 7, 8, or 9 from the 5' terminus of the antisense strand and 4, 5 or 6, 2'5' linked nucleotide at the 3' terminal or penultimate positions of the sense strand. In some embodiments the double-stranded molecule further comprises a 2'5' linked nucleotide in position 9 or 10 in the sense strand. In additional embodiments, the sense strand, the antisense strand or both strands further include 2'OMe sugar modified pyrimidine ribonucleotides.

In another embodiment the double-stranded ribonucleic acid molecule includes a PT nucleotide analogue and at least one threose nucleic acid moiety, a 2'5' linked nucleotide or a mirror nucleotide in positions 5, 6, 7, 8, or 9 from the 5' terminus of the antisense strand; and comprises 2, 3, 4, 5, 6, 7, 8, 9, or 10 consecutive 2'5' linked nucleotide at the 3' terminal or penultimate position positions of the sense strand.

In another embodiment the double-stranded ribonucleic acid molecule includes a PT nucleotide analogue and at least one threose nucleic acid moiety, a 2'5' linked nucleotide or a mirror nucleotide in positions 5, 6, 7, 8, or 9 from the 5' terminus of the antisense strand; and comprises 2, 3, 4, 5, 6, 7, 8, 9, or 10 consecutive TNA moieties at the 3' terminal or penultimate position of the sense strand.

In another aspect provided are compositions comprising a double-stranded RNA nucleic acid molecule wherein:
(a) the ribonucleic acid molecule includes a sense strand and an antisense strand wherein each strand is independently 15 to 49 nucleotides in length;
(b) the sense strand and/or the antisense strand includes at least one pyrazolotriazine nucleotide analogue;
(c) a 15 to 49 nucleotide sequence of the antisense strand is complementary to a sequence of an mRNA of a target gene; and
(d) a 15 to 49 nucleotide sequence of the sense strand is complementary to the antisense strand and includes a 15 to 49 nucleotide sequence of an mRNA of a target gene;
in an amount effective to down regulate expression of a gene; and a pharmaceutically acceptable carrier.

In some embodiments each of the antisense strand and sense strand is 19-21 nucleotides and the PT nucleotide analogue is present at the 5' terminus of the antisense strand (position 1) or at the 3' terminus (i.e. position 19, 20 and/or 21) or penultimate position (position 18) of the sense strand.

In some embodiments, the gene is a mammalian gene. In other embodiments the gene is a non-mammalian gene, for example a bacterial, viral or fungal gene.

In some embodiments the double-stranded RNA nucleic acid molecule is according to Structure (A1). In some embodiments the double-stranded nucleic acid molecule is according to Structure (A2).

In some embodiments the mammalian gene is a human gene. In some embodiments the non-mammalian gene is a bacterial gene or a viral gene. In some embodiments the non-mammalian gene is involved in a mammalian disease, preferably human disease.

Further provided are methods for treating or preventing the incidence or severity of a disease or condition and/or for reducing the risk or severity of a disease or condition in a subject in need thereof wherein the disease or condition and/or a symptom and/or risk associated therewith is associated with expression of a mammalian or a non-mammalian gene. In a preferred embodiment the subject is a human subject.

In another aspect, provided are the double-stranded ribonucleic acid molecules and composition comprising such molecules, according to any of the embodiments described herein, for use in down-regulating a target gene expression, wherein the target gene is a mammalian or non-mammalian target gene.

Further provided is the use of the double-stranded ribonucleic acid molecules or compositions comprising such molecules, according to any of the embodiments described herein, for the manufacture of a medicament for use in therapy.

In some embodiments the disease or condition is selected from hearing loss, acute renal failure (ARF), Delayed Graft Function (DGF) after kidney transplantation, glaucoma, ocular ischemic conditions including anterior ischemic optic neuropathy, age-related macular degeneration (AMD), Ischemic Optic Neuropathy (ION), dry eye syndrome, acute respiratory distress syndrome (ARDS) and other acute lung and respiratory injuries, chronic obstructive pulmonary disease (COPD), primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, organ transplantation including lung, liver, heart, pancreas, and kidney transplantation, nephro- and neurotoxicity, spinal cord injury, brain injury, neurodegenerative disease or condition, pressure sores, oral mucositis fibrotic conditions including liver fibrosis, lung fibrosis; ocular neuropathy, elevated intraocular pressure (IOP), Sjögrens Syndrome, diabetic retinopathy (DR), diabetic macular edema (DME), optic neuritis, central retinal vein occlusion, brunch retinal vein occlusion, optic nerve injury, retinopathy of prematurity (ROP), retinitis pigmentosa (RP), retinal ganglion degeneration, macular degeneration, hereditary optic neuropathy, Leber's hereditary optic neuropathy, neuropathy due to a toxic agent and neuropathy caused by an adverse drug reaction or a vitamin deficiency; Ménière's disease and cancer. Such methods involve administering to a mammal in need of such treatment a prophylactically or therapeutically effective amount of one or more such compounds, which inhibit or reduce expression or activity of at least one such gene.

BRIEF DESCRIPTION OF THE FIGURES

FIG. 4B: Skov 3 extract). EGFP_1 S2043, EGFP_1 S2044, and EGFP_1_S1911 S1911 share the same sense strand. The shared sense strand included unmodified ribonucleotides in positions 1, 3, 5, 7, 9, 11, 13, 15, 17, and 19 (5'>3') and 2'-OMethyl sugar modified ribonucleotides in positions 2, 4, 6, 8, 10, 12, 14, 16 and 18. EGFP_1_S2043 antisense strand included unmodified ribonucleotides in positions (5'>3') 2, 4, 6, 8, 10, 12, 14 and 16; 2'-OMethyl sugar modified ribonucleotides in positions 3, 5, 7, 9, 11, 13, 15, 17 and 19 and an adenosine (standard DNA) in position 1; EGFP_1_S2044 is identical to EGFP_1_S2043 except for the presence of a riboadenosine in position 1 of the antisense strand; EGFP_1_S1911 is identical to EGFP_1_S2043 and EGFP_1_S2044 except for the presence of a PT deoxyadenosine nucleotide analogue in position 1 of the antisense strand. FIGS. 4A and 4B show the increased cell extract stability of the antisense strand with deoxypyrazolotriazine nucleotide analogue in position 1 compared to antisense strand with DNA or RNA moiety in position 1 of the antisense strand.

Figure 1A:
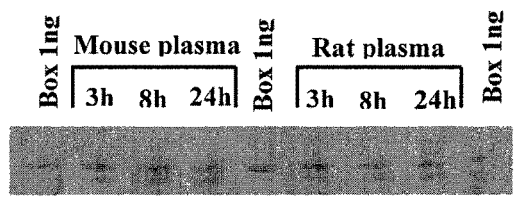
FIGS. 1A and 1B show increased plasma stability (in hours) of the dsRNA molecules in mouse and rat plasma, of dsRNA molecules with deoxyriboadenosine PT moiety at position 18 in the sense strand (EGFP_1_S1913), or riboadenosine PT moiety at position 18 in the sense strand (EGFP_1_S2141) compared to dsRNA molecule with unmodified riboadenosine at position 18 in the sense strand (EGFP_1_S1957), deoxyriboadenosine at position 18 in the sense strand (EGFP_1_S1992) or 2'-OMethyl (2'-OMe) sugar modified riboadenosine at position 18 in the sense strand (EGFP_1_S500). Stability of chemically modified EGFP dsRNA in mouse and rat plasma: detection of the sense strand by 15% denaturing PAGE. EGFP_1_S500, EGFP_1_S1957, EGFP_1_S1913, EGFP_1_S2141 and EGFP_1 S1992 share the same antisense strand. The shared antisense strand included 2'-OMethyl sugar modified ribonucleotides in positions 1, 3, 5, 7, 9, 11, 13, 15, 17, and 19 (5'>3') and unmodified ribonucleotides in positions 2, 4, 6, 8, 10, 12, 14, 16 and 18. EGFP_1 S500 sense strand included unmodified ribonucleotides in positions (5'>3') 1, 3, 5, 7, 9, 11, 13, 15, 17, 19 and 2'-OMethyl sugar modified ribonucleotides in positions 2, 4, 6, 8, 10, 12, 14, 16 and 18; EGFP_1_S1957 sense strand includes unmodified ribonucleotides in positions (5'>3') 1, 3, 5, 7, 9, 11, 13, 15, 17, 18 and 19 (unmodified riboadenosine in position 18) and 2'-OMethyl sugar modified ribonucleotides in positions 2, 4, 6, 8, 10, 12, 14, and 16; EGFP_1 S1913 sense strand included unmodified ribonucleotides in positions (5'>3') 1, 3, 5, 7, 9, 11, 13, 15, 17 and 19, 2'-OMethyl sugar modified ribonucleotides in positions 2, 4, 6, 8, 10, 12, 14 and 16 and a PT deoxyadenosine (PT dA) in position 18; EGFP_1_S2141 sense strand included unmodified ribonucleotides in positions (5'>3') 1, 3, 5, 7, 9, 11, 13, 15, 17 and 19, 2'-OMethyl sugar modified ribonucleotides in positions 2, 4, 6, 8, 10, 12, 14 and 16 and a PT riboadenosine (PT rA) in position 18. EGFP_1_S1992 sense strand included unmodified ribonucleotides in positions (5'>3') 1, 3, 5, 7, 9, 11, 13, 15, 17 and 19, 2'OMe sugar modified ribonucleotides in positions 2, 4, 6, 8, 10, 12, 14 and 16 and a standard unmodified deoxyadenosine (dA) in position 18.
Figure 1A:
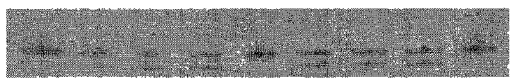
Figure 1A:
Figure 1A:

The compounds, methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

DETAILED DESCRIPTION OF THE INVENTION

Disclosed herein are double-stranded nucleic acid molecules which include at least one pyrazolotriazine (PT) nucleotide analogue which modulate expression of target genes, particularly small interfering RNAs (siRNA), specifically modified dsRNA molecules and the use of these modified dsRNA molecules in preparation of pharmaceutical compositions and in treatment of a subject suffering from various medical conditions. The double-stranded ribonucleic acid molecules disclosed herein exhibit one or more of increased on-target activity, decreased off-target activity, increased nuclease stability (exonuclease and/or endonuclease), and reduced immunogenicity when compared to an unmodified or similarly double-stranded ribonucleic acid compound. The double-stranded ribonucleic acid molecules include positional modifications, which include the presence of at least one pyrazolotriazine (PT) adenosine nucleotide analogue or pyrazolotriazine (PT) guanosine nucleotide analogue, on the sense strand, on the antisense strand or on both the sense strand and the antisense strand thereby imparting on the molecules beneficial properties including one or more of increased knock down activity of target gene expression, reduced level of target protein, increased stability to endo- and/or exonucleases, reduced off-target effects and/or reduced immunomodulating effects compared to an unmodified or similarly modified molecule which excludes the PT nucleotide analogue.

The double-stranded ribonucleic acid molecules disclosed herein are administered as the compound per se (i.e. as naked dsRNA) or as pharmaceutically acceptable salt and are administered alone or as an active ingredient in a pharmaceutical composition. The double-stranded ribonucleic acid molecules, pharmaceutically acceptable salts thereof and compositions comprising the double-stranded ribonucleic acid molecules or pharmaceutically acceptable salts thereof are able to down-regulate, knock down, attenuate, reduce or inhibit target gene expression and/or reduce associated protein level and are useful in the treatment of subjects suffering from diseases or conditions and/or symptoms associated with such diseases or conditions or at risk of contracting diseases or conditions in which target gene expression and/or increase in an associated protein level has adverse consequences.

Accordingly, in certain aspects modified dsRNA molecules and pharmaceutical compositions comprising same useful in down regulating target gene expression are provided herein. As used herein, a target gene is a mammalian gene or a non-mammalian gene.

Definitions

It is to be noted that, as used herein, the singular forms "a", "an" and "the" include plural forms unless the content clearly dictates otherwise. Where aspects or embodiments of the invention are described in terms of Markush groups or other grouping of alternatives, those skilled in the art will recognize that the invention is also thereby described in terms of any individual member or subgroup of members of the group.

A "compound' and a "molecule" are used interchangeably herein when referring to the dsRNA.

The term "inhibit" as used herein refers to reducing the expression of a gene or the activity of the product of such gene to an extent sufficient to achieve a desired biological or physiological effect Inhibition is either complete or partial A "siNA inhibitor" "dsRNA inhibitor" "dsRNA molecule" is a compound which is capable of reducing the expression of a gene or the activity of the product of such gene to an extent sufficient to achieve a desired biological or physiological effect. The term "siNA inhibitor" as used herein refers to one or more of a siRNA, shRNA, synthetic shRNA; miRNA. Inhibition may also be referred to as down-regulation or, for RNAi, silencing. The dsRNA molecule includes a sense strand, also known as a passenger strand, which shares homology to a target RNA; and an antisense strand, also known as a guide strand, which is fully or partially complementary to the sense strand.

As used herein, the term "inhibition" of a target gene or "down regulation of gene expression" means inhibition of gene expression (transcription or translation) or polypeptide activity. The polynucleotide sequence of the target RNA sequence, refers to a mRNA target, a RNA target or any homologous sequences thereof preferably having at least 70% identity, more preferably 80% identity, even more preferably 90% or 95% identity to the target mRNA or RNA. Therefore, polynucleotide sequences, which have undergone mutations, alterations or modifications as described herein are encompassed herein. The terms "mRNA polynucleotide sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogues of either RNA or DNA made from nucleotide analogues. Throughout this disclosure, mRNA sequences are set forth as representing the corresponding genes.

"Oligonucleotide" or "oligomer" refers to a ribonucleotide sequence from about 2 to about 50 nucleotides. Each RNA nucleotide may be independently natural or synthetic, and/or modified or unmodified. Modifications include changes to the sugar moiety, the base moiety and/or the linkages between nucleotides in the oligonucleotide. An oligonucleotide or oligomer as used herein may be a chimera of RNA and DNA.

As used herein, the term "dsRNA" encompasses molecules in which up to 20 ribonucleotides, such as 1, 2, 3, 4, 5, 6, 7, 8, 9, 10, 11, 12, 13, 14, 15, 16, 17, 18, 19 or 20 ribonucleotides, have been substituted with unconventional moieties, including DNA, 2'5' linked ribonucleotides and 2'5' linked deoxyribonucleotides. Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

"Nucleotide" is meant to encompass deoxyribonucleotides and ribonucleotides, which may be natural or synthetic and modified or unmodified. Nucleotides include known nucleotide analogues, which are synthetic, naturally occurring, and non-naturally occurring. Examples of such analogues include, without limitation, phosphorothioates, phosphoramidites, methyl phosphonates, chiral-methyl phosphonates, 2'-O-methyl (2'-OMe) sugar modified ribonucleotides, and peptide-nucleic acids (PNAs). Modifications include changes to the sugar moiety, the base moiety and/or the linkages between ribonucleotides in the oligoribonucleotide. As used herein, the term "ribonucleotide" encompasses natural and synthetic, unmodified and modified ribonucleotides and ribonucleotide analogues which are synthetic, naturally occurring, and non-naturally occurring. Modifications include changes to the sugar moiety, to the base moiety and/or to the linkages between ribonucleotides in the oligonucleotide.

The terms "deoxyribonucleotide" and "deoxynucleotide" are used interchangeably.

The double-stranded ribonucleic acid molecules disclosed herein include at least one pyrazolotriazine (PT) nucleotide analogue substituting a purine nucleotide (adenosine or guanosine) in the sense strand, in the antisense strand or in both the sense strand and antisense strand. In preferred embodiments the double-stranded nucleic acid includes at least one PT nucleotide analogue of general formula II:

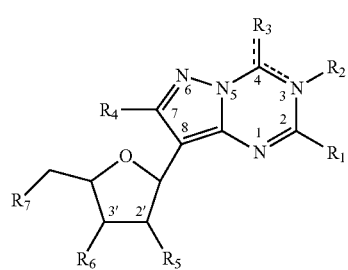

wherein $R_1$ and $R_4$ each independently is selected from H, halogen, —CN, —SCN, —NO$_2$, —O-hydrocarbyl, —S-hydrocarbyl, —CO—H, —CO-hydrocarbyl, —NR$_8$R$_9$, heteroaryl, or hydrocarbyl optionally substituted by one or more groups each independently a halogen, —CN, —SCN, or —NO$_2$, wherein $R_8$ and $R_9$ each independently is H or hydrocarbyl, or $R_8$ and $R_9$ together with the nitrogen atom to which they are attached form a saturated or unsaturated heterocyclic ring optionally containing 1-2 further heteroatoms selected from oxygen, nitrogen or sulfur;

$R_2$ is H or absent;

$R_3$ is O or —NR$_{10}$R$_{10'}$, wherein $R_{10}$ and $R_{10'}$ are each independently H, hydrocarbyl or —CO— hydrocarbyl;

$R_5$ is H, halogen, —O$^-$, or —OR$_{11}$;

$R_6$ is —O$^-$, or —OR$_{11}$;

$R_7$ is OR$_{11}$, a monophosphate moiety or a phosphate linking moiety;

each $R_{11}$ independently is H, $(C_1-C_8)$alkyl, $(C_1-C_8)$alkylene-OR$_{12}$, $(C_1-C_8)$alkylene-SR$_{12}$, or $(C_1-C_8)$alkylene-NR$_{12}$R$_{13}$, wherein $R_{12}$ and $R_{13}$ each independently is H or $(C_1-C_8)$ alkyl; and the dotted line represents a potential double bond between the carbon atom at position 4 and either the nitrogen atom at position 3 or the radical R$_3$, provided that, when R$_2$ is H, there is a double bond between the carbon atom at position 4 and R$_3$, and when R$_2$ is absent, there is a double bond between the carbon atom at position 4 and the nitrogen atom at position 3.

"Adenine PT nucleotide analogue" or "PT adenine analogue" refer to a nucleotide in which the adenine base has been replaced with a pyrazolotriazine base as described herein, and is meant to encompass adenosine (in which the ribose sugar may be unmodified at the 2' position, i.e. 2'OH or modified at the 2' position, e.g. 2'OCH$_3$, 2'MOE and the like) and deoxyadenosine (in which the 2' position of the ribose sugar may be unmodified, i.e. 2'H or modified, e.g. 2'F and the like) pyrazolotriazine nucleotide analogues.

"Guanine PT nucleotide analogue" or "PT guanine analogue" refer to a nucleotide in which the guanine base has been replaced with a pyrazolotriazine base as described herein, and is meant to encompass guanosine (in which the ribose sugar may be unmodified at the 2' position, i.e. 2'OH or modified at the 2' position, e.g. 2'OCH$_3$, 2'MOE and the like) and deoxyguanosine (in which the 2' position of the ribose sugar may be unmodified, i.e. 2'H or modified, e.g. 2'F and the like) pyrazolotriazine nucleotide analogues.

As used herein, the term "halogen" includes fluoro, chloro, bromo, and iodo, and is preferably fluoro, chloro or bromo.

The term "hydrocarbyl" in any of the definitions of the different radicals $R_1$, $R_3$ and $R_4$ refers to a radical containing only carbon and hydrogen atoms that may be saturated or unsaturated, linear or branched, cyclic or acyclic, or aromatic, and includes $(C_1-C_8)$alkyl, $(C_2-C_8)$alkenyl, $(C_2-C_8)$ alkynyl, $(C_3-C_{10})$cyclo alkyl, $(C_3-C_{10})$cyclo alkenyl, $(C_6-C_{14})$aryl, $(C_1-C_8)$alkyl$(C_6-C_{14})$aryl, and $(C_6-C_{14})$aryl$(C_1-C_8)$alkyl.

The term "$(C_1-C_8)$alkyl" typically means a straight or branched hydrocarbon radical having 1-8 carbon atoms and includes, e.g., methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like. Preferred are $(C_1-C_4)$alkyl groups, most preferably methyl and ethyl. The terms "$(C_2-C_8)$alkenyl" and "$(C_2-C_8)$alkynyl" typically mean straight and branched hydrocarbon radicals having 2-8 carbon atoms and 1 double or triple bond, respectively, and include ethenyl, 3-buten-1-yl, 2-ethenylbutyl, 3-octen-1-yl, and the like, and propynyl, 2-butyn-1-yl, 3-pentyn-1-yl, and the like. $(C_2-C_6)$alkenyl and alkynyl radicals are preferred, more preferably $(C_2-C_4)$alkenyl and alkynyl.

The term "$(C_1-C_8)$alkylene" typically means a divalent straight or branched hydrocarbon radical having 1-8 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, and the like. Preferred are $(C_1-C_4)$alkylene, more preferably $(C_1-C_2)$alkylene.

The term "$(C_3-C_{10})$cycloalkyl" as used herein means a mono- or bicyclic saturated hydrocarbyl group having 3-10 carbon atoms such as cyclopropyl, cyclobutyl, cyclopentyl, cyclohexyl, cycloheptyl, cyclooctyl, adamantyl, bicyclo[3.2.1]octyl, bicyclo[2.2.1]heptyl, and the like, that may be substituted, e.g., by one or more $(C_1-C_8)$alkyl groups.

The term "$(C_3-C_{10})$cycloalkenyl" as used herein means a mono- or bicyclic hydrocarbyl group having 3-10 carbon atoms and one double bond such as cyclopropenyl, cyclobutenyl, cyclopentenyl, cyclohexenyl, cycloheptenyl, cyclooctenyl,1,2,3,3a,4,5-hexahydropentalenyl, 1,2,3,3a,4,6a-hexahydropentalenyl, 2,3,3a,4,5,6-hexahydro-1H-indenyl, 2,3,3a,4,5,7a-hexahydro-1H-indenyl, 2,3,3a,4,7,7a-hexahydro-1H-indenyl, 3a,4,5,6,7,7a-hexahydro-1H-indenyl, 1,2,3,4,4a,5,6,8a-octahydronaphthalenyl, 1,2,3,4,4a,5,8,8a-octahydronaphthalenyl, and the like, that may be substituted, e.g., by one or more $(C_1-C_8)$alkyl groups.

The term "$(C_6-C_{14})$aryl" denotes an aromatic carbocyclic group having 6-14 carbon atoms consisting of a single ring or multiple rings either condensed or linked by a covalent bond such as, but not limited to, phenyl, naphthyl, phenanthryl, and biphenyl. The aryl radical may optionally be substituted by one or more groups each independently selected from halogen, e.g., F, Cl, Br or I, $(C_1-C_8)$alkyl, —O—$(C_1-C_8)$alkyl, —COO$(C_1-C_8)$alkyl, —CN, or NO$_2$.

The term "$(C_6-C_{14})$aryl$(C_1-C_8)$alkyl" denotes an arylalkyl radical such as benzyl, phenethyl and the like, and the term "$(C_1-C_8)$alkyl$(C_6-C_{14})$aryl" denotes an alkylaryl radical such as methylphenyl, ethylphenyl, xylyl, and the like.

The term "heteroaryl" refers to a radical derived from a mono- or poly-cyclic heteroaromatic ring containing one to three, preferably 1-2, heteroatoms selected from N, O or S. When the heteroaryl is a monocyclic ring, it is preferably a radical of a 5-6-membered ring such as, but not limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-a]pyridyl, benzimidazolyl, benzthiazolyl, benzoxazolyl, pyrido[1,2-a]pyrimidinyl and 1,3-benzodioxinyl. The heteroaryl may be substituted. It is to be understood that when a polycyclic heteroaryl is substituted, the substitution may be in any of the carbocyclic and/or heterocyclic rings.

In certain embodiments, the PT nucleotide analogue disclosed herein is a compound of the general formula II as defined above, wherein $R_1$ and $R_4$ each independently is H, halogen, —CN, —SCN, —NO2, —O-hydrocarbyl, —S-hydrocarbyl, —CO—H, —CO-hydrocarbyl, —NR$_8$R$_9$, heteroaryl, or hydrocarbyl; $R_8$ and $R_9$ each independently is H or hydrocarbyl; and said hydrocarbyl each independently is $(C_1-C_8)$alkyl, preferably $(C_1-C_4)$alkyl, more preferably methyl or ethyl. In particular embodiments, $R_1$ and $R_4$ each independently is H, halogen, —O— hydrocarbyl, —S- hydrocarbyl, —CO—H, —CO-hydrocarbyl, —NR$_8$R$_9$, or hydrocarbyl; R$_8$ and R$_9$ each independently is H or hydrocarbyl; and said hydrocarbyl each independently is (C$_1$-C$_4$) alkyl, preferably methyl or ethyl.

In certain embodiments, the PT nucleotide analogue disclosed herein is a compound of the general formula II as defined above, wherein R$_3$ is O or —NR$_{10}$R$_{10'}$; wherein R$_{10}$ and R$_{10'}$ are each independently H, hydrocarbyl or —CO-hydrocarbyl; and said hydrocarbyl is (C$_1$-C$_8$)alkyl, preferably (C$_1$-C$_4$)alkyl, most preferably methyl or ethyl. Preferably at least one of R$_{10}$ or R$_{10'}$ is H.

In certain embodiments, the PT nucleotide analogue disclosed herein is a compound of the general formula II as defined above, wherein R$_5$ is H, halogen, or —OR$_{11}$; and R$_{11}$ is H, (C$_1$-C$_4$)alkyl, preferably (C$_1$-C$_2$)alkyl, (C$_1$-C$_4$)alkylene-O R$_{12}$, preferably (C$_1$-C$_2$)alkylene-OR$_{12}$, (C$_1$-C$_4$)alkylene-SR$_{12}$, preferably (C$_1$-C$_2$)alkylene-SR$_{12}$, (C$_1$-C$_4$)alkylene-NR$_{12}$R$_{13}$, preferably (C$_1$-C$_2$)alkylene-NR$_{12}$R$_{13}$, wherein R$_{12}$ and R$_{13}$ each independently is H or (C$_1$-C$_4$) alkyl, preferably (C$_1$-C$_2$)alkyl. In particular such embodiments, R$_5$ is H, halogen, or —OR$_{11}$; and R$_{11}$ is H, (C$_1$-C$_2$) alkyl, (C$_1$-C$_2$)alkylene-OH, (C$_1$-C$_2$)alkylene-SH, or (C$_1$-C$_2$) alkylene-NH$_2$.

In certain embodiments, the PT nucleotide analogue disclosed herein is a compound of the general formula II as defined above, wherein R$_6$ is —O$^-$ or —OR$_{11}$; and R$_{11}$ is H, (C$_1$-C$_4$)alkyl, preferably (C$_1$-C$_2$)alkyl, (C$_1$-C$_4$)alkylene-OR$_{12}$, preferably (C$_1$-C$_2$)alkylene-OR$_{12}$, (C$_1$-C$_4$)alkylene-SR$_{12}$, preferably (C$_1$-C$_2$)alkylene-SR$_{12}$, or (C$_1$-C$_4$)alkylene-NR$_{12}$R$_{13}$, preferably (C$_1$-C$_2$)alkylene-NR$_{12}$R$_{13}$, wherein R$_{12}$ and R$_{13}$ each independently is H or (C$_1$-C$_4$)alkyl, preferably (C$_1$-C$_2$)alkyl. In particular such embodiments, R$_6$ is —O$^-$ or —OR$_{11}$; and R$_{11}$ is H, (C$_1$-C$_2$)alkyl, (C$_1$-C$_2$)alkylene-OH, (C$_1$-C$_2$)alkylene-SH, or (C$_1$-C$_2$)alkylene-NH$_2$.

In particular embodiments, the PT nucleotide analogue disclosed herein is a compound of the general formula II as defined above, wherein R$_1$ and R$_4$ each independently is H, halogen, (C$_1$-C$_4$)alkyl, —O—(C$_1$-C$_4$)alkyl, —S—(C$_1$-C$_4$) alkyl, —CO—H, —CO—(C$_1$-C$_4$)alkyl, or —NR$_8$R$_9$, wherein R$_8$ and R$_9$ each independently is H or (C$_1$-C$_4$)alkyl; R$_3$ is O or —NHR$_{10}$, wherein R$_{10}$ is H, (C$_1$-C$_4$)alkyl, or —CO—(C$_1$-C$_4$)alkyl; R$_5$ is H, halogen, or —OR$_{11}$, wherein R$_{11}$ is H, (C$_1$-C$_2$)alkyl, (C$_1$-C$_2$)alkylene-OH, (C$_1$-C$_2$)alkylene-SH, or (C$_1$-C$_2$)alkylene-NH$_2$; and R$_6$ is —O$^-$ or —OR$_{11}$, wherein R$_{11}$ is H, (C$_1$-C$_2$)alkyl, (C$_1$-C$_2$)alkylene-OH, (C$_1$-C$_2$)alkylene-SH, or (C$_1$-C$_2$)alkylene-NH$_2$ In more particular embodiments, R$_1$ and R$_4$ each independently is H, halogen, (C$_1$-C$_2$)alkyl, —O—(C$_1$-C$_2$)alkyl, —S—(C$_1$-C$_2$) alkyl, —CO—H, —CO—(C$_1$-C$_2$)alkyl, or —NR$_8$R$_9$, wherein R$_8$ and R$_9$ each independently is H or (C$_1$-C$_2$)alkyl; and R$_3$ is O or —NHR$_{10}$, wherein R$_{10}$ is H, (C$_1$-C$_2$)alkyl or —CO—(C$_1$-C$_2$)alkyl.

The term "amine protecting group" as used herein refers to a chemical moiety that can readily be attached to an amine group (forming a protected amine) added to protect said amine group from undesired chemical reactions and then at a later point removed to reveal the original amine group. Examples of amine protecting groups can be found in references such as Green and Wuts (1991, Protective Groups in Organic Synthesis, Wiley, New York, 2nd Edition) and Bodansky (1993, Principles of Peptide Synthesis, Springer, Berlin). Examples of amine protecting groups include, without being limited to, acetyl, benzoyl, carbobenzyloxy, p-methoxybenzyl carbonyl, methoxycarbonyl, tert-butyloxycarbonyl, 9-fluorenylmethyloxycarbonyl (FMOC), benzyl, a carbamate group, p-methoxybenzyl, 3,4-dimethoxybenzyl (DMPM), p-methoxyphenyl (PMP), monomethoxytrityl (MMT), dimethoxytrityl (DMT), and tosyl.

The term "hydroxyl protecting group", also termed "alcohol protecting group", refers to a chemical moiety that can readily be attached to an hydroxyl group (and forming a protected hydroxy) when desired to protect said hydroxyl from undesired chemical reactions and then at a later point be removed from said protected hydroxyl to reveal the original hydroxyl group. Examples of hydroxy protecting groups are well known in the art and can be found in references such as Green and Wuts (1991, Protective Groups in Organic Synthesis, Wiley, New York, 2nd Edition) and Bodansky (1993, Principles of Peptide Synthesis, Springer, Berlin). Non-limiting examples of hydroxyl protecting groups include DMT, tert-butyldimethylsilyl (TBDMS), tri-iso-propylsilyloxymethyl (TOM), trimethylsilyl (TMS), tri-isopropylsilyl (TIPS), acetyl, benzyl, and benzoyl.

The term "phosphate moiety" as used herein refers to a monophosphate moiety of the general formula —[O—P(O)(R)—O]$^{2-}$, a diphosphate moiety of the general formula —[O—P(O)(R)—O—P(O)(R)—O]$^{3-}$, or a triphosphate moiety of the general formula —[O—P(O)(R)—O—P(O) (R)—O—P(O)(R)—O]$^{4-}$, wherein R' each independently is O$^-$, S$^-$, BH$_3^-$, or N$^-$, preferably to such mono-, di- and tri-phosphate moieties wherein (i) R' each is O$^-$; or (ii) one of the R's, preferably the R' linked to the phosphate atom at position α, is S$^-$ or BH$_3^-$, and the other R's are O$^-$, as well as to any protonated form thereof. Preferred are monophosphate moieties as defined above, such as —[O—PO$_3$]$^{2-}$, —[O—PO$_2$S]$^{2-}$, and [O—PO$_2$(BH$_3$)]$^{2-}$, more preferably —[O—PO$_3$]$^{2-}$.

The term "phosphate linking moiety" as used herein refers to a moiety of the general formula —[O—P(O)(R)]$^-$—, wherein R' is O$^-$, S$^-$, BH$_3^-$, or N$^-$, preferably O$^-$, S$^-$, or BH$_3^-$, more preferably O$^-$, as well as to a protonated form thereof.

In preferred embodiments the PT nucleotide analogue comprises an adenine PT nucleotide analogue of formula IIa, or a guanine PT nucleotide analogue of formula IIb, as follows:

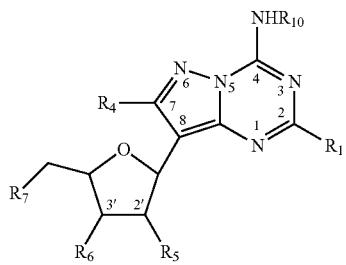

IIa

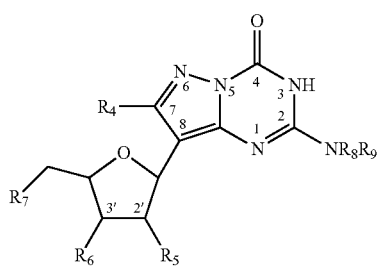

IIb

In some preferred embodiments the pyrazolotriazine (PT) nucleotide analogue is an adenosine PT nucleotide analogue of formula IIa wherein $R_1$ is H, $R_{10}$ is H; $R_4$ is H; $R_5$ is —$OR_{11}$, wherein $R_{11}$ is H, ($C_1$-$C_8$)alkyl, ($C_1$-$C_8$)alkylene-$OR_{12}$, ($C_1$-$C_8$)alkylene-$SR_{12}$, or ($C_1$-$C_8$)alkylene-$NR_{12}R_{13}$, wherein $R_{12}$ and $R_{13}$ each is independently H or ($C_1$-$C_8$) alkyl; $R_6$ is —O⁻ or —OH; and $R_7$OH or a phosphate moiety. In some embodiments $R_{11}$ is H, $CH_3$ or $(CH_2)_2$—$OCH_3$. In some embodiments $R_{11}$ is H (i.e. $R_5$ is hydroxy; 2'OH). In some embodiments $R_{11}$ is $CH_3$ (i.e. $R_5$ is methoxy, 2'OMe). In some embodiments $R_{11}$ is $(CH_2)_2$—$OCH_3$ (i.e. $R_5$ is methoxyethoxy; 2'MOE). Preferably $R_7$ is a phosphate moiety linking the PT analogue to an adjacent nucleotide in an oligonucleotide (i.e. sense strand or antisense strand of a dsRNA molecule). Alternatively, $R_7$ is an OH when the PT analogue is at the 5' terminal position of an oligonucleotide (i.e. sense strand or antisense strand of a dsRNA molecule).

In some preferred embodiments the pyrazolotriazine (PT) nucleotide analogue is a deoxyadenosine PT nucleotide analogue of formula IIa wherein $R_1$ is H, $R_{10}$ is H; $R_4$ is H; $R_5$ is H or halogen; $R_6$ is —O⁻ or —OH; and $R_7$ is OH or a phosphate moiety. In some embodiments $R_5$ is H. In some embodiments $R_5$ is halogen, preferably F.

In some preferred embodiments the pyrazolotriazine (PT) nucleotide analogue is a guanosine PT nucleotide analogue of formula IIb wherein each of $R_4$, $R_8$ and $R_9$ is H, $R_5$ is —$OR_{11}$, wherein $R_{11}$ is H, ($C_1$-$C_8$)alkyl, ($C_1$-$C_8$)alkylene-$OR_{12}$, ($C_1$-$C_8$)alkylene-$SR_{12}$, or ($C_1$-$C_8$)alkylene-$NR_{12}R_{13}$, wherein $R_{12}$ and $R_{13}$ each is independently H or ($C_1$-$C_8$) alkyl; $R_6$ is —O⁻ or —OH; and $R_7$ is OH or a phosphate moiety. In some embodiments $R_{11}$ is H, $CH_3$ or $(CH_2)_2$—$OCH_3$. In some embodiments $R_{11}$ is H (i.e. $R_5$ is hydroxy; 2'OH). In some embodiments $R_{11}$ is $CH_3$ (i.e. $R_5$ is methoxy, 2'OMe). In some embodiments $R_{11}$ is $(CH_2)_2$—$OCH_3$ (i.e. $R_5$ is methoxyethoxy; 2'MOE).

In some preferred embodiments the pyrazolotriazine (PT) nucleotide analogue is a deoxyguanosine PT nucleotide analogue of formula IIb wherein each of $R_4$, $R_8$ and $R_9$ is H, $R_5$ is H or halogen; $R_6$ is —O⁻ or —OH; and $R_7$ is OH or a phosphate moiety. In some embodiments $R_5$ is H. In some embodiments $R_5$ is halogen, preferably F.

In some embodiments the dsRNA molecule includes at least one adenine PT nucleotide analogue selected from one of adenosine or deoxyadenosine PT nucleotide analogues set forth in Table 2 as compounds 3-32. In certain embodiments, the nucleotide analogue disclosed herein is an adenine analogue of the general formula IIa as defined above, wherein $R_1$ and $R_4$ each independently is H, halogen, ($C_1$-$C_2$)alkyl, —O—($C_1$-$C_2$)alkyl, —S—($C_1$-$C_2$)alkyl, —CO—H, —CO—($C_1$-$C_2$)alkyl, or —$NR_8R_9$, wherein $R_8$ and $R_9$ each independently is H or ($C_1$-$C_2$)alkyl, preferably H; $R_2$ is absent; $R_3$ is —$NH_2$; $R_5$ is H, halogen, —O⁻ or —$OR_{11}$; $R_6$ is —O⁻, or —$OR_{11}$; $R_7$ is —$OR_{11}$, a phosphate moiety or a phosphate linking moiety; and $R_{11}$ each independently is H, ($C_1$-$C_4$)alkyl, ($C_1$-$C_4$)alkylene-OH, ($C_1$-$C_4$)alkylene-$OCH_3$, ($C_1$-$C_4$)alkylene-SH, ($C_1$-$C_4$)alkylene-$SCH_3$, or ($C_1$-$C_4$)alkylene-$NH_2$. The full chemical structures of such adenine PT nucleotide analogue described in the specification are depicted in Table 2, hereinafter.

In specific embodiments, the dsRNA molecule includes at least one PT deoxyadenosine analogue of the general formula IIa, wherein (i) $R_1$ and $R_4$ are H; $R_2$ is absent; $R_3$ is —$NHR_{19}$; $R_5$ is H; $R_6$ is —O⁻; $R_7$ is —OH; and $R_{10}$ is H or benzoyl (compounds 3 and 4, respectively); (ii) $R_1$ and $R_4$ are H; $R_2$ is absent; $R_3$ is —$NHR_{19}$; $R_5$ is H; $R_6$ is —OH; $R_7$ is —[O—$PO_3$]²⁻, —[O—$PO_2$S]², or [O—$PO_2(BH_3)$]²⁻; and $R_{10}$ is H or benzoyl (compounds 5, 5a, 5b, or 6, 6a and 6b, respectively); (iii) $R_1$ and $R_4$ are H; $R_2$ is absent; $R_3$ is —$NHR_{19}$; $R_5$ is H; $R_6$ is —O⁻, $R_7$ is —[O—$PO_3$]²⁻, —[O—$PO_2$S]², or [O—$PO_2(BH_3)$]²⁻; and $R_{10}$ is H or benzoyl (compounds 7, 7a, 7b, or 8, 8a, and 8b respectively)

In specific embodiments, the dsRNA molecule includes at last one adenosine analogue of the general formula IIa, wherein (iv) $R_1$ and $R_4$ are H; $R_2$ is absent; $R_3$ is —$NHR_{10}$; $R_5$ is —OH; $R_6$ is —O—; $R_7$ is —OH; and $R_{10}$ is H or benzoyl (compounds 9 and 10, respectively); (v) $R_1$ and $R_4$ are H; $R_2$ is absent; $R_3$ is —$NHR_{10}$; $R_5$ is —OH; $R_6$ is —OH; $R_7$ is —[O—$PO_3$]²⁻, —[O—$PO_2$S]²⁻, or [O—$PO_2(BH_3)$]²⁻; and $R_{10}$ is H or benzoyl (compounds 11, 11a, 11b, or 12, 12a and 12b, respectively); (vi) $R_1$ and $R_4$ are H; $R_2$ is absent; $R_3$ is —$NHR_{19}$; $R_5$ is —OH; $R_6$ is —O⁻, $R_7$ is —[O—$PO_3$]²⁻, —[O—$PO_2$S]²⁻, or —[O—$PO_2(BH_3)$]²⁻; and $R_{10}$ is H or benzoyl (compounds 13, 13a, 13b, or 14, 14a and 14b, respectively);

In specific embodiments, the dsRNA molecule includes at least one adenosine analogue of the general formula IIa, wherein (vii) $R_1$ and $R_4$ are H; $R_2$ is absent; $R_3$ is —$NHR_{10}$; $R_5$ is —$OCH_3$; $R_6$ is —O—; $R_7$ is —OH; and $R_{10}$ is H or benzoyl (compounds 14 and 16, respectively); (viii) $R_1$ and $R_4$ are H; $R_2$ is absent; $R_3$ is —$NHR_{10}$; $R_5$ is —$OCH_3$; $R_6$ is —OH; $R_7$ is —[O—$PO_3$]²⁻, —[O—$PO_2$S]²⁻, or —[O—$PO_2(BH_3)$]²⁻; and $R_{10}$ is H or benzoyl (compounds 17, 17a, 17b, or 18, 18a and 18b, respectively); (ix) $R_1$ and $R_4$ are H; $R_2$ is absent; $R_3$ is —$NHR_{10}$; $R_5$ is —$OCH_3$; $R_6$ is —O⁻, $R_7$ is —[O—$PO_3$]²⁻, —[O—$PO_2$S]²⁻, or —[O—$PO_2(BH_3)$]²⁻; and $R_{10}$ is H or benzoyl (compounds 19, 19a, 19b, or 20, 20a and 20b, respectively);

In specific embodiments, the dsRNA molecule includes at least one adenosine analogue of the general formula IIa, wherein (x) $R_1$ and $R_4$ are H; $R_2$ is absent; $R_3$ is —$NHR_{10}$; $R_5$ is $O(CH_2)_2OCH_3$; $R_6$ is —O—; $R_7$ is —OH; and $R_{10}$ is H or benzoyl (compounds 21 and 22, respectively); (xi) $R_1$ and $R_4$ are H; $R_2$ is absent; $R_3$ is —$NHR_{10}$; $R_5$ is $O(CH_2)_2OCH_3$; $R_6$ is —OH; $R_7$ is —[O—$PO_3$]²⁻, —[O—$PO_2$S]²⁻, or [O—$PO_2(BH_3)$]²⁻; and $R_{10}$ is H or benzoyl (compounds 23, 23a, 23b, or 24, 24a and 24b, respectively); (xii) $R_1$ and $R_4$ are H; $R_2$ is absent; $R_3$ is —$NHR_{10}$; $R_5$ is $O(CH_2)_2OCH_3$; $R_6$ is —O⁻, $R_7$ is —[O—$PO_3$]²⁻, —[O—$PO_2$S]²⁻, or [O—$PO_2(BH_3)$]²⁻; and $R_{10}$ is H or benzoyl (compounds 25, 25a, 25b, or 26, 26a and 26b, respectively);

In specific embodiments, the dsRNA molecule includes at least one deoxyadenosine analogue of the general formula IIa, wherein (xiii) $R_1$ and $R_4$ are H; $R_2$ is absent; $R_3$ is —$NHR_{10}$; $R_5$ is F; $R_6$ is —O—; $R_7$ is —OH; and $R_{10}$ is H or benzoyl (compounds 27 and 28, respectively); (xiv) $R_1$ and $R_4$ are H; $R_2$ is absent; $R_3$ is —$NHR_{10}$; $R_5$ is F; $R_6$ is —OH; $R_7$ is —[O—$PO_3$]²⁻, —[O—$PO_2$S]²⁻, or —[O—$PO_2(BH_3)$]²⁻; and $R_{10}$ is H or benzoyl (compounds 29, 29a, 29b, or 30, 30a and 30b, respectively); (xv) $R_1$ and $R_4$ are H; $R_2$ is absent; $R_3$ is —$NHR_{10}$; $R_5$ is F; $R_6$ is —O⁻, $R_7$ is —[O—$PO_3$]²⁻, —[O—$PO_2$S]²⁻, or [O—$PO_2(BH_3)$]²⁻; and $R_{10}$ is H or benzoyl (compounds 31, 31a, 31b or 32, 32a and 32b, respectively).

TABLE 2

Adenosine and deoxyadenosine PT nucleotide analogues identified as compounds 3-32

| 3/4 | 5/6 | 7/8 |
|---|---|---|
| 3 ($R_{10}$ = H)<br>4 ($R_{10}$ = benzoyl) | 5 ($R_{10}$ = H)<br>6 ($R_{10}$ = benzoyl) | 7 ($R_{10}$ = H)<br>8 ($R_{10}$ = benzoyl) |
| 9/10 | 11/12 | 13/14 |
| 9 ($R_{10}$ = H)<br>10 ($R_{10}$ = benzoyl) | 11 ($R_{10}$ = H)<br>12 ($R_{10}$ = benzoyl) | 13 ($R_{10}$ = H)<br>14 ($R_{10}$ = benzoyl) |
| 15/16 | 17/18 | 19/20 |
| 15 ($R_{10}$ = H)<br>16 ($R_{10}$ = benzoyl) | 17 ($R_{10}$ = H)<br>18 ($R_{10}$ = benzoyl) | 19 ($R_{10}$ = H)<br>20 ($R_{10}$ = benzoyl) |
| 21/22 | 23/24 | 25/26 |
| 21 ($R_{10}$ = H)<br>22 ($R_{10}$ = benzoyl) | 23 ($R_{10}$ = H)<br>24 ($R_{10}$ = benzoyl) | 25 ($R_{10}$ = H)<br>26 ($R_{10}$ = benzoyl) |

TABLE 2-continued

Adenosine and deoxyadenosine PT nucleotide analogues identified as compounds 3-32

| 27/28 | 29/30 | 31/32 |
|---|---|---|
| 27 ($R_{10}$ = H) | 29 ($R_{10}$ = H) | 31 ($R_{10}$ = H) |
| 28 ($R_{10}$ = benzoyl) | 30 ($R_{10}$ = benzoyl) | 32 ($R_{10}$ = benzoyl) |

*The —[O—$PO_3$]2- in the above compounds may be substituted with another phosphate moiety, including, for example, a phosphate linking moiety, a triesterphosphorothioate moiety [—[O—$PO_2S$]2-] (a) or —[O—$PO_2(BH_3)$]2- (b). The phosphate linking moiety is —[O—P(O)(R')]—, wherein R' is O—, S—, $BH_3$—, or N—, preferably O—, S—, or $BH_3$—, more preferably O—, as well as to a protonated form thereof.

In some embodiments the dsRNA molecule includes at least one guanine PT nucleotide analogue selected from one of guanosine or deoxyguanosine PT nucleotide analogues set forth in Table 3, as compounds 33-62. In certain embodiments, the nucleoside analogue is a guanine analogue of the general formula IIb as defined above, wherein $R_1$ is —$NHR_9$; $R_2$ is H; $R_3$ is O; $R_4$ is H; $R_9$ is H or benzoyl; $R_5$ is H, halogen, —O⁻ or —$OR_{11}$; $R_6$ is —O⁻, or —$OR_{11}$; $R_7$ is —$OR_{11}$, a phosphate moiety or a phosphate linking moiety; and $R_{11}$ each independently is H, ($C_1$-$C_4$)alkyl, ($C_1$-$C_4$)alkylene-OH, ($C_1$-$C_4$)alkylene-O $CH_3$, ($C_1$-$C_4$)alkylene-SH, ($C_1$-$C_4$)alkylene-$SCH_3$, or ($C_1$-$C_4$)alkylene-$NH_2$. The full chemical structures of specific such guanine PT nucleotide analogues described in the specification are depicted in Table 3 hereinafter.

In specific embodiments, the dsRNA molecule includes at least one deoxyguanosine PT nucleotide analogue of the general formula IIb, wherein (i) $R_1$ is $NHR_9$; $R_2$ and $R_4$ are H; $R_3$ is O; $R_5$ is H; $R_6$ is —O—; $R_7$ is —OH; and $R_9$ is H or benzoyl (compounds 33 and 34, respectively); (ii) $R_1$ is $NHR_9$; $R_2$ and $R_4$ are H; $R_3$ is O; $R_5$ is H; $R_6$ is —OH; $R_7$ is —[O—$PO_3$]—[O—$PO_2S$]²⁻, or [O—$PO_2(BH_3)$]²⁻; and $R_9$ is H or benzoyl (compounds 35, 35a, 35b, 36, or 36a and 36b, respectively); (iii) $R_1$ is $NHR_9$; $R_2$ and $R_4$ are H; $R_3$ is O; $R_5$ is H; $R_6$ is —O⁻, $R_7$ is —[O—$PO_3$]²⁻, —[O—$PO_2S$]²⁻, or —[O—$PO_2(BH_3)$]²⁻; and $R_9$ is H or benzoyl (compounds 37, 37a, 37b, or 38, 38a, and 38b respectively)

In specific embodiments, the dsRNA molecule includes at least one guanosine PT analogue of the general formula IIb, wherein (iv) $R_1$ is $NHR_9$; $R_2$ and $R_4$ are H; $R_3$ is O; $R_5$ is OH; $R_6$ is —O—; $R_7$ is —OH; and $R_9$ is H or benzoyl (compounds 39 and 40, respectively); (v) $R_1$ is $NHR_9$; $R_2$ and $R_4$ are H; $R_3$ is O; $R_5$ is OH; $R_6$ is —OH; $R_7$ is —[O—$PO_3$]²⁻, —[O—$PO_2S$]²⁻, or —[O—$PO_2(BH_3)$]²⁻; and $R_9$ is H or benzoyl (compounds 41, 41a, 41b, or 42, 42a and 42b, respectively); (vi) $R_1$ is $NHR_9$; $R_2$ and $R_4$ are H; $R_3$ is O; $R_5$ is OH; $R_6$ is —O⁻, $R_7$ is —[O—$PO_3$]²⁻, —[O—$PO_2S$]²⁻, or —[O—$PO_2(BH_3)$]²⁻; and $R_9$ is H or benzoyl (compounds 43, 43a, 43b, or 44, 44a, and 44b, respectively);

In specific embodiments, the dsRNA molecule includes at least one guanosine PT analogue of the general formula IIb, wherein (vii) $R_1$ is $NHR_9$; $R_2$ and $R_4$ are H; $R_3$ is O; $R_5$ is $OCH_3$; $R_6$ is —O—; $R_7$ is —OH; and $R_9$ is H or benzoyl (compounds 45 and 46, respectively); (viii) $R_1$ is $NHR_9$; $R_2$ and $R_4$ are H; $R_3$ is O; $R_5$ is $OCH_3$; $R_6$ is —OH; $R_7$ is —[O—$PO_3$]²⁻, —[O—$PO_2S$]²⁻, or —[O—$PO_2(BH_3)$]²⁻; and $R_9$ is H or benzoyl (compounds 47, 47a, 47b, or 48, 48a, and 48b, respectively); (ix) $R_1$ is $NHR_9$; $R_2$ and $R_4$ are H; $R_3$ is O; $R_5$ is $OCH_3$; $R_6$ is —O⁻, $R_7$ is —[O—$PO_3$]²⁻, —[O—$PO_2S$]²⁻, or [O—$PO_2(BH_3)$]²⁻; and $R_9$ is H or benzoyl (compounds 49, 49a, or 50, 50a and 50b, respectively);

In specific embodiments, the dsRNA molecule includes at least one guanosine PT analogue of the general formula IIb, wherein (x) $R_1$ is $NHR_9$; $R_2$ and $R_4$ are H; $R_3$ is O; $R_5$ is $O(CH_2)_2OCH_3$; $R_6$ is —O—; $R_7$ is —OH; and $R_9$ is H or benzoyl (compounds 51 and 52, respectively); (xi) $R_1$ is $NHR_9$; $R_2$ and $R_4$ are H; $R_3$ is O; $R_5$ is $O(CH_2)_2OCH_3$; $R_6$ is —OH; $R_7$ is —[O—$PO_3$]²⁻, —[O—$PO_2S$]²⁻, or [O—$PO_2(BH_3)$]²⁻; and $R_9$ is H or benzoyl (compounds 53, 53a, 53b, or 54, 54a and 54b, respectively); (xii) $R_1$ is $NHR_9$; $R_2$ and $R_4$ are H; $R_3$ is O; $R_5$ is $O(CH_2)_2OCH_3$; $R_6$ is -O⁻, $R_7$ is —[O—$PO_3$]²⁻, —[O—$PO_2S$]²⁻, or —[O—$PO_2(BH_3)$]²⁻; and $R_9$ is H or benzoyl (compounds 55, 55a, 55b, or 56, 56a and 56b, respectively);

In specific embodiments, the dsRNA molecule includes at least one guanosine PT analogue of the general formula IIb, wherein (xiii) $R_1$ is $NHR_9$; $R_2$ and $R_4$ are H; $R_3$ is O; $R_5$ is F; $R_6$ is —O—; $R_7$ is —OH; and $R_9$ is H or benzoyl (compounds 57 and 58, respectively); (xvi) $R_1$ is $NHR_9$; $R_2$ and $R_4$ are H; $R_3$ is O; $R_5$ is F; $R_6$ is —OH; $R_7$ is —[O—$PO_3$]²⁻, —[O—$PO_2S$]²⁻, or —[O—$PO_2(BH_3)$]²⁻; and $R_9$ is H or benzoyl (compounds 59, 59a, 59b, or 60, 60a and 60b, respectively); (xv) $R_1$ is $NHR_9$; $R_2$ and $R_4$ are H; $R_3$ is O; $R_5$ is F; $R_6$ is —O⁻, $R_7$ is —[O—$PO_3$]²⁻, —[O—$PO_2S$]²⁻, or —[O—$PO_2(BH_3)$]²⁻; and $R_9$ is H or benzoyl (compounds 61, 61a, 61c, or 62, 62a and 62b, respectively).

TABLE 3

Guanosine and deoxyguanosine PT nucleotide analogues identified as compounds 33-62

| 33/34 | 35/36 | 37/38 |
|---|---|---|
| 33 (R$_9$ = H)<br>34 (R$_9$ = benzoyl) | 35 (R$_9$ = H)<br>36 (R$_9$ = benzoyl) | 37 (R$_9$ = H)<br>38 (R$_9$ = benzoyl) |
| 39/40 | 41/42 | 43/44 |
| 39 (R$_9$ = H)<br>40 (R$_9$ = benzoyl) | 41 (R$_9$ = H)<br>42 (R$_9$ = benzoyl) | 43 (R$_9$ = H)<br>44 (R$_9$ = benzoyl) |
| 45/46 | 47/48 | 49/50 |
| 45 (R$_9$ = H)<br>46 (R$_9$ = benzoyl) | 47 (R$_9$ = H)<br>48 (R$_9$ = benzoyl) | 49 (R$_9$ = H)<br>50 (R$_9$ = benzoyl) |
| 51/52 | 53/54 | 55/56 |
| 51 (R$_9$ = H)<br>52 (R$_9$ = benzoyl) | 53 (R$_9$ = H)<br>54 (R$_9$ = benzoyl) | 55 (R$_9$ = H)<br>56 (R$_9$ = benzoyl) |

TABLE 3-continued

Guanosine and deoxyguanosine PT nucleotide analogues identified as compounds 33-62

| 57/58 | 59/60 | 61/62 |
|---|---|---|
| 57 ($R_9$ = H)<br>58 ($R_9$ = benzoyl) | 59 ($R_9$ = H)<br>60 ($R_9$ = benzoyl) | 61 ($R_9$ = H)<br>62 ($R_9$ = benzoyl) |

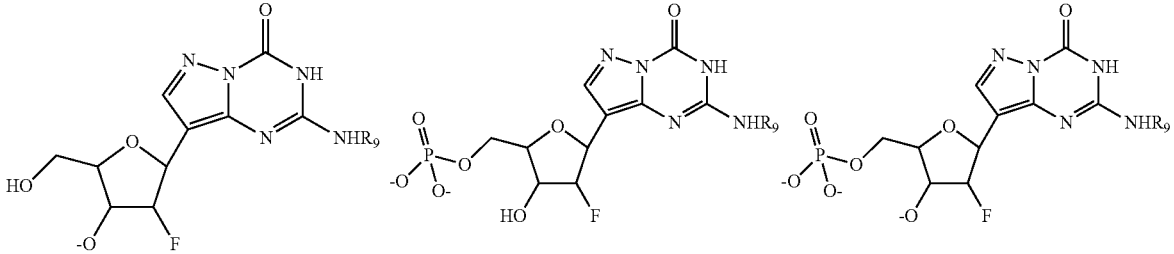

*The —[O—$PO_3$]2- in the above compounds may be substituted with another phosphate moiety, including, for example, a phosphate linking moiety, a triesterphosphorothioate moiety [—[O—$PO_2$S]2-] (a) or —[O—$PO_2(BH_3)$]2- (b). The phosphate linking moiety is —[O—P(O)(R')]—, wherein R' is O—, S—, $BH_3$—, or N—, preferably O—, S—, or $BH_3$—, more preferably O—, as well as to a protonated form thereof.

In some embodiments of the dsRNA molecule the sense strand comprises at least one pyrazolotriazine nucleotide analogue. In some embodiments the antisense strand comprises at least one pyrazolotriazine nucleotide analogue. In some embodiments each of the sense strand and the antisense strand comprises at least one pyrazolotriazine nucleotide analogue. In various embodiments the 5' terminus of the sense strand comprises a PT analogue of general formula IIa selected from compounds 3, 7, 9, 13, 15, 19, 21, 25, 27 or 31. In various embodiments the 5' terminus of the antisense strand comprises a PT analogue of general formula IIa selected from compounds 3, 7, 9, 13, 15, 19, 21, 25, 27 or 31. In various embodiments the 5' terminus of the sense strand comprises a PT analogue of general formula IIb selected from compounds 33, 37, 39, 43, 45, 49, 51, 55, 57 or 61.

In various embodiments the 3' terminus of the sense strand comprises a PT analogue of general formula IIa selected from compounds 5, 11, 17, 23 or 29. In various embodiments the 3' position of the antisense strand comprises a PT analogue of general formula IIa selected from compounds 5, 11, 17, 23 or 29. In various embodiments the 3' position of the sense strand comprises a PT analogue of general formula IIb selected from compounds 35, 41, 47, 53 or 59. In various embodiments the 3' position of the antisense strand comprises a PT analogue of general formula IIb selected from compounds 35, 41, 47, 53 or 59.

In various embodiments the sense strand comprises a PT analogue of general formula IIa selected from compounds 7, 13, 19, 25 or 31 in an internal position. In various embodiments the antisense strand comprises a PT analogue of general formula IIa selected from compounds 7, 13, 19, 25 or 31 in an internal position. In various embodiments the sense strand comprises a PT analogue of general formula IIb selected from compounds 37, 43, 49, 55 or 61 in an internal position. In various embodiments the antisense strand comprises a PT analogue of general formula IIb selected from compounds 37, 43, 49, 55 or 61 in an internal position. In some embodiments the internal position comprises position 18 of the sense strand.

The various nucleoside analogues disclosed herein may be synthesized according to any suitable technology or procedure known in the art, and preferably include amine and/or hydroxy protecting groups present during the synthesis steps.

In some embodiments the dsRNA includes one or more modified nucleotides selected from those having naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halouracil, 5-halocytosine, 6-azacytosine and 6-az thymine, pseudouracil, deoxypseudouracil, 4-thiouracil, ribo-2-thiouridine, ribo-4-thiouridine, 8-haloadenine, 8-aminoadenine, 8-thioladenine, 8-thiolalkyl adenines, 8-hydroxyl adenine and other 8-substituted adenines, 8-haloguanines, 8-aminoguanine, 8-thiolguanine, 8-thioalkylguanines 8-hydroxylguanine and other substituted guanines, other aza and deaza adenines, other aza and deaza guanines, 5-methylribouridine, 5-trifluoromethyl uracil, 5-methylribocytosine, and 5-trifluorocytosine. In some embodiments one or more nucleotides in an oligomer is substituted with inosine.

In some embodiments the double-stranded molecule further comprises at least one modified ribonucleotide selected from the group consisting of a ribonucleotide having a sugar modification, a base modification or an internucleotide linkage modification and may contain DNA, and modified nucleotides such as LNA (locked nucleic acid), ENA (ethylene-bridged nucleic acid), L-DNA or L-RNA, PNA (peptide nucleic acid), arabinoside, phosphonocarboxylate or phosphinocarboxylate nucleotide (PACE nucleotide), or nucleotides with a 6 carbon sugar.

Modified deoxyribonucleotide includes, for example 5'OMe DNA (5-methyl-deoxyriboguanosine-3'-phosphate); PACE (deoxyriboadenosine 3' phosphonoacetate, deoxyribocytidine 3' phosphonoacetate, deoxyriboguanosine 3' phosphonoacetate, deoxyribothymidine 3' phosphonoacetate).

Bridged nucleic acids include LNA (2'-O,4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

All analogues of, or modifications to, a nucleotide/oligonucleotide are employed as disclosed herein, provided that said analogue or modification does not substantially adversely affect the properties, e.g. function, of the nucleotide/oligonucleotide. Acceptable modifications include modifications of the sugar moiety, modifications of the base moiety, modifications in the internucleotide linkages and combinations thereof.

A sugar modification includes a modification on the 2' moiety of the sugar residue and encompasses amino, fluoro, alkoxy (e.g. methoxy), alkyl, amino, fluoro, chloro, bromo, CN, CF, imidazole, carboxylate, thioate, $C_1$-$C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; NO2, N3; heterocycloalkyl; heterocycloalkaryl; aminoalkylamino; polyalkylamino or substituted silyl, as, among others, described in European patents EP 0 586 520 B1 or EP 0 618 925 B1.

In one embodiment the modified molecules comprise at least one ribonucleotide comprising a 2' modification on the sugar moiety ("2' sugar modification"). In certain embodiments the sugar modified moiety comprises 2'O-alkyl or 2'-fluoro or 2'O-allyl or any other 2' modification. In some embodiments a preferred 2'O-alkyl is 2'O-methyl (methoxy) sugar modification. Other stabilizing modifications are also possible (e.g. terminal modifications).

In some embodiments the backbone of the oligonucleotides is modified and comprises phosphate-D-ribose entities but may also contain thiophosphate-D-ribose entities, triester, thioate, 2'-5' bridged backbone (also may be referred to as 2'5' linked nucleotide or 5'-2'), PACE and the like.

As used herein, the terms "non-pairing nucleotide analogue" means a nucleotide analogue which comprises a non-base pairing moiety including but not limited to: 6 des amino adenosine (Nebularine), 4-Me-indole, 3-nitropyrrole, 5-nitroindole, Ds, Pa, N3-Me riboU, N3-Me riboT, N3-Me dC, N3-Me-dT, N1-Me-dG, N1-Me-dA, N3-ethyl-dC, N3-Me dC. In some embodiments the non-base pairing nucleotide analogue is a ribonucleotide. In other embodiments the non-base pairing nucleotide analogue is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have enhanced stability in vivo and in vitro. Other modifications include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of siRNA compounds comprising LNA nucleotides are disclosed in Elmen et al., (NAR 2005, 33(1):439-447).

"TNA" refers to (L)-alpha-threofuranosyl nucleotides. The TNA phosphoramidites are linked to adjacent TNA, deoxyribonucleotide or ribonucleotide by (3'→2') phosphodiester linkages. TNA comprise a four-carbon sugar (Schoning, et al Science 2000. 290:1347-51). In some embodiments, in addition to TNA the siRNA compound further comprises at least one modified ribonucleotide selected from the group consisting of a ribonucleotide having a sugar modification, a base modification or an internucleotide linkage modification and may contain DNA, a mirror nucleotide (L-DNA, L-RNA) and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), or nucleotides with a 6 carbon sugar.

Other modifications include 3' terminal modifications also known as capping moieties. Such terminal modifications are selected from a nucleotide, a modified nucleotide, a lipid, a peptide, a sugar and inverted abasic moiety. Such modifications are incorporated, for example at the 3' terminus of the sense and/or antisense strands.

What is sometimes referred to herein as an "abasic nucleotide" or "abasic nucleotide analogue" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and/or base. The abasic pseudo-nucleotide lacks a base, and thus is not strictly a nucleotide.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogues including 4',5'-methylene nucleotide; 1-(β-D-erythrofuranosyl) nucleotide; 4'-thionucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA. In some embodiments the molecules are synthesized with one or more inverted nucleotides, for example inverted thymidine or inverted adenosine (see, for example, Takei, et al., 2002, JBC 277(26):23800-06). In some embodiments an inverted abasic deoxyribose moiety is covalently attached to the 5' terminus of the sense strand (N')y.

"Terminal functional group" includes halogen, alcohol, amine, carboxylic, ester, amide, aldehyde, ketone, ether groups.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analogue and a nucleotide joined to an adjacent nucleotide by a 2'-5' internucleotide phosphate bond; an threose nucleic acid (TNA) moiety; bridged nucleic acids including locked nucleic acids (LNA) and ethylene bridged nucleic acids (ENA).

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate.

Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The mirror nucleotide is a ribonucleotide or a deoxyribonucleotide and my further comprise at least one sugar, base and/or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror dT) and L-RNA (L-riboadenosine-3'-phosphate (mirror rA); L-ribocytidine-3'-phosphate (mirror rC); L-riboguanosine-3'-phosphate (mirror rG); L-ribouridine-3'-phosphate (mirror dU).

According to one aspect provided herein are chemically modified dsRNA molecules comprising unmodified ribonucleotides, modified ribonucleotides and/or unconventional moieties and at least one PT nucleotide analogue. In some embodiments the chemically modified dsRNA comprises at least one modified nucleotide selected from the group consisting of a sugar modification, a base modification and an internucleotide linkage modification and may contain modified nucleotides such as LNA (locked nucleic acid) including ENA (ethylene-bridged nucleic acid; PNA (peptide nucleic acid); arabinoside; PACE (phosphonoacetate and derivatives thereof), or nucleotides with a six-carbon sugar or an unconventional moiety selected from an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond. In some embodiments a modified ribonucleotide is a 2'OMe sugar modified ribonucleotide. In some embodiments some or all of the pyrimidines in the antisense strand comprise 2'OMe sugar modified ribonucleotides. In some embodiments some or all of the purines in the antisense strand comprise 2'OMe sugar modified ribonucleotides. In preferred embodiments the antisense strand comprises 2'OMe sugar modified ribonucleotides in nuclease sensitive positions. In some embodiments the sense strand comprises 2'OMe sugar modified ribonucleotides in nuclease sensitive positions. In some embodiments the sense strand [e.g. (N')y in Structure A1 or $N^2$—(N')y in Structure A2] comprises one or more 2'OMe sugar modified ribonucleotides. In some embodiments the sense strand [e.g. (N')y in Structure A1 or $N^2$—(N')y in Structure A2] comprises one or more deoxyribonucleotide. In some embodiments the siRNA is blunt ended at the 3' terminus of the compound, i.e. the dsRNA or siRNA is blunt ended on the end defined by the 3'-terminus of the sense or passenger strand and the 5'-terminus of antisense or guide strand.

In other embodiments at least one of the two strands has a 3' overhang of at least one nucleotide, nucleotide analogue or non-nucleotide moiety covalently attached at the 3'-terminus; in some embodiments the overhang comprises at least one deoxyribonucleotide. At least one of the strands optionally comprises an overhang of at least one nucleotide or nucleotide analogue (e.g. PT nucleotide analogue) at the 3'-terminus. The overhang consists of from about 1 to about 5 nucleotide, nucleotide analogues, non-nucleotide moieties or combinations thereof.

In various embodiments the overhangs are independently selected from a nucleotide, a non-nucleotide and a combination thereof. In certain embodiments, each overhang, if present, is independently selected from a ribonucleotide, deoxyribonucleotide, PT nucleotide analogue, abasic deoxyribose moiety, abasic deoxyribose moiety, C3-amino-Pi, C4-amino-Pi, C5-amino-Pi, C6-amino-Pi, a mirror nucleotide.

In some embodiments each of Z and/or Z' independently includes a C2, C3, C4, C5 or C6 alkyl moiety, optionally a C3 [propane, —(CH2)$_3$-] moiety or a derivative thereof including propanol (C3-OH), propanediol, and phosphodiester derivative of propanediol ("C3Pi"). In preferred embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In a specific embodiment x=y=19 and Z comprises C3-C3. In some embodiments the C3-C3 overhang is covalently attached to the 3' terminus of (N)x or (N')y via a covalent linkage, for example a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH (OH is hydroxy). In some embodiments the 3' non-nucleotide overhang is C3Pi-C3OH.

In various embodiments the alkyl moiety comprises an alkyl derivative including a C3 alkyl, C4 alkyl, C5 alky or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof.

The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate.

The structures of exemplary 3' terminal C3 non-nucleotide moieties are as follows:

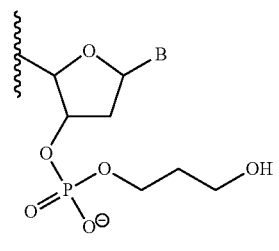

3' terminus-C3-OH

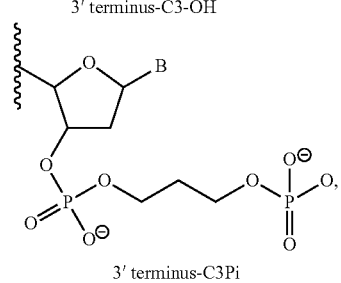

3' terminus-C3Pi

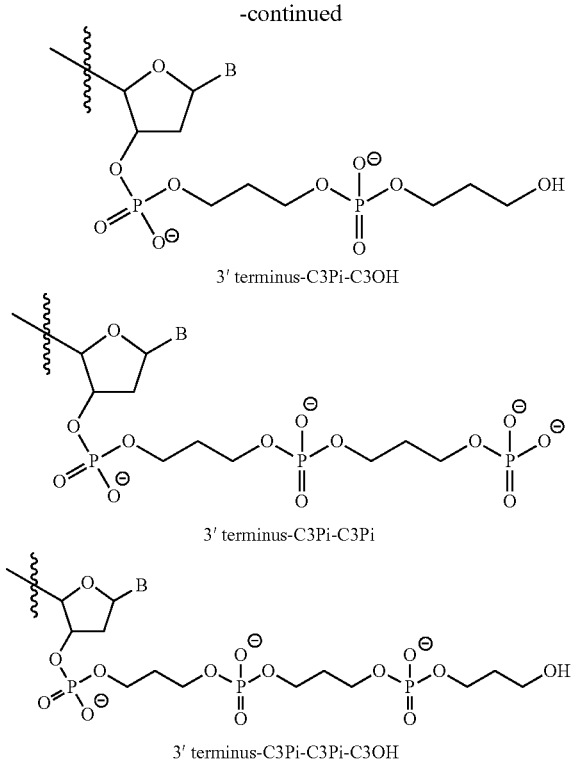

3' terminus-C3Pi-C3OH

3' terminus-C3Pi-C3Pi

3' terminus-C3Pi-C3Pi-C3OH

In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof. In some embodiments, when the 3' terminal nucleotide comprises a 2'5' linked nucleotide the C3 moiety may be linked to the 2' position of the sugar via a phosphodiester linkage or other linkage.

In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)$_3$, (propyl phosphate)$_2$-propanol, (propyl phosphate)$_2$-propyl phosphorothioate. Any propane or propanol conjugated moiety can be included in Z or Z'.

In additional embodiments each of Z and/or Z' comprises a combination of an abasic moiety and an unmodified deoxyribonucleotide or ribonucleotide or a combination of a hydrocarbon moiety and an unmodified deoxyribonucleotide or ribonucleotide or a combination of an abasic moiety (deoxyribo or ribo) and a hydrocarbon moiety. In such embodiments, each of Z and/or Z' comprises C3Pi-rAb or C3Pi-dAb.

The length of the RNA duplex is from about 15 to about 49 ribonucleotides, or about, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49, preferably 18-40, 18-27, 18-25 or 19 to 23 ribonucleotides. In some embodiments the length of each strand (oligomer) is independently selected from the group consisting of about 18 to about 40 nucleotides, preferably 18 to 27, 18 to 25, 19-23 and more preferably 19 ribonucleotides.

In some embodiments, the complementarity between the antisense strand of the dsRNA and the target nucleic acid is perfect. In other embodiments, the antisense strand of the modified siRNA compound and the target nucleic acid are substantially complementary, i.e. having one, two or up to three mismatches between said antisense strand and the target nucleic acid. In some embodiments the antisense strand is mismatched to the target mRNA at the 5' terminal nucleotide.

In certain embodiments the complementarity between the antisense strand and the sense strand of the dsRNA molecule is perfect. In some embodiments, the strands are substantially complementary, i.e. having one, two or up to three mismatches between said antisense strand and said sense strand. In some embodiments the antisense strand is fully complementary to the sense strand.

In some embodiments the modified dsRNA molecules disclosed herein exhibit enhanced activity, when compared to a dsRNA molecule wherein the antisense strand including the 5'-terminal nucleotide is fully complementary to a consecutive sequence in a target mRNA.

The chemical modifications disclosed herein are beneficially applied to double-stranded RNA useful in inhibiting or attenuating mammalian and non-mammalian gene expression.

dsRNA Oligonucleotides

In one aspect provided are double-stranded ribonucleic acid molecules, wherein:
(a) the ribonucleic acid molecule includes a sense strand and an antisense strand wherein each strand is independently 15 to 49 nucleotides in length;
(b) the sense strand and/or the antisense strand includes at least one pyrazolotriazine nucleotide analogue;
(c) a 15 to 49 nucleotide sequence of the antisense strand is complementary to a sequence of an mRNA of a target gene; and
(d) a 15 to 49 nucleotide sequence of the sense strand is complementary to the antisense strand and includes a 15 to 49 nucleotide sequence of an mRNA of a target gene.

In some embodiments the antisense strand is fully complementary to the sequence of an mRNA of a target gene, and the sense strand and the antisense strand are fully complementary. Accordingly provided herein is a double-stranded ribonucleic acid molecule set forth below in structure A1:

5'(N)x-Z3'(antisense strand)

3'Z'—(N')y-z"5'(sense strand)    (A1)

wherein each of N and N' is a ribonucleotide which may be unmodified or modified, or an unconventional moiety;
wherein at least one of N or N' comprises a pyrazolotriazine nucleotide analogue;
wherein each of (N)x and (N')y is an oligonucleotide in which each consecutive N or N' is joined to the next N or N' by a covalent bond;
wherein each of Z and Z' is independently present or absent, but if present independently includes 1-5 consecutive nucleotides or non-nucleotide moieties or a combination thereof, or a vitamin or a drug moiety covalently attached at the 3' terminus of the strand in which it is present;
wherein z" may be present or absent, but if present is a capping moiety, a vitamin or a drug moiety covalently attached at the 5' terminus of (N')y;
wherein each of x and y is independently an integer between 15 and 49; and wherein the sequence of (N')y is complementary to the sequence of (N)x and wherein at least a portion of (N)x is complementary to a consecutive sequence in a target RNA; with the proviso that not each N and N' is a deoxyribonucleotide.

In some embodiments the covalent bond joining each consecutive N or N' is a phosphodiester bond.

In some embodiments x=y and each of x and y is 19, 20, 21, 22 or 23. In various embodiments x=y=19.

In some embodiments the sense strand comprises at least one pyrazolotriazine nucleotide analogue. In some embodiments the antisense strand comprises at least one pyrazolotriazine nucleotide analogue. In some embodiments each of the sense strand and the antisense strand comprises at least one pyrazolotriazine nucleotide analogue.

In some embodiments all of the adenosine nucleotides in the sense strand are substituted with adenosine and/or deoxyadenosine pyrazolotriazine nucleotide analogues. In some embodiments all of the adenosine nucleotides in the antisense strand are substituted with adenosine and/or deoxyadenosine pyrazolotriazine nucleotide analogues. In some embodiments all of the adenosine nucleotides in the sense strand and in the antisense strand are substituted with adenosine and/or deoxyadenosine pyrazolotriazine nucleotide analogues.

In some embodiments all of the guanosine nucleotides in the sense strand are substituted with guanosine and/or deoxyguanosine pyrazolotriazine nucleotide analogues. In some embodiments all of the guanosine nucleotides in the antisense strand are substituted with guanosine and/or deoxyguanosine pyrazolotriazine nucleotide analogues. In some embodiments all of the guanosine nucleotides in the sense strand and in the antisense strand are substituted with guanosine and/or deoxyguanosine pyrazolotriazine nucleotide analogues.

In various embodiments the double-stranded ribonucleic acid molecule comprises a mismatch to the target mRNA at the 5' terminal nucleotide of the guide strand (antisense strand). Accordingly, in various embodiments provided is a double-stranded ribonucleic acid molecule having the following structure A2:

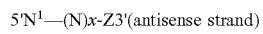

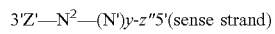 (A2)

wherein each of $N^2$, N and N' is an unmodified or modified ribonucleotide, or an unconventional moiety;

wherein at least one of $N^1$, $N^2$, N or N' comprises a pyrazolotriazine nucleotide analogue;

wherein each of (N)x and (N')y is an oligonucleotide in which each consecutive N or N' is joined to the adjacent N or N' by a covalent bond;

wherein each of x and y is independently an integer between 17 and 24;

wherein the sequence of (N')y is complementary to the sequence of (N)x and (N)x comprises an antisense sequence complementary to a consecutive sequence in a target RNA;

wherein $N^1$ is covalently bound to (N)x and is mismatched to the target RNA or is a complementary DNA moiety to the target RNA;

wherein $N^1$ is a moiety selected from the group consisting of natural or modified uridine, deoxyribouridine, ribothymidine, deoxyribothymidine, adenosine, deoxyadenosine, adenosine pyrazolotriazine nucleic acid analogue, deoxyadenosine pyrazolotriazine nucleic acid analogue;

wherein z'' may be present or absent, but if present is a capping moiety, a vitamin or a drug moiety covalently attached at the 5' terminus of $N^2$— (N')y; and wherein each of Z and Z' is independently present or absent, but if present is independently 1-5 consecutive nucleotides, consecutive non-nucleotide moieties or a combination thereof, or a vitamin or a drug moiety covalently attached at the 3' terminus of the strand in which it is present; with the proviso that not each N and N' is a deoxyribonucleotide.

In various embodiments the double-stranded ribonucleic acid comprises at least one adenosine ribonucleotide in the sense strand, the antisense strand or the sense strand and antisense strand is substituted with a deoxyriboadenosine PT nucleotide analogue or an adenosine PT nucleotide analogue of formula IIa, and further comprises one or more of the following modifications:

a threose nucleic acid moiety, a 2'5' linked nucleotide or a mirror nucleotide in at least one of positions 5, 6, 7, 8, or 9 from the 5' terminus of the antisense strand [(N)x or $N^1$—(N)x)];

a threose nucleic acid moiety, a 2'5' linked nucleotide or a pseudoUridine in at least one of positions 9 or 10 from the 5' terminus of the sense strand [(N')y or $N^2$—(N')y)];

1, 2, 3, 4, 5, 6, 7, 8, 9 or 10 threose nucleic acid moieties or 2'5' linked nucleotides at the 3' terminal or penultimate positions the sense strand [(N')y or $N^2$—(N')y)].

In some embodiments of structures A1 or A2 the sequence of (N')y is fully complementary to the sequence of (N)x. In various embodiments of (A1) and A2 sequence of $N^2$—(N')y is complementary to the sequence of $N^1$—(N)x. In some embodiments (N)x comprises an antisense that is fully complementary to about 17 to about 24 consecutive nucleotides in a target RNA.

In some embodiments $N^1$ is selected from deoxyadenosine, deoxyuridine, ribothymidine or deoxythymidine and wherein the nucleotide in the pairing nucleotide in the target RNA is uridine. In preferred embodiments $N^1$ selected from deoxyadenosine or deoxyuridine. In some embodiments $N^1$ and $N^2$ form a base pair between uridine or deoxyuridine, and adenosine or deoxyadenosine. In other embodiments $N^1$ and $N^2$ form a base pair between deoxyuridine and adenosine.

The following table, Table 4 provides examples of $N^1$ and corresponding $N^2$.

TABLE 4

| Target nucleotide | 5' terminal nucleotide of AS with full match to target | $N^1$ (5' terminal position of AS) | $N^2$ (3' terminal position of SEN) |
|---|---|---|---|
| A | U | rA, dA, ptrA, ptdA | U, dU, rT, dT |
| A | U | dU, rT, dT | rA, dA, ptrA, ptdA |
| C | rG | rA, dA, ptrA, ptdA | U, dU, rT, dT |
| C | rG | U, dU, rT, dT | rA, dA, ptrA, ptdA |
| G | rC | rA, dA, ptrA, ptdA | U, dU, rT, dT |
| G | rC | U, dU, rT, dT | rA, dA, ptrA, ptdA |
| U | rA | dA, ptrA, ptdA | U, dU rT, dT |
| U | rA | dU rT, dT | rA, dA, ptrA, ptdA |

Legend to Table 4: dA-deoxyadenosine; rA-adenosine, ptrA-adenosine PT nucleotide analogue, ptdA-deoxyadenosine PT nucleotide analogue, rC-cytidine, rG-guanosine, U-uridine, dU-deoxyuridine, dT-thymidine, rT-ribothymidine (5'methyluridine)

In some embodiments of (A2), $N^1$ comprises uridine or adenosine. In certain embodiments $N^2$ comprises a 2'OMe sugar modified ribonucleotide. In some embodiments $N^1$ comprises 2'OMe sugar modified ribouridine and $N^2$ comprises adenosine or modified adenosine. In some embodiments $N^1$ comprises adenosine and $N^2$ comprises a ribouridine or modified ribouridine. In some embodiments Z and Z' are absent. In other embodiments one of Z or Z' is present.

In some embodiments each of N and N' is an unmodified ribonucleotide. In some embodiments at least one of N or N' comprises a chemically modified ribonucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' comprises a 2'OMe sugar-modified ribonucleotide.

In some embodiments the sequence of (N')y is fully complementary to the sequence of (N)x. In other embodiments the sequence of (N')y is substantially complementary to the sequence of (N)x.

Structures A1 and A2 are useful with any oligonucleotide pair (sense and antisense strands) to a mammalian or non-mammalian gene. In some embodiments the mammalian gene is a human gene.

In some embodiments a modified siRNA compound having structure A2 exhibits beneficial properties including enhanced activity (e.g. reduced IC50, increased knock down, reduced residual mRNA) when compared to a control compound, i.e. an siRNA compound wherein the antisense oligonucleotide is fully complementary (including 5' terminal nucleotide base paired e.g. A-U, U-A, C-G, G-C) to a nucleotide sequence in a target mRNA. In some embodiments the activity is enhanced by at least 5%, by at least 10%, by at least 20%, by at least 25% or more when compared to a control compound.

In another aspect provided is a method of generating a double-stranded RNA molecule consisting of a sense strand and an antisense strand comprising the steps of
a) selecting a consecutive 18 to 40 nucleotide sequence in a target RNA and synthesizing an antisense strand comprising complementarity to the consecutive 18 to 40 nucleotide sequence of the target mRNA wherein the 5' terminal nucleotide of the antisense strand is substituted with uridine, modified uridine, ribothymidine, deoxyribothymidine, adenosine, modified adenosine, deoxyadenosine or modified deoxyadenosine;
b) synthesizing a sense strand of 18 to 40 nucleotides having complementarity to the antisense strand, wherein the 3' terminal nucleotide of the sense strand forms a Watson Crick base pair with the 5' terminal nucleotide of the guide strand; and
c) annealing the antisense and sense strands; thereby generating a double-stranded RNA molecule.

In some embodiments a rG:rU wobble is not generated between the 5' terminal nucleotide of the antisense strand and the 3' terminal nucleotide of the target mRNA According to one embodiment provided is a method of generating a double-stranded RNA molecule consisting of a sense strand and an antisense strand exhibiting enhanced RNAi activity when compared to an unmodified or similarly modified double-stranded RNA molecule comprising the steps of
a) selecting a consecutive 18 to 40 nucleotide sequence in a target mRNA and synthesizing a sense strand comprising the consecutive 18 to 40 nucleotide sequence of the target mRNA wherein the 3' terminal nucleotide is substituted with adenosine, modified adenosine, deoxyadenosine or modified deoxyadenosine;
b) synthesizing an antisense strand of 18 to 40 nucleotides having complementarity to the sense strand wherein the 5' terminal nucleotide comprises ribouridine, modified ribouridine, deoxyribouridine or modified deoxyribouridine and base pairs with the 3' terminal nucleotide of the passenger strand;
c) annealing the sense strand to the antisense strand; thereby generating a double-stranded RNA molecule having enhanced RNAi activity.

In some embodiments the modified double-stranded RNA molecule exhibits enhanced RNAi activity when compared to an unmodified siRNA duplex, i.e. a duplex having full match to the target mRNA.

According to another aspect, provided herein is a method of generating a modified a double-stranded RNA molecule consisting of a sense strand and antisense strand exhibiting enhanced RNAi activity when compared to an unmodified a double-stranded RNA molecule comprising the steps of
a) selecting a consecutive 18 to 40 nucleotide sequence in a target mRNA and synthesizing a sense strand comprising the consecutive 18 to 40 nucleotide sequence of the target mRNA wherein the 3' terminal nucleotide is substituted with adenosine, modified adenosine, deoxyadenosine or modified deoxyadenosine;
b) synthesizing an antisense strand of 18 to 40 nucleotides having complementarity to the sense strand wherein the 5' terminal nucleotide comprises ribouridine, modified ribouridine, deoxyribouridine or modified deoxyribouridine and base pairs with the 3' terminal nucleotide of the sense strand;
c) annealing the sense strand to the antisense strand; thereby generating a double-stranded RNA molecule having enhanced RNAi activity.

In some embodiments step a) includes selecting a consecutive 18 to 25 nucleotide, or 18, 19, 20, 21, 22, 23, 24 or 25 nucleotide sequence in a target RNA in a target cell wherein the 3' terminal nucleotide is other than adenosine.

In some embodiments Z and Z' are absent. In other embodiments one of Z or Z' is present. In various embodiments Z and Z' are independently selected from a nucleotide, a non-nucleotide and a combination thereof. In certain embodiments, each of Z and Z', if present, is independently selected from a ribonucleotide, deoxyribonucleotide, abasic deoxyribose moiety, abasic deoxyribose moiety, C3-amino-Pi, C4-amino-Pi, C5-amino-Pi, C6-amino-Pi, a mirror nucleotide. In some embodiments Z is present. In some preferred embodiments at least one of Z or Z' is a pyrazolotriazine nucleotide analogue as described herein. In other embodiments Z' is present. In additional embodiments both Z and Z' are present. In some embodiments Z and Z' are present and are identical. In further embodiments Z and Z' are present and are different. In some embodiments Z and Z' are independently 1, 2, 3, 4 or 5 non-nucleotide moieties or a combination of 2, 3, 4, or 5 non-nucleotide moieties and nucleotides. In some embodiments each of Z and/or Z' comprises 2 non-nucleotide moieties covalently linked to the 3' terminus of the siRNA strand via a phosphodiester bond. In some embodiments Z and Z' are present and each one independently comprises one or more alkyl moieties and/or derivative thereof. In some embodiments, $N^2$ comprises riboadenosine and $N^1$ comprises uridine (ribouridine).

A non-nucleotide moiety is selected from the group consisting of an abasic moiety, an inverted abasic moiety, an alkyl moiety or derivative thereof, and an inorganic phosphate. In some embodiments a non-nucleotide moiety is an alkyl moiety or derivative thereof. In some embodiments the alkyl moiety comprises a terminal functional group including alcohol, a terminal amine, a terminal phosphate or a terminal phosphorothioate moiety.

In some embodiments Z is present and comprises one or more non-nucleotide moieties selected from the group consisting of an abasic moiety, an inverted abasic moiety, hydrocarbon moiety or derivative thereof, and an inorganic phosphate. In some embodiments Z is present and comprises one or more alkyl moieties and/or derivative thereof.

In additional embodiments Z' is present and comprises one or more non-nucleotide moieties selected from the group consisting of an abasic moiety, an inverted abasic moiety, a hydrocarbon moiety, and an inorganic phosphate. In some embodiments Z' is present and comprises one or more alkyl moieties and/or derivative thereof.

In additional embodiments x=y=18 and either Z or Z' is present and independently comprises two non-nucleotide moieties, for example a C3Pi—C3Pi or C3Pi-C3OH.

In additional embodiments x=y=18 and Z and Z' are present and each independently comprises two non-nucleotide moieties, for example a C3Pi—C3Pi or C3Pi-C3OH.

In some embodiments each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example dAb-dAb or rAb-rAb or dAb-rAb or rAb-dAb. Each moiety is covalently conjugated an adjacent moiety via a covalent bond, preferably a phospho-based bond. In some embodiments the phospho-based bond is a phosphorothioate, a phosphonoacetate or a phosphodiester bond.

In a specific embodiment of (A1) x=y=19 and Z comprises C3Pi-C3OH or C3Pi-C3Pi. In a specific embodiment x=y=19 and Z' comprises C3Pi-C3OH or C3Pi-C3Pi. In some embodiments the C3-C3 overhang is covalently attached to the 3' terminus of (N)x or (N')y via covalent linkage, for example a phosphodiester linkage. In some embodiments the linkage between a first C3 and a second C3 is a phosphodiester linkage.

In a specific embodiment of (A2) x=y=18 and Z comprises C3Pi-C3OH or C3Pi-C3Pi. In a specific embodiment x=y=18 and Z' comprises C3Pi-C3OH or C3Pi-C3Pi. In some embodiments the C3-C3 overhang is covalently attached to the 3' terminus of $N^1$—(N)x or $N^2$—(N')y via covalent linkage, for example a phosphodiester linkage. In some embodiments the linkage between a first C3 and a second C3 is a phosphodiester linkage.

In various embodiments the alkyl moiety is a C3 alkyl to C6 alkyl moiety comprising a terminal hydroxyl, a terminal amino, terminal phosphate group. In some embodiments the alkyl moiety is a C3 alkyl moiety. In some embodiments the C3 alkyl moiety comprises propanol, propylphosphate, propylphosphorothioate or a combination thereof.

The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate.

In additional embodiments each of Z and/or Z' comprises a combination of an abasic moiety and an unmodified deoxyribonucleotide or ribonucleotide or a combination of a hydrocarbon moiety and an unmodified deoxyribonucleotide or ribonucleotide or a combination of an abasic moiety (deoxyribo or ribo) and a hydrocarbon moiety. In such embodiments, each of Z and/or Z' comprises C3-rAb or C3-dAb. In some embodiments one of Z or Z' comprises a vitamin or a drug moiety.

In preferred embodiments of (A2) x=y=18, Z' is absent, Z is present and comprises two alkyl moieties covalently linked to each other via a phosphodiester bond, $N^2$ comprises riboadenosine and $N^1$ comprises uridine.

In some embodiments N and N' comprise an unmodified nucleotide. In some embodiments at least one of N or N' comprises a chemically modified ribonucleotide or an unconventional moiety. In some embodiments the unconventional moiety is selected from the group consisting of a mirror nucleotide, an abasic ribose moiety, an abasic deoxyribose moiety, a deoxyribonucleotide, a modified deoxyribonucleotide, a mirror nucleotide, a non-base pairing nucleotide analogue, a bridged nucleic acid and a nucleotide joined to an adjacent nucleotide by a 2'-5' internucleotide phosphate bond. In some embodiments the unconventional moiety is a mirror nucleotide, preferably an L-DNA moiety. In some embodiments at least one of N or N' is modified at one or more of the sugar, the base or linker. In certain embodiments at least one of N or N' comprises a 2'OMe sugar modified ribonucleotide.

In preferred embodiments the chemically modified ribonucleotides are positioned along the sense strand and/or antisense strand modifications and effect a desired property upon the double-stranded compound including increased on target activity and/or decreased off target activity and/or increased stability to nucleases.

In some embodiments of the double-stranded nucleic acid molecules of Structures A1 and A2, N in at least one of positions 5, 6, 7, 8, or 9 from the 5' terminus of (N)x or $N^1$—(N)x is selected from a threose nucleic acid (TNA) moiety, a 2'5' linked nucleotide, a mirror nucleotide or a combination thereof.

In some embodiments of (A1), x=19 and (N)x comprises a TNA moiety in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In some embodiments Structure A2 x=18 and $N^1$—(N)x of (A2) comprises a TNA moiety in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. $N^1$ is counted as position 1 of the antisense (guide) strand (5'>3').

In some embodiments of (A1) x=19 and (N)x comprises a 2'-5' nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In preferred embodiments (N)x comprises a 2'-5' nucleotide in position 5, in position 7, in position 8, in position 9, in positions 6-7, in positions 7-8, or in positions 8-9. In some embodiments of (A2) x=18 and $N^1$—(N)x comprises a 2'-5' nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In preferred embodiments $N^{1-}$(N)x comprises a 2'-5' nucleotide in position 5, in position 7, in position 8, in position 9, in positions 6-7, in positions 7-8, or in positions 8-9.

In some embodiments Structure A1 x=19 and (N)x comprises a mirror nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In some embodiments (N)x of (A1) or $N^1$—(N)x of (A2) comprises a mirror nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments of the double-stranded ribonucleic acid molecules, N' in at least one of positions 9 or 10 from the 5' terminus of (N')y in Structure A1 or $N^2$—(N')y in Structure A2 is selected from a threose nucleic acid (TNA) moiety, a 2'5' linked nucleotide, a mirror nucleotide or a combination thereof. Without wishing to be bound to theory, a double-stranded nucleic acid molecule having a threose nucleic acid (TNA) moiety, a 2'5' linked nucleotide, or a pseudoUridine at one or both of positions 9 or 10 in the sense (passenger) strand confers increased on target activity and/or increased nuclease stability.

In some embodiments of (A1) (N')y comprises a threose nucleic acid (TNA) moiety in position 9, or in position 10 or in positions 9-10. In some embodiments of (A2) $N^2$—(N')y comprises a threose nucleic acid (TNA) moiety in position 9, or in position 10 or in positions 9-10.

In some embodiments of (A1) (N')y comprises a 2'5' linked nucleotide in position 9, or in position 10 or in positions 9-10. In some embodiments of (A2) $N^2$—(N')y comprises a 2'5' linked nucleotide in position 9, or in position 10 or in positions 9-10.

In some embodiments of (A1) (N')y comprises a mirror nucleotide in position 9, or in position 10 or in positions 9-10. In some embodiments of (A2) $N^2$—(N')y comprises a pseudoUridine in position 9, or in position 10 or in positions 9-10.

In some embodiments of the double-stranded ribonucleic acid molecules, N' comprises 2'5' linked nucleotides at the 4 most, 5 most or 6 most 3' terminal positions of (N')y in Structure A1 or $N^2$—(N')y in Structure A2. Without wishing to be bound to theory, a double-stranded nucleic acid molecule having multiple 2'5' linked nucleotides at the 3' terminus of the sense (passenger) strand confers increased nuclease stability to the duplex and/or reduced off target effect of the sense (passenger) strand.

In some embodiments of (A1) (N')y comprises 2'5' linked nucleotides in the four 3'-most terminal positions. In some embodiments the x=y=19 and (N')y comprises 2'5' linked nucleotides in positions 16, 17, 18 and 19.

In some embodiments of Structure (A2) $N^2$—(N')y comprises 2'5' linked nucleotides in the four 3'-most terminal positions. In some embodiments the x=y=18 and $N^2$—(N')y comprises 2'5' linked nucleotides in positions 16, 17, 18 and 19.

In some embodiments of (A1) (N')y comprises 2'5' linked nucleotides in the five 3'-most terminal positions. In some embodiments the x=y=19 and (N')y comprises 2'5' linked nucleotides in positions 15, 16, 17, 18 and 19.

In some embodiments of (A2) $N^2$—(N')y comprises 2'5' linked nucleotides in the five 3'-most terminal positions. In some embodiments the x=y=18 and $N^2$—(N')y comprises 2'5' linked nucleotides in positions 15, 16, 17, 18 and 19.

In some embodiments of (A1) (N')y comprises 2'5' linked nucleotides in the six 3'-most terminal positions. In some embodiments the x=y=19 and (N')y comprises 2'5' linked nucleotides in positions 14, 15, 16, 17, 18 and 19.

In some embodiments of (A2) $N^2$—(N')y comprises 2'5' linked nucleotides in the six 3'-most terminal positions. In some embodiments the x=y=19 and $N^2$—(N')y comprises 2'5' linked nucleotides in positions 14, 15, 16, 17, 18 and 19.

In some embodiments the double-stranded ribonucleic acid molecule is a siRNA, siNA or a miRNA.

The double-stranded ribonucleic acid compounds may further comprise combinations of the aforementioned modifications, and 2'OMe sugar modified ribonucleotides including 2'OMe sugar modified pyrimidines and/or purines in the sense strand and/or antisense strand. In certain embodiments (N)x and (N')y are fully complementary. In other embodiments (N)x and (N')y are substantially complementary. In certain embodiments (N)x is fully complementary to a target sequence. In other embodiments (N)x is substantially complementary to a target sequence. According to certain preferred embodiments provided herein is a modified siRNA compound comprising one or more modified nucleotide, wherein the modified nucleotide possesses a modification in the sugar moiety, in the base moiety or in the internucleotide linkage moiety.

In certain embodiments of the compound according to Structures A1 and A2 alternating ribonucleotides in each of $(N)_x$ and $(N')_y$ are 2'OMe sugar modified ribonucleotides. In some embodiments in (N)x the nucleotides are unmodified or (N)x comprises alternating 2'OMe sugar modified ribonucleotides and unmodified ribonucleotides; and the ribonucleotide located at the middle position of $N^1$—(N)x being modified or unmodified preferably unmodified; wherein (N')y comprises unmodified ribonucleotides further comprising one modified nucleotide at a terminal or penultimate position.

In particular embodiments of (A1), x=y=19, $N^1$ comprises an unmodified ribonucleotide, (N)x comprises 2' OMe sugar modified ribonucleotides and the ribonucleotide located at the middle of $N^1$—(N)x is unmodified. In certain embodiments x=y=19; in (N)x the nucleotides alternate between modified ribonucleotides and unmodified ribonucleotides, each modified ribonucleotide is a 2'OMe sugar modified ribonucleotide and the ribonucleotide located at the middle position of $N^1$—(N)x being unmodified; $N^2$ is joined to the 3' terminus of (N')y by a 2'-5' phosphodiester bond and at least three nucleotides at the 3' terminus of (N')y are 2'-5' nucleotides (covalently linked by 2'5' phosphodiester bonds). In other preferred embodiments, x=y=19; in (N)x the nucleotides alternate between modified ribonucleotides and unmodified ribonucleotides, each modified ribonucleotide is a 2'OMe sugar modified ribonucleotide and the ribonucleotide located at the middle of $N^1$—(N)x being unmodified; and five consecutive nucleotides at the 3' terminus of (N')y are 2'5' ribonucleotides (joined by four 2'-5' phosphodiester bonds). In some embodiments one or more of the 2'5' ribonucleotides comprise 3'-OMe sugar modification.

In certain preferred embodiments, x=y=19 and in (N')y the nucleotide in at least one position comprises a mirror nucleotide, a deoxyribonucleotide and a nucleotide joined to an adjacent nucleotide by a 2'-5' internucleotide bond.

In certain embodiments, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA in position 18. In some embodiments (N')y comprises 2'5' ribonucleotides in positions 15, 16, 17, 18, and 19 (5'>3'). In various embodiments (N)x further comprises a TNA, L-DNA or 2'5' ribonucleotide at one or more of positions 5, 6, 7, 8, or 9 (5'>3'). In other embodiments wherein x=y=20 the modifications for (N')y discussed above instead of being on positions 14, 15, 16, 17 are on positions 17, 18, 19, 20. For example, the modifications at one or both of positions 16 and 17 are on one or both of positions 18 or 19 for the 20-mer. All modifications in the 18-mer are similarly adjusted for the 20- and 22-mer.

In certain embodiments (N')y comprises an L-DNA in position 2 and 2'-5' internucleotide bonds in positions 15-19.

In some embodiments, neither strand of the modified dsRNA molecules disclosed herein is phosphorylated at the 3' and 5' termini. In other embodiments the sense and antisense strands are phosphorylated at the 3' termini. In yet another embodiment, the antisense strand is phosphorylated at the terminal 5' termini position using cleavable or non-cleavable phosphate groups. In yet another embodiment, either or both antisense and sense strands are phosphorylated at the 3' termini position using cleavable or non-cleavable phosphate groups.

Structure A1 is useful with any oligonucleotide pair (sense and antisense strands) to a mammalian or non-mammalian, i.e. microbial or viral gene. In some embodiments the mammalian gene is a human gene. Examples of oligonucleotide sequence pairs are provided in PCT Patent Publication Nos. WO 2006/023544, WO 2007/084684, WO 2008/050329, WO 2007/141796, WO 2009/044392, WO 2008/106102, WO 2008/152636, WO 2009/001359, WO/2009/090639 assigned to a co-assignee of the present disclosure and incorporated herein by reference in their entirety.

Unless otherwise indicated, in preferred embodiments of the structures discussed herein the covalent bond between each consecutive N and N' is a phosphodiester bond. Unless otherwise indicated, in preferred embodiments of the structures discussed herein the covalent bond between $N^1$ and (N)x and between $N^2$ and (N')y is a phosphodiester bond. In some embodiments at least one of the covalent bond is a phosphorothioate bond.

For all of the structures above, in some embodiments the oligonucleotide sequence of (N)x is fully complementary to the oligonucleotide sequence of (N')y. In other embodiments the antisense and sense strands are substantially complementary. In certain embodiments (N)x is fully complementary to a portion of a mammalian mRNA or a microbial RNA or a viral RNA. In other embodiments (N)x is substantially complementary to a portion of a mammalian mRNA or a microbial RNA or a viral RNA.

In some embodiments a modified dsRNA compound having structure (A2) exhibits beneficial properties including at least enhanced activity when compared to a dsRNA compound wherein $N^1$ is complementary to a nucleotide in a target mRNA.

Further provided is a pharmaceutical composition comprising a compound disclosed herein or a pharmaceutically acceptable salt thereof, in an amount effective to down-regulate a mammalian or a non-mammalian gene expression, and a pharmaceutically acceptable carrier, and use thereof for treatment of any one of the diseases and disorders disclosed herein. In some embodiments the mammalian gene is a human gene. In some embodiments the non-mammalian gene is involved in a mammalian disease, preferably human disease.

Further provided are methods for treating or preventing the incidence or severity of any one of the diseases or conditions disclosed herein or for reducing the risk or severity of a disease or a condition disclosed herein in a subject in need thereof, wherein the disease or condition and/or a symptom or risk associated therewith is associated with expression of a mammalian or a non-mammalian gene the method comprising administering to a subject in need thereof a therapeutically effective amount of a nucleic acid compound disclosed herein or of a pharmaceutically acceptable salt thereof. In a preferred embodiment the subject is a human subject. Provided herein are double-stranded nucleic acid molecules for therapy.

In another aspect, provided are the double-stranded ribonucleic acid molecules and composition comprising such molecules, according to any of the embodiments described herein, for use in down-regulating a target gene expression, wherein the target gene is a mammalian or non-mammalian target gene.

Further provided is the use of the double-stranded ribonucleic acid molecules or compositions comprising such molecules, according to any of the embodiments described herein, for the manufacture of a medicament for use in therapy.

siRNA Synthesis

Using public and proprietary algorithms the sense and antisense sequences of potential double-stranded RNA molecules are generated.

The dsRNA molecules according to the above specifications are prepared essentially as described herein. The modified nucleic acid molecules are synthesized by any of the methods that are well known in the art for synthesis of ribonucleic (or deoxyribonucleic) oligonucleotides. Synthesis is commonly performed in a commercially available synthesizer (available, inter alia, from Applied Biosystems). Oligonucleotide synthesis is described for example in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Ann. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et al., in IRL Press 1989 edited by Oliver R. W. A.; Kap. 7: 183-208.

Other synthetic procedures are known in the art, e.g. the procedures described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

In some embodiments the oligonucleotides disclosed herein are synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the modified dsRNA molecules disclosed herein, two or more such sequences can be synthesized and linked together for use.

In various embodiments some of the dsRNA molecules possess a terminal moiety covalently bound at the 5'-terminus of the antisense strand which is mismatched to a nucleotide in a target mRNA. In some embodiments of Structure (A2), $N^1$ (5' terminal nucleotide) in the antisense strand and/or $N^2$ (3' terminal nucleotide) of sense strand are substituted to generate the modified double-stranded RNA compounds. In various embodiments the moiety at the 5'-terminus of the antisense strand is selected from the group consisting of ribouridine, deoxyribouridine, modified ribouridine, modified deoxyribouridine, deoxyribothymidine, modified deoxyribothymidine, ribocytosine, an adenine PT analogue and the moiety at the 3'-terminus of the sense strand is selected from a ribonucleotide or a modified ribonucleotide or an unconventional moiety. The structures disclosed are beneficially applied to double-stranded RNA useful in inhibiting or attenuating mammalian and non-mammalian gene expression.

In one embodiment, provide are double-stranded ribonucleic acid (e.g. dsRNA or siRNA), which down-regulate the expression of mammalian or non-mammalian target genes. The double-stranded ribonucleic acid molecules comprise at least one TNA on the sense strand and/or the antisense strand. In some embodiments the sense strand comprises a nucleotide sequence derived from the target RNA sequence, and the antisense strand is complementary to the sense strand. In general, some deviation from the target mRNA sequence is tolerated without compromising the siRNA activity (see e.g. Czauderna et al., 2003, NAR 31(11), 2705-2716). A dsRNA of the invention inhibits gene expression on a post-transcriptional level with or without destroying the mRNA. Without being bound by theory, dsRNA may target the mRNA for specific cleavage and degradation and/or may inhibit translation from the targeted message.

In one aspect, provided are ribonucleic acid molecules in which a) the ribonucleic acid molecule includes a sense strand and an antisense strand; b) each strand is independently 15 to 49 nucleotides in length; (c) a 15 to 49 nucleotide sequence of the antisense strand is complementary to a sequence of a target RNA; d) at least one of the sense strand or antisense strand includes a TNA moiety; and e) 15 to 49 nucleotide sequence of the sense strand is complementary to the a sequence of the antisense strand and includes a 15 to 49 nucleotide sequence of a target RNA.

In some embodiments the antisense strand and the antisense strand are the same length. In some embodiments the antisense strand and the sense strand are 18-25 or 18-23 or 18-21 or 19-21 or 19 nucleotides in length.

In some embodiments the antisense strand includes a threose nucleic acid moiety in at least one of positions 5, 6, 7, 8, or 9 from the 5' terminus; and/or the sense strand includes a threose nucleic acid moiety in at least one of positions 9 or 10 from the 5' terminus; and/or the sense strand includes from 1 to 10 threose nucleic acid moieties at the 3' terminal or penultimate positions.

In some embodiments the antisense strand includes a threose nucleic acid moiety, in at least one of positions 5, 6, 7, 8, or 9 from the 5' terminus; and the sense strand includes a threose nucleic acid moiety, a 2'5' linked nucleotide or a pseudoUridine in at least one of positions 9 or 10 from the 5' terminus; and the sense strand includes from 1 to 10 threose nucleic acid moieties at the 3' terminal or penultimate positions.

In some embodiments the antisense strand includes a threose nucleic acid moiety, in at least one of positions 5, 6, 7, 8, or 9 from the 5' terminus; and the sense strand includes a threose nucleic acid moiety, a 2'5' linked nucleotide or a pseudoUridine in at least one of positions 9 or 10 from the 5' terminus; and the sense strand includes from 4 to 6 2'5' linked nucleotides at the 3' terminal or penultimate positions.

In some embodiments the antisense strand includes a threose nucleic acid moiety, a 2'5' linked nucleotide or a mirror nucleotide in at least one of positions 5, 6, 7, 8, or 9 from the 5' terminus; and the sense strand includes a threose nucleic acid moiety in at least one of positions 9 or 10 from the 5' terminus; and/or the sense strand includes from 1 to 10 threose nucleic acid moieties or 4-6 2'5' linked nucleotides at the 3' terminal or penultimate positions.

Pharmaceutical Compositions

While it is possible for the nucleic acid molecules disclosed herein to be administered as the compound per se (i.e. as naked dsRNA), or as pharmaceutically acceptable salt of the compound per se, it is preferable to present them as a pharmaceutical composition. Accordingly, provided herein is a pharmaceutical composition comprising one or more of the modified dsRNA molecules disclosed herein; and a pharmaceutically acceptable carrier. Further, provided herein is a pharmaceutical composition comprising one or more of the modified dsRNA molecules disclosed herein in a for of a pharmaceutically acceptable salt; and a pharmaceutically acceptable carrier. In some embodiments the pharmaceutical composition comprises two or more modified dsRNA molecules disclosed herein, or pharmaceutically acceptable salts thereof.

Further provided are pharmaceutical compositions comprising at least one ribonucleic acid molecule disclosed herein covalently or non-covalently bound to one or more nucleic acid molecule disclosed herein in an amount effective to inhibit/down-regulate a target gene expression; and a pharmaceutically acceptable carrier. The molecule may be processed intracellularly by endogenous cellular complexes to produce one or more nucleic acid molecules disclosed herein (for example a 38 mer duplex may be processed into two 19 mer duplexes).

Further provided are pharmaceutical compositions comprising a pharmaceutically acceptable carrier and one or more of the nucleic acid compounds disclosed herein in an amount effective to down-regulate expression in a cell of a target gene, e.g. a double-stranded RNA compound comprising an antisense strand the sequence of which is substantially complementary to a consecutive sequence in a target RNA In some embodiments the target gene is a mammalian gene. In some embodiments the target gene is a non-mammalian gene.

In some embodiments, the modified dsRNA molecules disclosed herein or pharmaceutically acceptable salts thereof are the main active component in a pharmaceutical composition. In other embodiments the modified dsRNA molecules disclosed herein or pharmaceutically acceptable salts thereof are one of the active components of a pharmaceutical composition containing two or more therapeutic agents. In some embodiments, said pharmaceutical composition is further being comprised of one or more dsRNA molecules which down-regulate one or more target genes.

Further provided is a process of preparing a pharmaceutical composition, which comprises: providing one or more modified dsRNA molecules disclosed herein or a pharmaceutically acceptable salt thereof; and admixing said compound with a pharmaceutically acceptable carrier.

In a preferred embodiment, the modified dsRNA molecules disclosed herein or a pharmaceutically acceptable salt thereof, used in the preparation of a pharmaceutical composition, is admixed with a carrier in a pharmaceutically effective dose. In some embodiments the modified dsRNA molecules disclosed herein may be conjugated to a steroid or to a lipid or to another suitable molecule e.g. to cholesterol, vitamin A, vitamin E, etc.

Also provided are kits, containers and formulations that include a nucleic acid molecule as provided herein or a pharmaceutically acceptable salt thereof, for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. In one embodiment, the container holds a nucleic acid molecule as disclosed herein. Kits may further include associated indications and/or directions; reagents and other compositions or tools used for such purpose can also be included.

The container can alternatively hold a composition comprising an active agent that is effective for treating, diagnosis, prognosing or prophylaxing a condition and can have a sterile access port (for example the container can be an intravenous solution bag or a vial having a stopper pierceable by a hypodermic injection needle). The active agents in the composition can be a single stranded or double-stranded nucleic acid molecule as disclosed herein or a pharmaceutically acceptable salt thereof.

A kit may further include a second container that includes a pharmaceutically-acceptable buffer and may further include other materials desirable from a commercial and user standpoint, including other buffers, diluents, filters, stirrers, needles, syringes, and/or package inserts with indications and/or instructions for use.

The container holding the nucleic acid molecule may include a package that is labeled, and the label may bear a notice in the form prescribed by a governmental agency, for example the Food and Drug Administration, which notice is reflective of approval by the agency under Federal law, of the manufacture, use, or sale of the nucleic acid molecule therein for human administration.

A dsRNA molecule can be assembled from two separate oligonucleotide strands, where one strand is the sense strand and the other is the antisense strand in which the antisense and sense strands are self-complementary (i.e. each strand includes nucleotide sequence that is complementary to nucleotide sequence in the other strand); such as where the antisense strand and sense strand form a duplex or double-stranded structure having any length and structure as described herein for nucleic acid molecules as provided, for example wherein the double-stranded region (duplex region) is about 17 to about 40 (e.g., about 17, 18, 19, 20, 21, 22, 23, 24, 25, 26, 27, 28, 29, 30, 31, 32, 33, 34, 35, 36, 37, 38, 39, or 40 base pairs); the antisense strand includes nucleotide sequence that is complementary to nucleotide sequence in a target nucleic acid molecule or a portion thereof and the sense strand includes nucleotide sequence corresponding to the target nucleic acid sequence or a portion thereof (e.g., about 17 to about 40 or more nucleotides of the nucleic acid molecules herein are complementary to the target nucleic acid or a portion thereof).

In certain aspects and embodiments a double-stranded nucleic acid molecule (e.g., a siNA molecule) provided herein may be a "RISC length" molecule or may be a Dicer substrate as described in more detail below.

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol Biol.; 2004, 252:457-69; Levenkova et al., Bioinform. 2004, 20(3):430-2; Ui-Tei et al., NAR. 2004, 32(3):936-48; De Paula et al., RNA 2007, 13:431-56).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107,094, describe chemically modified oligomers. US Patent Publication Nos. 2005/0080246 and 2005/0042647 relate to oligomeric compounds having an alternating motif and nucleic acid molecules having chemically modified internucleoside linkages, respectively.

Other modifications have been disclosed. The inclusion of a 5'-phosphate moiety was shown to enhance activity of siRNAs in *Drosophila* embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-OMethyl modifications. Holen et al (NAR. 2003, 31(9): 2401-07) report that an siRNA having small numbers of 2'-OMethyl modified nucleosides gave good activity compared to wild type but that the activity decreased as the numbers of 2'-OMethyl modified nucleosides was increased. Chiu and Rana (RNA. 2003, 9:1034-48) describe that incorporation of 2'-OMethyl modified nucleosides in the sense or antisense strand (fully modified strands) severely reduced siRNA activity relative to unmodified siRNA. The placement of a 2'-OMethyl group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the disclosed herein offer an advantage in that they are stable and active and are useful in the preparation of pharmaceutical compositions for treatment of various diseases.

PCT Patent Publication Nos. WO 2008/104978, WO 2009/044392, WO 2011/066475 and WO 2011/084193 to a co-assignee of the present disclosure and hereby incorporated by reference in their entirety, disclose dsRNA structures.

PCT Publication No. WO 2008/050329 and U.S. Ser. No. 11/978,089 to a co-assignee of the present disclosure relate to inhibitors of pro-apoptotic genes, and are incorporated by reference in their entirety.

PCT Patent Publication Nos. WO 2004/111191 and WO 2005/001043 relate to methods for enhancing RNAi.

Provided herein is a method of down-regulating the expression of a target gene by at least 20%, 30%, 40% or 50% as compared to a control, comprising contacting an mRNA transcript of the target gene with one or more of the compounds disclosed herein.

Additionally provided herein is a method of down-regulating the expression of a target gene in a mammal by at least 20%, 30%, 40% or 50% as compared to a control, comprising administering one or more of the dsRNA molecules disclosed herein to the mammal. In a preferred embodiment the mammal is a human.

In various embodiments a double-stranded nucleic acid molecule according to Structure (A1) or Structure (A2) is down-regulating the expression of a target gene, whereby the down-regulation of the expression of a target gene is selected from the group comprising down-regulation of gene function (which is examined, e.g. by an enzymatic assay or a binding assay with a known interactor of the native gene/polypeptide, inter alia), down-regulation of polypeptide product of the gene (which is examined, e.g. by Western blotting, ELISA or immuno-precipitation, inter alia) and down-regulation of mRNA expression of the gene (which is examined, e.g. by Northern blotting, quantitative RT-PCR, in-situ hybridization or microarray hybridization, inter alia).

Dosages

The useful dosage to be administered and the particular mode of administration of the compounds and compositions provided herein will vary depending upon such factors as the cell type, or for in vivo use, the age, weight and the particular subject and region thereof to be treated, the particular nucleic acid and delivery method used, the therapeutic or diagnostic use contemplated, and the form of the formulation, for example, naked dsRNA, suspension, emulsion, micelle or liposome, as will be readily apparent to those skilled in the art. Typically, dosage is administered at lower levels and increased until the desired effect is achieved.

When lipids are used to deliver the nucleic acid, the amount of a lipid compound that is administered can vary and generally depends upon the amount of nucleic acid being administered. For example, the weight ratio of a lipid compound to a nucleic acid is preferably from about 1:1 to about 30:1, with a weight ratio of about 5:1 to about 10:1 being more preferred.

A "therapeutically effective dose" for purposes herein is determined by considerations as are known in the art. The dose must be effective to achieve improvement including but not limited to improved survival rate or more rapid recovery, or improvement or alleviation or elimination of symptoms and other indicators as are selected as appropriate measures by those skilled in the art. The dsRNA molecules or pharmaceutical compositions disclosed herein can be administered in a single dose or in multiple doses.

A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day.

Suitable amounts of nucleic acid molecules may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

An appropriate dosage for a mammal may be from 0.01 ug to 1 g per kg of body weight (e.g., 0.1 ug, 0.25 ug, 0.5 ug, 0.75 ug, 1 ug, 2.5 ug, 5 ug, 10 ug, 25 ug, 50 ug, 100 ug, 250 ug, 500 ug, 1 mg, 2.5 mg, 5 mg, 10 mg, 25 mg, 50 mg, 100 mg, 250 mg, or 500 mg per kg).

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 0.1 mg to about 500 mg of an active ingredient. Dosage units may be adjusted for local delivery, for example for intravitreal delivery of for transtympanic delivery.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Pharmaceutical compositions that include the ribonucleic acid molecule disclosed herein may be administered once daily, qid, tid, bid, QD, or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of nucleic acids together contains a sufficient dose.

Delivery

The modified dsRNA molecules disclosed herein are administered as the compound per se (i.e. as naked siRNA) or as pharmaceutically acceptable salt and are administered alone or as an active ingredient in combination with one or more pharmaceutically acceptable carrier, solvent, diluent, excipient, adjuvant and vehicle. In some embodiments, the dsRNA molecules are delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

Pharmaceutically acceptable carriers, solvents, diluents, excipients, adjuvants and vehicles as well as implant carriers generally refer to inert, non-toxic solid or liquid fillers, diluents or encapsulating material not reacting with the active modified dsRNA molecules disclosed herein and they include liposomes and microspheres. For example, the dsRNA molecules disclosed herein may be formulated with polyethylenimine (PEI), with PEI derivatives, e.g. oleic and stearic acid modified derivatives of branched PEI, with chitosan or with poly(lactic-co-glycolic acid) (PLGA). Formulating the compositions in e.g. liposomes, micro- or nano-spheres and nanoparticles, may enhance stability and benefit absorption.

Additionally, the compositions may include an artificial oxygen carrier, such as perfluorocarbons (PFCs) e.g. perfluorooctyl bromide (perflubron).

Examples of delivery systems useful in conjunction with the dsRNA molecules disclosed herein include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many such implants, delivery systems, and modules are well known to those skilled in the art. In one specific embodiment topical and transdermal formulations are selected.

Accordingly, in some embodiments the dsRNA molecules disclosed herein are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed (see, for example, Shen et al FEBS Let. 539: 111-114 (2003), Xia et al., Nat. Biotech. 20: 1006-1010 (2002), Reich et al., Mol. Vision 9: 210-216 (2003), Sorensen et al., J. Mol. Biol. 327: 761-766 (2003), Lewis et al., Nat. Gen. 32: 107-108 (2002) and Simeoni et al., NAR 31, 11: 2717-2724 (2003)). siRNA has been successfully used for inhibition of gene expression in primates.

Additional formulations for improved delivery of the compounds disclosed herein can include non-formulated compounds, compounds covalently bound to cholesterol, and compounds bound to targeting antibodies (Song et al., Antibody mediated in vivo delivery of small interfering RNAs via cell-surface receptors, Nat Biotechnol. 2005. 23(6):709-17). Cholesterol-conjugated siRNAs (and other steroid and lipid conjugated siRNAs) can been used for delivery (see for example Soutschek et al Nature. 2004. 432:173-177; and Lorenz et al. Bioorg. Med. Chem. Lett. 2004. 14:4975-4977).

The naked siRNA or the pharmaceutical compositions comprising the chemically modified dsRNA disclosed herein are administered and dosed in accordance with good medical practice, taking into account the clinical condition of the individual patient, the disease to be treated, the site and method of administration, scheduling of administration, patient age, sex, body weight and other factors known to medical practitioners.

The modified dsRNA molecules disclosed herein can be administered by any of the conventional routes of administration. The modified dsRNA molecules are administered orally, subcutaneously or parenterally including intravenous, intraarterial, intramuscular, intraperitoneally, intraocular, ocular, otic, transtympanic and intranasal administration, intratracheal instillation and intratracheal inhalation, as well as infusion techniques. Implants of the compounds are also useful.

Liquid forms are prepared for invasive administration, e.g. injection or for topical or local or non-invasive administration. The term injection includes subcutaneous, transdermal, intravenous, intramuscular, intrathecal, intraocular, transtympanic and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration.

In some embodiments the compounds disclosed herein are formulated for non-invasive administration. In some embodiments the compounds disclosed herein are formulated as eardrops for topical administration to the ear. In some embodiments the dsRNA molecules disclosed herein are formulated as eye drops for topical administration to the surface of the eye. Further information on administration of the dsRNA molecules disclosed herein can be found in Tolentino et al., Retina 2004. 24:132-138; and Reich et al., Molecular Vision, 2003. 9:210-216. In addition, in certain embodiments the compositions disclosed herein are formed as aerosols, for example for intranasal administration. In certain embodiments the compositions disclosed herein are formed as nasal drops, for example for intranasal instillation. In some embodiments the compositions are formulated as ear drops.

The therapeutic compositions disclosed herein are preferably administered into the lung by inhalation of an aerosol containing these compositions/compounds, or by intranasal or intratracheal instillation of said compositions. For further information on pulmonary delivery of pharmaceutical compositions see Weiss et al., Human Gene Therapy 1999. 10:2287-2293; Densmore et al., Molecular therapy 1999. 1:180-188; Gautam et al., Molecular Therapy 2001. 3:551-556; and Shahiwala & Misra, AAPS PharmSciTech 2004. 24; 6(3):E482-6. Additionally, respiratory formulations for siRNA are described in U.S. Patent Application Publication No. 2004/0063654. Respiratory formulations for siRNA are described in US Patent Application Publication No. 2004/0063654.

In certain embodiments, oral compositions (such as tablets, suspensions, solutions) may be effective for local delivery to the oral cavity such as oral composition suitable for mouthwash for the treatment of oral mucositis.

In a particular embodiment, the modified dsRNA molecules disclosed herein are formulated for intravenous administration for delivery to the kidney for the treatment of kidney disorders, e.g. acute renal failure (ARF), delayed graft function (DGF) and diabetic retinopathy. It is noted that the delivery of the modified dsRNA molecules to the target cells in the kidney proximal tubules is particularly effective in the treatment of ARF and DGF.

Delivery of compounds into the brain is accomplished by several methods such as, inter alia, neurosurgical implants, blood-brain barrier disruption, lipid mediated transport, carrier mediated influx or efflux, plasma protein-mediated transport, receptor-mediated transcytosis, absorptive-mediated transcytosis, neuropeptide transport at the blood-brain barrier, and genetically engineering "Trojan horses" for drug targeting. The above methods are performed, for example, as described in "*Brain Drug Targeting: the future of brain drug development*", W. M. Pardridge, Cambridge University Press, Cambridge, UK (2001).

In addition, in certain embodiments the compositions for use in the treatments disclosed herein are formed as aerosols, for example for intranasal administration.

Intranasal delivery for the treatment of CNS diseases has been attained with acetylcholinesterase inhibitors such as galantamine and various salts and derivatives of galantamine, for example as described in US Patent Application Publication No. 2006003989 and PCT Applications Publication Nos. WO 2004/002402 and WO 2005/102275. Intranasal delivery of nucleic acids for the treatment of CNS diseases, for example by intranasal instillation of nasal drops, has been described, for example, in PCT Application Publication No. WO 2007/107789.

Methods of Treatment

In one aspect provided herein is a method of treating a subject at risk of or suffering from a disorder associated with a target gene expression comprising administering to the subject a therapeutically effective amount of a modified dsRNA molecule disclosed herein or a pharmaceutically acceptable salt thereof. In preferred embodiments the subject being treated is a warm-blooded animal and, in particular, mammal including human. Further provided is use of a dsRNA molecule disclosed herein or a pharmaceutically acceptable salt thereof for manufacture of a medicament for use in therapy.

"Treating a subject" refers to administering to the subject a therapeutic substance effective to ameliorate symptoms associated with a disease, to lessen the severity or cure the disease, to slow down the progress of the disease, to prevent the disease from occurring or to postpone the onset of the disease. "Treatment" refers to both therapeutic treatment and prophylactic or preventative measures, wherein the object is to prevent a disorder, to delay the onset of the disorder or reduce the symptoms of a disorder. Those in need of treatment include those already experiencing the disease or condition, those prone to having the disease or condition, and those in which the disease or condition is to be prevented. The compounds disclosed herein are administered before, during or subsequent to the onset of the disease or condition.

A "therapeutically effective dose" refers to an amount of the compound or the pharmaceutical composition which is effective to achieve an improvement in a subject or his physiological systems including, but not limited to, improved survival rate, more rapid recovery, improvement or elimination of symptoms, delayed onset of a disorder, slower progress of disease and other indicators selected as appropriate by those skilled in the art.

"Respiratory disorder" refers to conditions, diseases or syndromes of the respiratory system including but not limited to pulmonary disorders of all types including chronic obstructive pulmonary disease (COPD), emphysema, chronic bronchitis, asthma and lung cancer, inter alia. Emphysema and chronic bronchitis may occur as part of COPD or independently. In various embodiments provided are methods and compositions useful in preventing or treating primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, in a subject in need thereof.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, ischemic optic neuropathy (ION), non-arteritic ischemic optic neuropathy (NAION), anterior ischemic optic neuropathy (AION), optic neuritis (primary or secondary to autoimmune diseases), glaucoma, von Hippel Lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, Birdshot retinochoroidopathy, long-standing retinal detachment; systemic conditions such as Diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, neuropathies, nephropathies, microvascular diseases of the kidney, and ischemic microvascular conditions, inter alia.

Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. In various embodiments all these neovascular conditions are treated using the compounds and pharmaceutical compositions disclosed herein.

"Eye disease" refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases and retinal vein occlusion (RVO). In various embodiments, conditions disclosed herein, such as DR, which are regarded as either a microvascular disorder or an eye disease, or both, under the definitions presented herein, are treated according to the methods disclosed herein.

Fibrotic disorder includes fibrosis of the liver, lung, heart, kidney, bone marrow, eye, and uterine; systemic fibrosis and fibrosis resulting from injury or surgery. Fibrotic disorder includes liver fibrosis, hepatic damage, and liver cirrhosis; pulmonary fibrosis including lung fibrosis (including IPF idiopathic pulmonary fibrosis), any condition causing kidney fibrosis (e.g., CKD including ESRD), peritoneal fibrosis, fibrillogenesis, fibrotic diseases in other organs, abnormal scarring (keloids) associated with all possible types of skin injury accidental and jatrogenic (operations); *scleroderma*; cardiofibrosis, failure of glaucoma filtering operation; and intestinal adhesions.

More specifically, provided herein are methods and compositions useful in treating a subject suffering from or susceptible to adult respiratory distress syndrome (ARDS); Chronic obstructive pulmonary disease (COPD); acute lung injury (ALI); Emphysema; Diabetic Neuropathy, nephropathy and retinopathy; diabetic macular edema (DME) and other diabetic conditions; Glaucoma; age related macular degeneration (AMD); bone marrow transplantation (BMT) retinopathy; ischemic conditions; ocular ischemic syndrome (OIS); kidney disorders: acute renal failure (ARF), delayed graft function (DGF), transplant rejection; hearing disorders (including hearing loss); spinal cord injuries; oral mucositis; dry eye syndrome and pressure sores; neurological disorders arising from ischemic or hypoxic conditions, such as hypertension, hypertensive cerebral vascular disease, a constriction or obstruction of a blood vessel—as occurs in the case of a thrombus or embolus, angioma, blood dyscrasias, any form of compromised cardiac function including cardiac arrest or failure, systemic hypotension; stroke, disease, disorders and injury of the CNS, including, without being limited to, epilepsy, spinal cord injury, brain injury and neurodegenerative disorders, including, without being limited to Parkinson's disease, Amyotrophic Lateral Sclerosis (ALS, Lou Gehrig's Disease), Alzheimer's disease, Huntington's disease and any other disease-induced dementia (such as HIV-associated dementia for example); Ménière's disease; neurological disorders arising from exposure to toxic agents.

Provided herein are nucleic acid compounds, pharmaceutical compositions and methods useful in the treatment of cancer. The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. Other examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkin lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

Additionally, provided is a method of down-regulating the expression of a target gene by at least 20%, 30%, 40% or 50% as compared to a control comprising contacting target mRNA with one or more of the modified dsRNA molecules disclosed herein. In various embodiments the modified dsRNA molecules down-regulates target gene whereby the down-regulation is selected from the group comprising down-regulation of gene function, down-regulation of polypeptide and down-regulation of mRNA expression.

Provide herein is a method of inhibiting the expression of a target gene by at least 20%, 30%, or 40%, preferably by 50%, 60% or 70%, more preferably by 75%, 80% or 90% as compared to a control comprising contacting an mRNA transcript of the target gene with one or more of the dsRNA molecules disclosed herein.

In one embodiment the modified dsRNA molecules disclosed herein inhibit the target gene polypeptide, whereby the inhibition is selected from the group comprising inhibition of function (which is examined by, for example, an enzymatic assay or a binding assay with a known interactor of the native gene/polypeptide, inter alia), inhibition of target protein (which is examined by, for example, Western blotting, ELISA or immuno-precipitation, inter alia) and inhibition of target mRNA expression (which is examined by, for example, Northern blotting, quantitative RT-PCR, in-situ hybridization or microarray hybridization, inter alia).

In additional embodiments provided is a method of treating a subject suffering from or susceptible to any disease or disorder accompanied by an elevated level of a mammalian or a non-mammalian target gene, the method comprising administering to the subject a modified dsRNA molecule disclosed herein, or a pharmaceutically acceptable salt thereof, in a therapeutically effective dose thereby treating the subject.

Provided herein are double-stranded nucleic acid molecules for use in therapy, in particular for use where down-regulation of expression of a mammalian or non-mammalian target gene is beneficial.

By "exposure to a toxic agent" is meant that the toxic agent is made available to, or comes into contact with, a mammal. A toxic agent can be toxic to the nervous system. Exposure to a toxic agent can occur by direct administration, e.g., by ingestion or administration of a food, medicinal, or therapeutic agent, e.g., a chemotherapeutic agent, by accidental contamination, or by environmental exposure, e g., aerial or aqueous exposure.

In other embodiments the chemically modified dsRNA molecules and methods disclosed herein are useful for treating or preventing the incidence or severity of other diseases and conditions in a subject. These diseases and conditions include, but are not limited to stroke and stroke-like situations (e.g. cerebral, renal, cardiac failure), neuronal cell death, brain injuries with or without reperfusion, spinal cord injury, chronic degenerative diseases e.g. neurodegenerative disease including, Alzheimer's disease, Parkinson's disease, Huntington's disease, multiple sclerosis, spinobulbar atrophy, prion disease and apoptosis resulting from traumatic brain injury (TBI). In an additional embodiment, the compounds and methods disclosed herein are directed to providing neuroprotection, and/or cerebroprotection.

Without limitation a mammalian target gene is selected from the group consisting of p53 (TP53), TP53BP2, LRDD, CYBA, ATF3, CASP2 (Caspase 2), NOX3, HRK; C1QBP, BNIP3, MAPK8; Rac1, GSK3B, CD38, STEAP4, BMP2a; GJA1, TYROBP, CTGF, SPP1, RTN4R, ANXA2, RHOA, DUOX1, SLC5A1, SLC2A2, AKR1B1, SORD, SLC2A1, MME, NRF2, SRM, REDD2 (RTP801L), REDD1 (RTP801), NOX4, MYC, PLK1, ESPL1, HTRA2, KEAP1, p66, ZNHIT1, LGALS3, CYBB (NOX2), NOX1, NOXO1, ADRB1, HI 95, ARF1, ASPP1, SOX9, FAS, FASLG, Human MLL, AF9, CTSD, CAPNS1, CD80, CD86, HES1, HES5, HEY1, HEY2, CDKN1B (p27), ID1, ID2, ID3, CDKN2A, Caspase 1, Caspase 3, Caspase 4, Caspase 5, Caspase 6, Caspase 7, Caspase 8, Caspase 9, Caspase 10, Caspase 12, Caspase 14, Apaf-1, Nod1, Nod2, Ipaf, DEF-CAP, RAIDD, RICK, Bcl10, ASC, TUCAN, ARC, CLARP, FADD, DEDD, DEDD2, Cryopirin, PYC1, Pyrin, TRADD, UNC5a, UNC5b, UNC5c, ZUD, p84N5, LRDD, CDK1, CDK2, CDK4, CDK5, CDK9, PITSLRE A, CHK2, LATS1, Prk, MAP4K1, MAP4K2, STK4, SLK, GSK3alpha, GSK3beta, MEKK1, MAP3K5 (Ask1), MAP3K7, MAP3K8, MAP3K9, MAP3K10, MAP3K11, MAP3K12, DRP-1, MKK6, p38, JNK3, DAPK1, DRAK1, DRAK2, IRAK, RIP, RIP3, RIPS, PKR, IRE1, MSK1, PKCalpha, PKCbeta, PKCdelta, PKCepsilon, PKCeta, PKCmu, PKCtheta, PKCzeta, CAMK2A, HIPK2, LKB1, BTK, c-Src, FYN, Lck, ABL2, ZAP70, TrkA, TrkC, MYLK, FGFR2, EphA2, AATYK, c-Met, RET, PRKAA2, PLA2G2A, SMPD1, SMPD2, SPP1, FAN, PLCG2, IP6K2, PTEN, SHIP, AIF, AMID, Cytochrome c, Smac, HtrA2, TSAP6, DAP-1, FEM-, DAP-3, Granzyme B, DIO-1, DAXX, CAD, CIDE-A, CIDE-B, Fsp27, Ape1, ERCC2, ERCC3, BAP31, Bit1, AES, Huntingtin, HIP1, hSir2, PHAP1, GADD45b, GADD34, RAD21, MSH6, ADAR, MBD4, WW45, ATM, mTOR, TIP49, diubiquitin/FAT10, FAF1, p193, Scythe/BAT3, Amida, IGFBP-3, TDAG51, MCG10, PACT, p52/RAP, ALG2, ALG3, presenelin-1, PSAP, AIP1/Alix, ES18, mda-7, p14ARF, ANTI, p33ING1, p33ING2, p53AIP1, p53DINP1, MGC35083, NRAGE, GRIM19, lipocalin 2, glycodelin A, NADE, Porimin, STAG1, DAB2, Galectin-7, Galectin-9, SPRC, F1121908, WWOX, XK, DKK-1, Fzd1, Fzd2, SARP2, axin 1, RGS3, DVL1, NFkB2, IkBalpha, NF-ATC1, NF-ATC2, NF-ATC4, zf3/ZNF319, Egr1, Egr2, Egr3, Sp1, TIEG, WT1, Zac1, Icaros, ZNF148, ZK1/ZNF443, ZNF274, WIG1, HIVEP1, HIVEP3, Fliz1, ZPR9, GATA3, TR3, PPARG, CSMF, RXRa, RARa, RARb, RARg, T3Ra, Erbeta, VDR, GR/GCCR, p53, p73alpha, p63(human [ta alpha, ta beta, ta gamma, da alpha, a beta, da gamma], 53BP2, ASPP1, E2F1, E2F2, E2F3, HIF1 alpha, TCF4, c-Myc, Max, Mad, MITF, Id2, Id3, Id4, c-Jun, c-Fos, ATF3, NF-IL6, CHOP, NRF1, c-Maf, Bach2, Msx2, Csx, Hoxa5, Ets-1, PU1/Spi1, Ets-2, ELK1, TEL1, c-Myb, TBX5, IRF1, IRF3, IRF4, IRF9, AP-2 lpha, FKHR, FOXO1A, FKHRL1, FOXO3a, AFX1, MLLT7, Tip60, BTG1, AUF1, HNRPD, TIA1, NDG1, PCBP4, MCG10, FXR2, TNFR2, LTbR, CD40, CD27, CD30, 4-1BB, TNFRSF19, XEDAR, Fn14, OPG, DcR3, FAS, TNFR1, WSL-1, p75NTR, DR4, DR5, DR6, EDAR, TNF 1pha, FAS ligand, TRAIL, Lymphotoxin alpha, Lymphotoxin beta, 4-1BBL, RANKL, TL1, TWEAK, LIGHT, APRIL, IL-1-alpha, IL-1-beta, IL-18, FGF8, IL-2, IL-21, IL-5, IL-4, IL-6, LIF, IL-12, IL-7, IL-10, IL-19, IL-24, IFN alpha, IFN beta, IFN gamma, M-CSF, Prolactinm, TLR2, TLR3, TLR4, MyD88, TRIF, RIG-1, CD14, TCR alpha, CD3 gamma, CD8, CD4, CD7, CD19, CD28, CTLA4, SEMA3A, SEMA3B, HLA-A, HLA-B, HLA-L, HLA-Dmalpha, CD22, CD33, CALL, DCC, ICAM1, ICAM3, CD66a, PVR, CD47, CD2, Thy-1, SIRPa1, CD5, E-cadherin, ITGAM, ITGAV, CD18, ITGB3, CD9, IgE Fc R beta, CD82, CD81, PERP, CD24, CD69, KLRD1, galectin 1, B4GALT1, C1q alpha, C5R1, MIP1alpha, MIP1beta, RANTES, SDF1, XCL1, CCCKR5, OIAS/OAS1, INDO, MxA, IFI16, AIM2, iNOS, HB-EGF, HGF, MIF, TRAF3, TRAF4, TRAF6, PAR-4, IKKGamma, FIP2, TXBP151, FLASH, TRF1, IEX-1S, Dok1, BLNK, CIN85, Bif-1, HEF1, Vav1, RasGRP1, POSH, Rac1, RhoA, RhoB, RhoC, ALG4, SPP1, TRIP, SIVA, TRABID, TSC-22, BRCA1, BARD1, 53BP1, MDC1, Mdm4, Siah-1, Siah-2, RoRet, TRIM35, PML, RFWD1, DIP1, Socs1, PARC, USP7, CYLD, TTR, SERPINH1 (HSP47). Other useful target genes are genes of microbial origin including viral, bacterial, fungal and mycoplasmal genes.

Combination Therapy

The methods of treating the diseases disclosed herein include administering a modified double-stranded nucleic acid molecule disclosed herein in conjunction or in combination with an additional inhibitor, a substance which improves the pharmacological properties of the modified nucleic acid molecule, or an additional compound known to be effective in the treatment of a subject suffering from or susceptible to any of the hereinabove mentioned diseases and disorders.

In another embodiment, provided are pharmaceutical compositions comprising a combination of a therapeutic modified ribonucleic acid molecule disclosed herein together with at least one additional therapeutically active agent. By "in conjunction with" or "in combination with" is meant prior to, simultaneously or subsequent to. Accordingly, the individual components of such a combination are administered either sequentially or simultaneously from the same or separate pharmaceutical formulations.

Combination therapies comprising known treatments for treating microvascular disorders, eye disease and conditions (e.g. macular degeneration), hearing impairments (including hearing loss), respiratory disorders, kidney disorders, organ transplantation, neurodegenerative disorders (e.g. spinal cord injury), angiogenesis- and apoptosis-related conditions, in conjunction with the modified nucleic acid molecules and therapies described herein are considered part of the current invention.

Accordingly, in another embodiment, an additional pharmaceutically effective compound is administered in conjunction with the pharmaceutical composition disclosed herein. In addition, the modified ribonucleic acid molecules disclosed herein are used in the preparation of a medicament for use as adjunctive therapy with a second therapeutically active compound to treat such conditions. Appropriate doses of known second therapeutic agents for use in combination with a chemically modified nucleic acid molecule disclosed herein are readily appreciated by those skilled in the art.

In some embodiments the combinations referred to above are presented for use in the form of a single pharmaceutical formulation.

The administration of a pharmaceutical composition comprising any one of the pharmaceutically active dsRNA disclosed herein is carried out by any of the many known routes of administration, including intravenously, intra-arterially, subcutaneously, intraperitoneally or intra-cerebrally, as determined by a skilled practitioner. Using specialized formulations, it is possible to administer the compositions orally or via inhalation or via intranasal instillation. In some embodiments a dsRNA molecule disclosed herein is formulated for topical administration, including as eardrops, eye drops, dermal formulation, transdermal formulation and the like.

By "in conjunction with" is meant that the additional pharmaceutically effective compound is administered prior to, at the same time as, or subsequent to administration of the molecules or the pharmaceutical compositions disclosed herein. The individual components of such a combination referred to above, therefore, can be administered either sequentially or simultaneously from the same or separate pharmaceutical formulations. As is the case for the present modified siRNA compounds, a second therapeutic agent can be administered by any suitable route, for example, by oral, buccal, inhalation, sublingual, rectal, vaginal, transurethral, nasal, otic, ocular, topical, percutaneous (i.e., transdermal), or parenteral (including intravenous, intramuscular, subcutaneous, and intracoronary) administration.

In some embodiments, a modified ribonucleic acid molecule disclosed herein and a second therapeutic agent (dsRNA or other) are administered by the same route, either provided in a single composition as two or more different pharmaceutical compositions. However, in other embodiments, a different route of administration for the modified nucleic acid molecule disclosed herein and the second therapeutic agent is either possible or preferred. Persons skilled in the art are aware of the best modes of administration for each therapeutic agent, either alone or in combination.

In various embodiments, the modified ribonucleic acid molecules disclosed herein are the main active component in a pharmaceutical composition.

In another aspects, provided are pharmaceutical compositions comprising two or more dsRNA molecules for the treatment of a disease and for any of the diseases and conditions mentioned herein. In some embodiments the two or more dsRNA molecules or formulations comprising said molecules are admixed in the pharmaceutical composition in amounts that generate equal or otherwise beneficial activity. In certain embodiments the two or more siRNA molecules are covalently or non-covalently bound, or joined together by a nucleic acid linker of a length ranging from 2-100, preferably 2-50 or 2-30 nucleotides.

In some embodiments the pharmaceutical compositions of the invention further comprise one or more additional dsRNA molecule, which targets one or more additional gene. In some embodiments, simultaneous inhibition of said additional gene(s) provides an additive or synergistic effect for treatment of the diseases disclosed herein.

The treatment regimen according to the invention is carried out, in terms of administration mode, timing of the administration, and dosage, so that the functional recovery of the patient from the adverse consequences of the conditions disclosed herein is improved or so as to postpone the onset of a disorder. The treatment regimen according to the invention is carried out, in terms of administration mode, timing of the administration, and dosage, so that the functional recovery of the patient from the adverse consequences of the conditions disclosed herein is improved or so as to postpone the onset of a disorder. The amount of active ingredient that can be combined with a carrier to produce a single dosage form varies depending upon the host treated and the particular mode of administration. Dosage unit forms generally contain between from about 0.1 mg to about 500 mg of an active ingredient. Dosage units may be adjusted for local delivery, for example for intravitreal delivery of for transtympanic delivery.

RNA Interference and siNA Molecules

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is often referred to as post-transcriptional gene silencing (PTGS) or RNA silencing. The process of post-transcriptional gene silencing is thought to be an evolutionarily-conserved cellular defense mechanism used to prevent the expression of foreign genes (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double-stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898,031; Clemens et al., 1997, J. Interferon & Cytokine Res., 17, 503-524; Adah et al., 2001, Curr. Med. Chem., 8, 1189).

The presence of long dsRNAs in cells stimulates the activity of a ribonuclease III enzyme referred to as "dicer" (Bass, 2000, Cell, 101, 235; Zamore et al., 2000, Cell, 101, 25-33; Hammond et al., 2000, Nature, 404, 293). Dicer is involved in the processing of the dsRNA into short dsRNA pieces known as siNA or siRNA (Zamore et al., 2000, Cell, 101, 25-33; Bass, 2000, Cell, 101, 235; Berstein et al., 2001, Nature, 409, 363). Short interfering RNAs derived from dicer activity are typically about 21 to about 23 nucleotides in length and include about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in *C. elegans*. Bahramian and Zarbl, 1999, Molecular and Cellular Biology, 19, 274-283 and Wianny and Goetz, 1999, Nature Cell Biol., 2, 70, describe RNAi mediated by dsRNA in mammalian systems. Hammond et al., 2000, Nature, 404, 293, describe RNAi in *Drosophila* cells transfected with dsRNA. Elbashir et al., 2001, Nature, 411, 494 and Tuschl et al., International PCT Publication No. WO 01/75164, describe RNAi induced by introduction of duplexes of synthetic 21-nucleotide RNAs in cultured mammalian cells including human embryonic kidney and HeLa cells. Research in *Drosophila* embryonic lysates (Elbashir et al., 2001, EMBO J., 20, 6877 and Tuschl et al., International PCT Publication No. WO 01/75164) has revealed certain requirements for siRNA length, structure, chemical composition, and sequence that are essential to mediate efficient RNAi activity.

Nucleic acid molecules (for example having structural features as disclosed herein) may inhibit or down regulate gene expression or viral replication by mediating RNA interference "RNAi" or gene silencing in a sequence-specific manner; see e.g., Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Mello and Fire, International PCT Publication No. WO 01/29058; Li et al., International PCT Publication No. WO 00/44914; Hutvagner and Zamore, 2002, Science, 297, 2056-60; McManus et al., 2002, RNA, 8, 842-850.

The invention has been described in an illustrative manner, and it is to be understood that the terminology used is intended to be in the nature of words of description rather than of limitation.

Modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al., Blood 1996, 87:3822.) Methods of performing RT-PCR are also well known in the art.

Example 1. Generation of Sense Strand and Antisense Strand Sequences for dsRNAs to Target Genes and Production of the Modified Nucleic Acid Molecules Using proprietary algorithms and the known sequence of a target gene, 18 and 19-mer sequences for potential dsRNAs are generated. The antisense strand sequences generated using this method are fully or substantially complementary to a portion of a target mRNA sequence. In some embodiments the antisense sequence is fully complementary to a portion of a corresponding consecutive mRNA sequence. For generating some of the modified nucleic acid molecules disclosed herein, the nucleotide at the 5' terminal position (5' terminus) of the antisense strand (N)x (position 1; $N^1$) is substituted to generate a double-stranded nucleic acid molecule of embodiments of general structure (A2). In other examples, the nucleotide at the 5' terminus of the antisense strand (N)x and the nucleotide at the 3' terminal position (3' terminus) of the sense strand (N')y were substituted to generate the double-stranded nucleic acid molecule of embodiments of Structure A2.

In general, the double-stranded nucleic acid molecules having specific sequences that are selected for in vitro testing are specific for human and a second species such as rat, mouse non-human primate or rabbit genes.

The exemplary compounds target Rac1 (*Homo sapiens* ras-related C3 botulinum toxin substrate 1 (rho family, small GTP binding protein Rac1)), transcript variant Rac1, mRNA) gi|156071503|ref|NM_006908.4| SEQ ID NO:1; jellyfish EGFP (Enhanced Green Fluorescent Protein), SEQ ID NO:2; *Homo sapiens* v-Ki-ras2 Kirsten rat sarcoma viral oncogene homolog (KRAS), transcript variant a, mRNA gi|34485724|ref|NM_033360.2| SEQ ID NO:3; *Homo sapiens* v-Ki-ras2 Kirsten rat sarcoma viral oncogene homolog (KRAS), transcript variant b, mRNA gi|34485723|ref|NM_004985.3| SEQ ID NO:4; and *Homo sapiens* polo-like kinase 1 (*Drosophila*) (PLK1), mRNAgi|34147632|ref|NM_005030.3| SEQ ID NO:5. The dsRNA molecules and target genes utilized in the examples set forth herein are exemplary only. The modifications described herein are applicable to dsRNA molecules targeting any gene.

Polynucleotide sequences of target RNA sequences of mammalian and non-mammalian target genes are available, for example, on the NCBI web site [http://www.ncbi.nlm.nih.gov/].

Example 2. In Vitro Testing of Modified dsRNA Molecules

Use of the PT Phosphoramidites in Oligonucleotide Synthesis

Pyrazolotriazolyl nucleoside analogues of the general formula I, as well as single-stranded oligonucleotides and double-stranded DNA oligonucleotides comprising them, are disclosed in U.S. Provisional Application No. 61/653,528 entitled: "Pyrazolotriazolyl nucleoside analogues and oligonucleotides comprising them", filed on May 31, 2012 and assigned to Bio-Lab Ltd., Israel, a co-assignee in the present application.

The synthesis of dsRNA oligonucleotides disclosed herein, including chimeric oligonucleotides which include RNA, modified RNA (i.e. 2'-OMethyl, 2'-O-methoxyethyl (2'MOE)) and pyrazolotriazolyl (PT) nucleosides was carried out using established solid phase synthesis methods, with some modifications to optimize the coupling yields.

The PT phosphoramidites were incorporated into oligonucleotides, in particular into antisense strands and sense strands useful in generating double-stranded RNA nucleic acid molecules, including siRNA and siNA. Applicants have shown that a dsRNA comprising at least one PT nucleotide analogue imparts serum and cell extract stability and target specificity, compared to an similarly modified dsRNA molecules without PT nucleotide analogues.

Table A hereinbelow, provides sense strands and antisense strands useful in generating dsRNA molecules. Tables B-D provide control dsRNA molecules, dsRNA molecules with at least one PT ribonucleotide analogue and dsRNA molecules with at least one PT deoxynucleotide analogue, respectively. Table E provides the legend for the sense strands and antisense strands.

TABLE A

Nucleotide sequences of sense and antisense strands
utilized to generate dsRNA molecules

| | Sense strand (5'>3') | SEQ ID NO | Antisense strand (5'>3') | SEQ ID NO |
|---|---|---|---|---|
| RAC1_28 | CGUGCAAAGUGGUAUCCUA | 6 | UAGGAUACCACUUUGCACG | 7 |
| EGFP_1 | GCCACAACGUCUAUAUCAU | 8 | AUGAUAUAGACGUUGUGGC | 9 |
| EGFP_2 | GCAUCGAGCUGAAGGGCAU | 10 | AUGCCCUUCAGCUCGAUGC | 11 |
| KRAS_2 | GUAAGGCAGACCCAGUAUA | 12 | UAUACUGGGUCUGCCUUAC | 13 |
| PLK_28 | AGAAGAUGCUUCAGACAGU | 14 | ACUGUCUGAAGCAUCUUCU | 15 |

TABLE B

Control dsRNA molecules

| Name | Length | Sense 5'>3' | Antisense 5'>3' |
|---|---|---|---|
| EGFP_1_S500 | 19 | rG;mC;rC;mA;rC;mA;rA;mC;rG;mU;rC;mU;rA;mU;rA;mU;rC;mA;rU | mA;rU;mG;rA;mU;rA;mU;rA;mG;rA;mC;rG;mU;rU;mG;rU;mG;rG;mC |
| EGFP_1_S2043 | 19 | rG;mC;rC;mA;rC;mA;rA;mC;rG;mU;rC;mU;rA;mU;rA;mU;rC;mA;rU | dA;rU;mG;rA;mU;rA;mU;rA;mG;rA;mC;rG;mU;rU;mG;rU;mG;rG;mC |
| EGFP_1_S2044 | 19 | rG;mC;rC;mA;rC;mA;rA;mC;rG;mU;rC;mU;rA;mU;rA;mU;rC;mA;rU | rA;rU;mG;rA;mU;rA;mU;rA;mG;rA;mC;rG;mU;rU;mG;rU;mG;rG;mC |
| EGFP_1_S1992 | 19 | rG;mC;rC;mA;rC;mA;rA;mC;rG;mU;rC;mU;rA;mU;rA;mU;rC;dA;rU | mA;rU;mG;rA;mU;rA;mU;rA;mG;rA;mC;rG;mU;rU;mG;rU;mG;rG;mC |
| EGFP_1_S2007 | 19 | rG;mC;rC;mA;rC;mA;rA;mC;rG;mU;rC;rU;rA;rU;rA;rU;rC;rA;rU | mA;rU;mG;rA;mU;rA;mU;rA;mG;rA;mC;rG;mU;rU;mG;rU;mG;rG;mC |
| EGFP_1_S1957 | 19 | rG;mC;rC;mA;rC;mA;rA;mC;rG;mU;rC;mU;rA;mU;rA;mU;rC;rA;rU | mA;rU;mG;rA;mU;rA;mU;rA;mG;rA;mC;rG;mU;rU;mG;rU;mG;rG;mC |
| RAC1_28_S1908 | 19 | mC;rG;mU;rG;mC;rA;rA;rA;rG;mU;rG;rG;mU;rA;rU;mC;rC;mU;rA | mU;rA;rG;rG;rA;mU;rA;rC;mC;rA;mC;rU;mU;rU;mG;rC;mA;rC;mG |
| RAC1_28_S2025 | 19 | mC;rG;mU;rG;mC;rA;rA;rA;rG;mU;rG;rG;mU;rA;rU;mC;rC;mU;rA | mU;rA;rG;rG;dA;mU;rA;rC;mC;rA;mC;rU;mU;rU;mG;rC;mA;rC;mG |
| RAC1_28_S2003 | 19 | mC;rG;mU;rG;mC;rA;rA;rA;rG;mU;rG;rG;mU;rA;rU;mC;rC;mU;rA | mU;rA;rG;rG;rA;rU;rA;rC;mC;rA;mC;rU;mU;rU;mG;rC;mA;rC;mG |
| RAC1_28_S2030 | 19 | mC;rG;mU;rG;mC;rA;rA;rA;rG;mU;rG;rG;rU;rA;rU;mC;rC;mU;rA | mU;rA;rG;rG;rA;mU;rA;rC;mC;rA;mC;rU;mU;rU;mG;rC;mA;rC;mG |
| RAC1_28_S1998 | 19 | mC;rG;mU;rG;mC;rA;rA;rA;rG;mU;rG;rG;mU;rA;rU;mC;mC;mU;rA | mU;rA;rG;rG;rA;rU;rA;rC;mC;rA;mC;rU;mU;rU;mG;rC;mA;rC;mG |
| RAC1_28_S1999 | 19 | mC;rG;mU;rG;mC;rA;rA;rA;rG;mU;rG;rG;mU;rA;rU;mC;mC;mU;rA | mU;rA;rG;rG;rA;mU;rA;rC;mC;rA;mC;rU;mU;rU;mG;rC;mA;rC;mG |
| PLK1_28_S2054 | 19 | zc6Np;rA;rG;rA;rA;rG;rA;mU;rG;rC;rU;rU;mC;rA;rG;rA;mC;rA;rG;rU | rA;rC;mU;rG;rU;rC;mU;rG;rA;rA;rG;rC;rA;rU;mC;rU;mU;rC;mU |
| KRAS_2_S2219 | 19 | rG;mU;rA;rA;rG;rG;mC;rA;rG;rA;rC;rC;mC;rA;rG;rU;rA;mU;rA | mU;rA;mU;rA;rC;mU;rG;rG;rG;rU;rC;mU;rG;rC;mC;rU;mU;rA;mC |
| KRAS_2_S2087 | 19 | rG;mU;rA;rA;rG;rG;mC;rA;rG;rA;rC;rC;mC;rA;rG;mU;rA;mU;rA | mU;rA;mU;rA;rC;mU;rG;rG;rG;rU;rC;rG;rU;rC;mU;rG;rC;mC;rU;mU;rA;mC |

TABLE C

Synthesized sense strands and antisense strands for generating dsRNA molecules with at least one RNA pyrazolotriazine (ptr) nucleotide analog

| Name | Length | Sense strand 5->3 | PT RNA Position (5'>3') | Antisense strand 5->3 | PT RNA Position (5'>3') |
|---|---|---|---|---|---|
| EGFP_1_S2141 | 19 | rG;mC;rC;mA;rC;mA;rA;mC;rG;mU;rC;mU;rA;mU;rA;mU;rC;ptrA;rU | 18 | mA;rU;mG;rA;mU;rA;mU;rA;mG;rA;mC;rG;mU;rU;mG;rU;mG;rG;mC | — |
| EGFP_1_S2178 | 19 | rG;mC;rC;mA;rC;mA;rA;mC;rG;mU;rC;mU;rA;mU;rA;mU;rC;mA;rU | — | ptrA;rU;mG;rA;mU;rA;mU;rA;mG;rA;mC;rG;mU;rU;mG;rU;mG;rG;mC | 1 |
| EGFP_1_S2223 | 19 | rG;mC;rC;mA;rC;mA;rA;mC;rG;mU;rC;mU;rA;mU;rA;mU;rC;mA;rU | — | mA;rU;mG;ptrA;rU;rA;mU;rA;mG;rA;mC;rG;mU;rU;mG;rU;mG;rG;mC | 4 |
| EGFP_1_S2224 | 19 | rG;mC;rC;mA;rC;mA;rA;mC;rG;mU;rC;mU;rA;mU;rA;mU;rC;mA;rU | — | mA;rU;mG;rA;mU;ptrA;mU;rA;mG;rA;mC;rG;mU;rU;mG;rU;mG;rG;mC | 5 |
| KRAS_1_S2225 | 19 | rG;mU;rA;rA;rG;rG;mC;rA;rG;rA;rC;rC;mC;rA;rG;rU;ptrA;mU;rA | 17 | mU;rA;mU;rA;rC;mU;rG;rG;rG;rU;rC;rU;rG;rC;mC;rU;mU;rA;mC | — |
| KRAS_2_S2176 | 19 | rG;mU;rA;rA;rG;rG;mC;rA;rG;rA;rC;rC;mC;rA;rG;mU;rA;mU;rA | — | mU;rA;rU;ptrA;rC;mU;rG;rG;rU;rC;rU;rG;rC;mC;rU;mU;rA;mC | 4 |
| KRAS_2_S2179 | 19 | rG;mU;rA;rA;rG;rG;mC;rA;rG;rA;rC;rC;mC;rA;rG;mU;rA;mU;rA | — | mU;ptrA;rU;rA;rC;mU;rG;rG;rU;rC;rU;rG;rC;mC;rU;mU;rA;mC | 2 |
| PLK1_28_S2177 | 19 | zc6Np;rA;rG;rA;rA;rG;rA;mU;rG;rC;rU;rU;mC;rA;rG;rA;mC;rA;rG;rU | — | ptrA;rC;mU;rG;rU;mC;mU;rG;rA;rA;rG;rC;rA;rU;mC;rU;mU;rC;mU | 1 |
| RAC1_28_S2175 | 19 | mC;rG;mU;rG;mC;rA;rA;rA;rG;mU;rG;rG;mU;rA;rU;mC;rC;mU;rA | — | mU;rA;rG;rG;ptrA;mU;rA;rC;mC;rA;mC;rU;mU;rU;mG;rC;mA;rC;mG | 5 |
| RAC1_28_S2220 | 19 | mC;rG;mU;rG;mC;rA;rA;rA;rG;mU;rG;rG;mU;rA;mU;mC;rC;mU;rA | — | mU;rA;rG;rG;ptrA;mU;rA;rC;mC;rA;mC;rU;mU;rU;mG;rC;mA;rC;mG | 5 |
| RAC1_28_S2221 | 19 | mC;rG;mU;rG;mC;rA;rA;rA;rG;mU;rG;rG;mU;rA;rU;mC;rC;mU;rA | — | mU;rA;rG;rG;rA;mU;rA;rC;mC;rA;mC;rU;mU;rU;mG;rC;mA;rC;mG;zptrA$ | One PT 3' overhang |
| RAC1_28_S2222 | 19 | mC;rG;mU;rG;mC;rA;rA;rA;rG;mU;rG;rG;mU;rA;rU;mC;rC;mU;rA | — | mU;rA;rG;rG;rA;mU;rA;rC;mC;rA;mC;rU;mU;rU;mG;rC;mA;rC;mG;zptrA;zptrA$ | Two PT 3' overhangs |

TABLE D

Synthesized sense strands and antisense strands for generating dsRNA molecules with at least one DNA pyrazolotriazine (ptd) nucleotide analog

| Name | Length | Sense strand 5->3 | PT DNA Position (5'>3') | Antisense strand 5->3 | PT DNA Position (5'>3') |
|---|---|---|---|---|---|
| EGFP_1_S1910 | 19 | rG;mC;rC;mA;rC;mA;rA;mC;rG;mU;rC;mU;rA;mU;rA;mU;rC;mA;rU | — | p;ptdA;rU;mG;rA;mU;rA;mU;rA;mG;rA;mC;rG;mU;rU;mG;rU;mG;rG;mC | 1 |
| EGFP_1_S1911 | 19 | rG;mC;rC;mA;rC;mA;rA;mC;rG;mU;rC;mU;rA;mU;rA;mU;rC;mA;rU | — | ptdA;rU;mG;rA;mU;rA;mU;rA;mG;rA;mC;rG;mU;rU;mG;rU;mG;rG;mC | 1 |
| EGFP_1_S1912 | 19 | rG;mC;rC;mA;rC;mA;rA;mC;rG;mU;rC;mU;rA;mU;rA;mU;rC;ptdA;rU$ | 18 | mA;rU;mG;rA;mU;rA;mU;rA;mG;rA;mC;rG;mU;rU;mG;rU;mG;rG;mC | — |

TABLE D-continued

Synthesized sense strands and antisense strands for generating dsRNA
molecules with at least one DNA pyrazolotriazine (ptd) nucleotide analog

| Name | Length | Sense strand 5->3 | PT DNA Position (5'>3') | Antisense strand 5->3 | PT DNA Position (5'>3') |
|---|---|---|---|---|---|
| EGFP_1_S1913 | 19 | rG;mC;rC;mA;rC;mA;rA;mC;rG;mU;rC;mU;rA;mU;rA;mU;rC;ptdA;rU | 18 | mA;rU;mG;rA;mU;rA;mU;rA;mG;rA;mC;rG;mU;rG;mU;mG;rG;mC | — |
| EGFP_1_S2004 | 19 | rG;mC;rC;mA;rC;mA;rA;mC;rG;mU;rC;rU;ptdA;rU;ptdA;rU;rC;ptdA;rU | 13, 15, 18 | ptdA;rU;mG;rA;mU;rA;mU;rA;mG;rA;mC;rG;mU;rG;mU;mG;rG;mC | 1 |
| EGFP_1_S2005 | 19 | rG;mC;rC;mA;rC;mA;rA;mC;rG;mU;rC;rU;rA;rU;rA;rU;rC;rA;rU | — | ptdA;rU;mG;rA;mU;rA;mU;rA;mG;rA;mC;rG;mU;rG;mU;mG;rG;mC | 1 |
| EGFP_1_S2006 | 19 | rG;mC;rC;mA;rC;mA;rA;mC;rG;mU;rC;rU;ptdA;rU;ptdA;rU;rC;ptdA;rU | 13, 15, 18 | mA;rU;mG;rA;mU;rA;mU;rA;mG;rA;mC;rG;mU;rG;mU;mG;rG;mC | — |
| EGFP_2_S1910 | 19 | rG;mC;rA;mU;rC;mG;rA;mG;rC;mU;rG;mA;rA;mG;rG;mG;rC;mA;rU | — | 5'p;ptdA;rU;mG;rC;mC;rC;mU;rU;mC;rA;mG;rC;mU;rC;mG;rA;mU;rG;mC | 1 |
| EGFP_2_S1911 | 19 | rG;mC;rA;mU;rC;mG;rA;mG;rC;mU;rG;mA;rA;mG;rG;mG;rC;mA;rU | — | ptdA;rU;mG;rC;mC;rC;mU;rU;mC;rA;mG;rC;mU;rC;mG;rA;mU;rG;mC | 1 |
| EGFP_2_S1912 | 19 | rG;mC;rA;mU;rC;mG;rA;mG;rC;mU;rG;mA;rA;mG;rG;mG;rC;ptdA;rU$ | 18 | mA;rU;mG;rC;mC;rC;mU;rC;rA;mG;rC;mU;rC;mG;rA;mU;rG;mC | — |
| EGFP_2_S1913 | 19 | rG;mC;rA;mU;rC;mG;rA;mG;rC;mU;rG;mA;rA;mG;rG;mG;rC;ptdA;rU | 18 | mA;rU;mG;rC;mC;rC;mU;rC;rA;mG;rC;mU;rC;mG;rA;mU;rG;mC | — |
| KRAS_2_S2101 | 19 | rG;mU;rA;rA;rG;rG;mC;rA;rG;rA;rC;rC;mC;rA;rG;mU;rA;mU;rA | — | mU;rA;rU;ptdA;rC;mU;rG;rG;rU;rC;rU;rG;rC;mC;rU;mU;rA;mC | 4 |
| RAC1_28_S1917 | 19 | mC;rG;mU;rG;mC;rA;rA;rG;mU;rG;rG;rG;mU;rA;rU;mC;rC;mU;rA | | mU;rA;rG;ptdA;mU;rA;rC;mC;rA;mC;rU;mU;rG;mC;rA;rC;mG | 5 |
| RAC1_28_S1920 | 19 | mC;rG;mU;rG;mC;rA;rA;rG;mU;rG;rG;rG;mU;rA;rU;mC;rC;mU;rG | | mC;rA;rG;rA;mU;ptdA;rC;mC;rA;mC;rU;mU;rG;mC;rA;rC;mG | 7 |
| RAC1_28_S1996 | 19 | mC;rG;mU;rG;mC;rA;rA;rG;mU;rG;rG;rG;mU;rA;rU;mC;mC;mU;rA | | mU;rA;rG;ptdA;rU;rA;rC;mC;rA;mC;rU;mU;rG;mC;rA;rC;mG | 5 |
| RAC1_28_S1997 | 19 | mC;rG;mU;rG;mC;rA;rA;rG;mU;rG;rG;rG;mU;rA;rU;mC;mC;mU;rA | | mU;rA;rG;rG;ptdA;rU;ptdA;rC;mC;rA;mC;rU;mU;rU;mG;rC;mA;rC;mG | 5, 7 |
| RAC1_28_S2000 | 19 | mC;rG;mU;rG;mC;rA;rA;rG;mU;rG;rG;rG;mU;rA;rU;mC;mC;mU;rA | | mU;rA;rG;ptdA;mU;rA;rC;mC;rA;mC;rU;mU;rG;mC;rA;rC;mG | 5 |
| RAC1_28_S2001 | 19 | mC;rG;mU;rG;mC;rA;rA;rG;mU;rG;rG;rG;mU;rA;rU;mC;mC;mU;rA | | mU;rA;rG;ptdA;rU;rA;rC;mC;rA;mC;rU;mU;rG;mC;rA;rC;mG | 5 |
| RAC1_28_S2002 | 19 | mC;rG;mU;rG;mC;rA;rA;rG;mU;rG;rG;rG;mU;rA;rU;mC;mC;mU;rA | | mU;rA;rG;rG;ptdA;rU;ptdA;rC;mC;rA;mC;rU;mU;rU;mG;rC;mA;rC;mG | 5, 7 |
| RAC1_28_S2026 | 19 | mC;rG;mU;rG;mC;rA;rA;rG;mU;rG;rG;rG;mU;rA;mU;mC;rC;mU;rA | | mU;rA;rG;ptdA;mU;rA;rC;mC;rA;mC;rU;mU;rG;mC;rA;rC;mG | 5 |
| RAC1_28_S2028 | 19 | mC;rG;mU;rG;mC;rA;rA;rG;mU;rG;rG;rG;mU;rA;rU;rC;rC;mU;rA | - | mU;rA;rG;ptdA;mU;rA;rC;mC;rA;mC;rU;mU;rG;mC;rA;rC;mG | 5 |

TABLE D-continued

Synthesized sense strands and antisense strands for generating dsRNA
molecules with at least one DNA pyrazolotriazine (ptd) nucleotide analog

| Name | Length | Sense strand 5->3 | PT DNA Position (5'>3') | Antisense strand 5->3 | PT DNA Position (5'>3') |
|---|---|---|---|---|---|
| RAC1_28_S2228 | 19 | mC;rG;mU;rG;mC;rA;rA;rA; rG;mU;rG;rG;mU;rA;rU;m; C;rC;mU;rA | - | mU;rA;rG;rG;rA;mU;rA;rC;mC;rA; mC;rU;mU;rU;mG;rC;mA;rC;mG;z ptdA$ | One PT 3' overhang |
| RAC1_28_S2229 | 19 | mC;rG;mU;rG;mC;rA;rA;rA rG;mU;rG;rG;mU;rA;rU;m C;rC;mU;rA | - | mU;rA;rG;rG;rA;mU;rA;rC;mC;rA; mC;rU;mU;rU;mG;rC;mA;rC;mG;z ptdA;zptdA$ | Two PT 3' overhangs |

TABLE E

Legend of the pyrazolotriazine nucleotide analogs, unmodified and modified
nucleotides/unconventional moieties as used in the Tables hereinabove.

| | Description |
|---|---|
| rA | riboadenosine-3'-phosphate; 3'-adenylic acid |
| rC | ribocytidine-3'-phosphate; 3'-cytidylic acid |
| rG | riboguanosine-3'-phosphate; 3'-guanylic acid |
| rU | ribouridine-3'-phosphate; 3'-uridylic acid |
| mA | 2'-O-methyladenosine-3'-phosphate; 2'-O-methyl-3'-adenylic acid |
| mC | 2'-O-methylcytidine-3'-phosphate; 2'-O-methyl-3'-cytidylic acid |
| mG | 2'-O-methylguanosine-3'-phosphate; 2'-O-methyl-3'-guanylic acid |
| mU | 2'-O-methyluridine-3'-phosphate; 2'-O-methyl-3'-uridylic acid |
| dA | deoxyriboadenosine-3'-phosphate; 2'-deoxyribo-3'-adenylic acid (deoxyadenosine) |
| dC | deoxyribocytidine-3'-phosphate; 2'-deoxyribo-3'-cytidylic acid (deoxycytidine) |
| dG | deoxyriboguanosine-3'-phosphate; 2'-deoxyribo-3'-guanylic acid (deoxyguanosine) |
| dT | thymidine-3'-phosphate; 3'-thymidylic acid |
| rA2p | riboadenosine-2'-phosphate; 2'-adenylic acid (2'5' A) (adenosine) |
| rC2p | ribocytidine-2'-phosphate; 2'-cytidylic acid (2'5' C) (cytidine) |
| rG2p | riboguanosine-2'-phosphate; 2'-guanylic acid (2'5' G) (guanosine) |
| rU2p | ribouridine-2'-phosphate; 2'-uridylic acid (2'5'U) (uridine) |
| LdA | L-deoxyriboadenosine-3'-phosphate (mirror image dA) |
| LdC | L-deoxyribocytidine-3'-phosphate (mirror image dC) |
| LdG | L-deoxyriboguanosine-3'-phosphate (mirror image dG) |
| LdT | L-deoxyribothymidine-3'-phosphate (mirror image dT) |
| dB | abasic deoxyribose-3'-phosphate; 1,2-dideoxy-D-ribofuranose-3-phosphate; 1,4-anhydro-2-deoxy-D-ribitol-3-phosphate |
| zidB | Inverted abasic deoxyribose-5'-phosphate; At 5' = 5'-5' idAb; At 3' = 3'-3' idAb |
| z | Prefix to indicate moiety covalently attached to 3' terminus or 5' terminus |
| zdT; zdT | 3' dTdT overhang |
| tnaA | a-L-threofuranosyl adenine |
| tnaC | a-L-threofuranosyl cytosine |
| tnaG | a-L-threofuranosyl guanine |
| tnaU | a-L-threofuranosyl uracil |
| psiU | pseudouridine |
| p | 5' phosphate |
| s | 5' phosphorothioate |
| c3 | C3 non-nucleotide overhang |
| $ | lacking a 3' phosphate (Pi) (used together with above nucleotides at the 3' end of the sequence) |
| ptrA | Pyrazolotriazine adenosine |
| ptrG | Pyrazolotriazine guanosine |
| ptdA | Pyrazolotriazine deoxyadenosine |
| ptdG | Pyrazolotriazine deoxyguanosine |
| zc3p; zc3p; zc3p | (CH2)3-Pi-(CH2)3-Pi-(CH2)3-Pi |
| zc3p; zc3ps | (CH2)3-Pi; (CH2)-3'phosphorothioate |

Example 3. FACS Analysis of GFP (Green Fluorescent Protein) Expression Following dsRNA Transfection in GFP Transfected RAT1 Cells In each well of a 6-well plate, $1.5 \times 10^5$ Rat1 cells, stably expressing the GFP gene, were grown in 1.5 mL growth medium and incubated at 37±1° C., 5% $CO_2$ for about 24 hours to about 30-50% confluence. Cells were then transfected with dsRNA targeting GFP to final transfection concentrations ranging between 0.1-40 nM using Lipofectamine® 2000. About 48-72 hours later, the cells were harvested and GFP intensity was measured by FACScalibur™ and analyzed by CellQuest™ software.

RNA from harvested cells was isolated using EZ-RNA kit [Biological Industries (#20-410-100)] and reverse transcription performed as follows: cDNA was synthesized and GFP mRNA levels were determined by Real Time qPCR and normalized to those of the Cyclophilin A (CYNA, PPIA) mRNA for each sample. dsRNA activity was determined based on the ratio of the GFP mRNA quantity in dsRNA-treated samples versus non-transfected control samples.

Example 4. Activity of dsRNA in the psiCHECK™-2 System

Several psiCHECK™-2-based (Promega) constructs were prepared for the evaluation of the potential activity and off-target activity of control and test dsRNA molecules. The psiCHECK™ constructs contained single copies of matched complementary guide (GS-CM) or three copies of sequences complementary to the guide (antisense; AS) strand seed regions (GS-SM) cloned at optimal distances between them (for testing potential seed-mediated off-target effects in most stringent conditions) or "full sensor" psiCHECK™ constructs contain four tandem copies of the "full-sensor" sequence of the guide strand, which includes the seed region, position 2-8 of the AS strand, followed by a spacer of 4 non-target nucleotides and then by the central region of the AS strand, positions 13-17. DNA sequences of the psiCHECK™ constructs are provided in Table F, herein below.

a 100 μL final volume. Cells were incubated for 48 hours at 37±1° C. and Renilla and FireFly Luciferase activities were measured as described below.

Example 5. Determination of Dual Luciferase Activity in Transfected Cells

The psiCHECK™-2 vector enables monitoring of changes in expression of a target sequence fused to the Renilla luciferase reporter gene. The dsRNA target sequence was cloned into the 3'-untranslated region (3'-UTR) of Renilla luciferase. Measuring the decrease in Renilla luciferase activity thus provides a convenient way of monitoring the effect of the dsRNA. In addition, the psiCHECK™-2 vector contains a second reporter gene, Firefly luciferase, transcribed under a different promoter, which allows for normalization of Renilla luciferase expression.

48 hours following dsRNA transfection Renilla and FireFly Luciferase activities were measured in each of the dsRNA transfected samples, using the Dual-Luciferase® Assay kit (Promega, Cat #E1960) according to manufacturer's procedure. The Renilla luciferase activity value was

TABLE F

| siRNA | psiCHECK clone name | Sense strand sequence (5'>3') (target sequence-transcribed strand of the clone) (guide target sequence - bold, underlined) | Antisense strand sequence (5'>3') (non-transcribed strand of the clone) (similar to guide sequence - bold, underlined) |
|---|---|---|---|
| RAC1_28 | RAC1_28_AS-CMx1 | TCGAGCGTGCAAAGTGGTATCC TGGC (SEQ ID NO: 16) | GGCCGCCAGGATACCACTTTGC ACGC (SEQ ID NO: 17) |
| RAC1_28 | RAC1_28_AS-SMx3 | TCGAGATGTAACCTGTGTATCCT TGTCCATGTAACCTGTGTATCCT TGTCCATGTAACCTGTGTATCCT TGC (SEQ ID NO: 18) | GGCCGCAAGGATACACAGGTTA CATGGACAAGGATACACAGGTT ACATGGACAAGGATACACAGGT TACATC (SEQ ID NO: 19) |
| EGFP_1 | EGFP_1_AS-CMx1 | TCGAGGCCACAACGTCTATATC ATGC (SEQ ID NO: 20) | GGCCGCATGATATAGACGTTGT GGCC (SEQ ID NO: 21) |
| EGFP_1 | EGFP_1_AS-SMx3 | TCGAGCGGTGATGCAGTATATC AACCTTCGGTGATGCAGTATATC AACCTTCGGTGATGCAGTATATC AAGC (SEQ ID NO: 22) | GGCCGCTTGATATACTGCATCAC CGAAGGTTGATATACTGCATCA CCGAAGGTTGATATACTGCATC ACCGC (SEQ ID NO: 23) |
| PLK1_28 | PLK_25_AS-CMx1 | TCGAGAGAAGATGCTTCAGACA GAGC (SEQ ID NO: 24) | GGCCGCTCTGTCTGAAGCATCT TCTC (SEQ ID NO: 25) |
| PLK1_28 | PLK1_28_AS-SMx3 | TCGAGGTGCGACCTCGCAGACA GAGTCCGTGCGACCTCGCAGAC AGAGTCCGTGCGACCTCGCAGA CAGAGC (SEQ ID NO: 26) | GGCCGCTCTGTCTGCGAGGTCG CACGGACTCTGTCTGCGAGGTC GCACGGACTCTGTCTGCGAGGT CGCACC (SEQ ID NO: 27) |
| KRAS_2 | KRAS_2_AS-CM | TCGAGTTAAGGCAGACCCAGTA TGGC (SEQ ID NO: 28) | GGCCGCCATACTGGGTCTGCCT TAAC (SEQ ID NO: 29) |
| KRAS_2 | KRAS_2_AS-SMx3 | TCGAGAGCATTACTTCCCAGTAT CTTCCAGCATTACTTCCCAGTAT CTTCCAGCATTACTTCCCAGTAT CGC (SEQ ID NO: 30) | GGCCGCGATACTGGGAAGTAAT GCTGGAAGATACTGGGAAGTAA TGCTGGAAGATACTGGGAAGTA ATGCTC (SEQ ID NO: 31) |

1.3-1.5×10$^6$ human HeLa cells were inoculated in a 10 cm petri dish. Cells were incubated in 37±1° C., 5% $CO_2$ incubator for 24 hours. Growth medium was replaced one day post inoculation by 8 mL fresh growth medium and each plate was transfected with one of the plasmids mentioned above, using Lipofectamine™2000 reagent according to manufacturer's protocol and incubated for 5 hours at 37±1° C. and 5% $CO_2$.

Following incubation, cells were re-plated in a 96-well plate at a final concentration of 5×10$^3$ cells per well in 80 μL growth medium. Sixteen (16) hours later, cells were transfected with dsRNA molecules using Lipofectamine™2000 at final concentrations ranging from 0.01 nM to 100 nM in divided by firefly luciferase activity value for each sample (normalization). Renilla luciferase activity is finally expressed as the percentage of the normalized activity value in tested sample relative to the normalized value obtained in cells transfected with the corresponding psiCHECK™-2 plasmid in the absence of dsRNA.

FIGS. 2A, 2B, 5B and 12 show on-target knock down activity of several dsRNA described herein.

FIGS. 6, 7, 9, and 10 show on-target (AS-CM) and off-target (AS_SMx3) knock-down activity of various dsRNA described herein.

Figure 11:
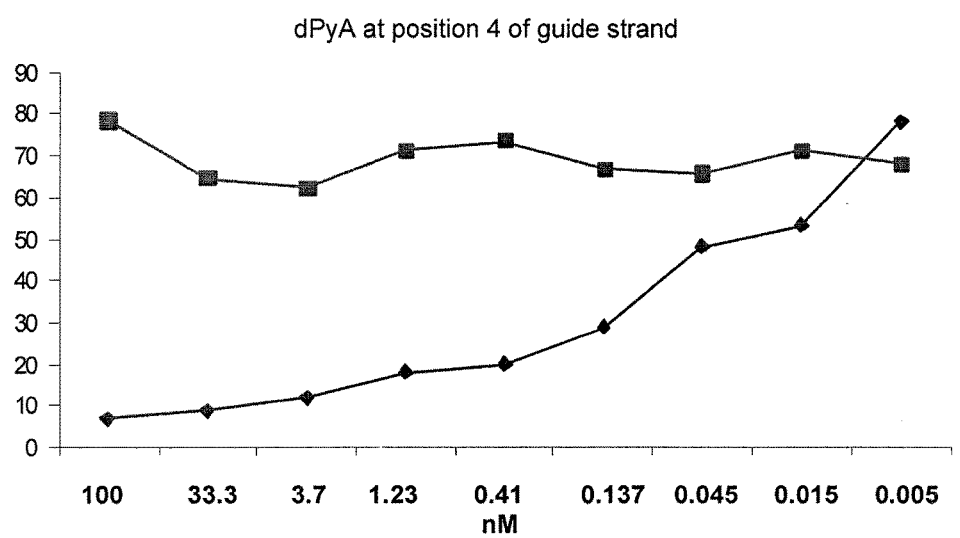
FIG. 11 shows improved target specificity of dsRNA with pyrazolotriazine in seed region (position 4) of antisense strand compared to dsRNA with riboadenosine in same position. Lines linked by squares reflects on-target activity. Lines linked by diamonds reflects off-target activity. The dsRNA molecules tested included KRAS_2_2101 and KRAS_2_2087. KRAS_2_2101 and KRAS_2_2087 share the same sense strand which included unmodified ribonucleotides in positions 1, 3, 4, 5, 6, 8, 9, 10, 11, 12, 14, 15, 17 and 19, 2'-OMethyl sugar modified ribonucleotides in positions 2, 7, 13, 16 and 18, and phosphate moiety at the 3' terminus. KRAS_2_2101 and KRAS_2_2087 antisense strands included unmodified ribonucleotides in positions 2, 5, 7, 8, 9, 10, 11, 12, 13, 14, 16 and 18, 2'-OMethyl sugar modified ribonucleotides in positions 1, 6, 15, 17 and 19, and phosphate moiety at the 3' terminus KRAS_2_2101 antisense strand further included an unmodified ribonucleotide at position 3 and a pyrazolotriazine deoxyadenosine nucleotide analogue at position 4. KRAS_2_2087 antisense strand further included a 2'-OMethyl sugar modified ribonucleotide at position 3 and an unmodified riboadenosine at position 4.
Figure 11:
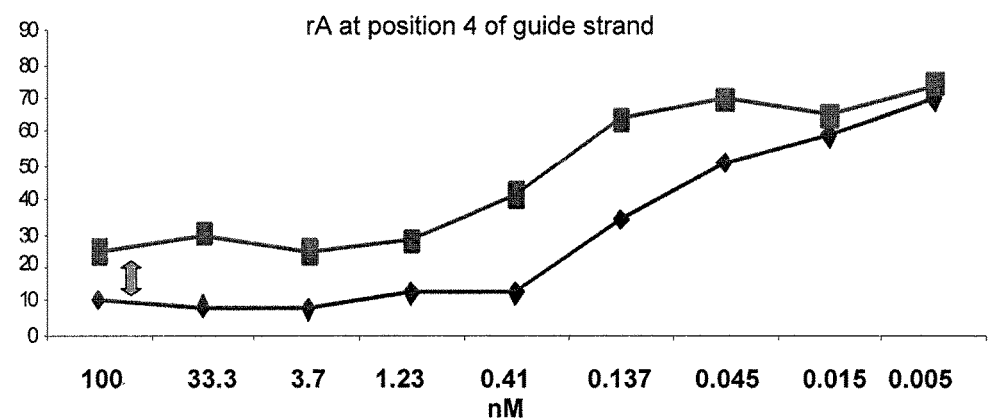
Figure 12:
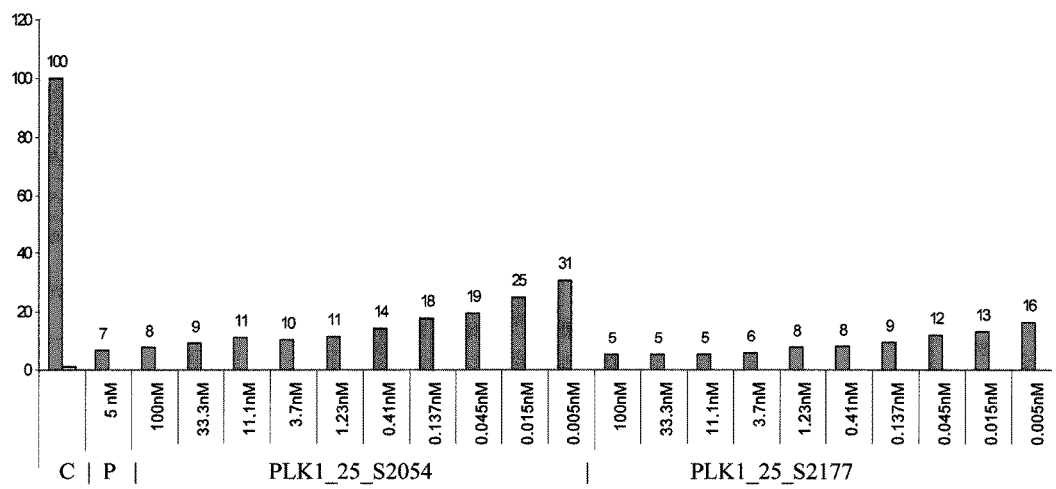
FIG. 12 shows improved knock-down activity of a dsRNA molecule with pyrazolotriazine RNA in position 1 of the antisense strand compared to a dsRNA molecule with riboadenosine in the same position. PLK1_25_S2054 and PLK1_25_S2177 share the same sense stand which included unmodified ribonucleotides in positions 1, 2, 3, 4, 5, 6, 8, 9, 10, 11, 13, 14, 15, 17, 18 and 19, 2'-OMethyl sugar modified ribonucleotides in positions 7, 12 and 16, an amino C6 capping moiety covalently attached to the 5' terminus and phosphate moiety at the 3' terminus. The antisense strands of PLK1_25_S2054 and PLK1_25_S2177 included unmodified ribonucleotides in positions 2, 4, 5, 6, 8, 9, 10, 11, 12, 13, 14, 16, and 18, 2'-OMethyl sugar modified ribonucleotides in positions 3, 7, 15, 17 and 19, and a phosphate moiety at the 3' terminus PLK1_25_S2054 antisense strand further included an unmodified riboadenosine at position 1 and PLK1_25_S2177 antisense strand further included a pyrazolotriazine riboadenosine nucleotide analogue at position 1.

FIG. 11 shown the increased specificity of a dsRNA molecule with a PT nucleotide analog in position 1 of the antisense (guide) strand compared to a similarly modified dsRNA with adenosine in position 1.

IC50 Values are Determined as Follows:

About $1\text{-}2 \times 10^5$ human or rat cells endogenously expressing the target gene, are inoculated in 1.5 mL growth medium in order to reach 30-50% confluence. Cells are transfected with double-stranded RNA molecules with Lipofectamine™2000 reagent to reach final transfection concentrations ranging between 0.0029-100 nM. As negative control cells are treated with Lipofectamine™2000 reagent or with Synthetic randomized-sequence, non-targeting siRNA at final concentrations of 20-100 nM. Cy3-labeled dsRNA transfected cells were used as positive control for transfection efficiency.

Cells are incubated at 37±1° C., 5% $CO_2$ for 48 hours. dsRNA transfected cells are harvested and RNA was isolated using EZ-RNA kit (Biological Industries (#20-410-100) Reverse transcription: Synthesis of cDNA is performed and target gene mRNA levels are determined by Real Time qPCR and normalized to those of the Cyclophilin A (CYNA, PPIA) mRNA for each sample.

The IC50 value of the tested RNAi activity is determined by constructing a dose-response curve using the activity results obtained with the various final dsRNA concentrations. The dose response curve is constructed by plotting the relative amount of residual target mRNA versus the logarithm of transfected dsRNA concentration. The curve is calculated by fitting the best sigmoid curve to the measured data.

The percent of inhibition of gene expression using specific dsRNAs was determined using qPCR analysis of target gene in cells expressing the endogenous gene.

Example 6. Plasma and Exonuclease Stability Assays

Plasma Stability

The dsRNA molecules disclosed herein are tested for duplex stability in human, rat or mouse serum or human tissue extract, as follows:

dsRNA molecules at final concentration of 7 uM are incubated at 37° C. in 100% human serum (Sigma Cat# H4522). (siRNA stock 100 uM diluted in human serum 1:14.29 or human tissue extract from various tissue types.). Five μL (5 μL) are added to 15 μL 1.5×TBE-loading buffer at different time points (for example 0, 30 min, 1 h, 3 h, 6 h, 8 h, 10 h, 16 h and 24 h). Samples are immediately frozen in liquid nitrogen and are kept at −20° C.

Each sample is loaded onto a non-denaturing 20% acrylamide gel, prepared according to methods known in the art. The dsRNA molecules are visualized with ethidium bromide under UV light.

Figure 1B:
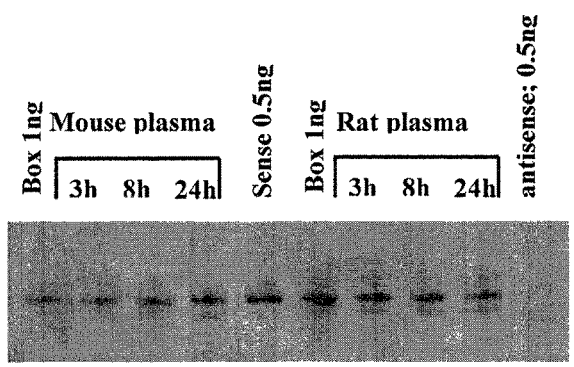
Figure 1B:
Figure 2A:
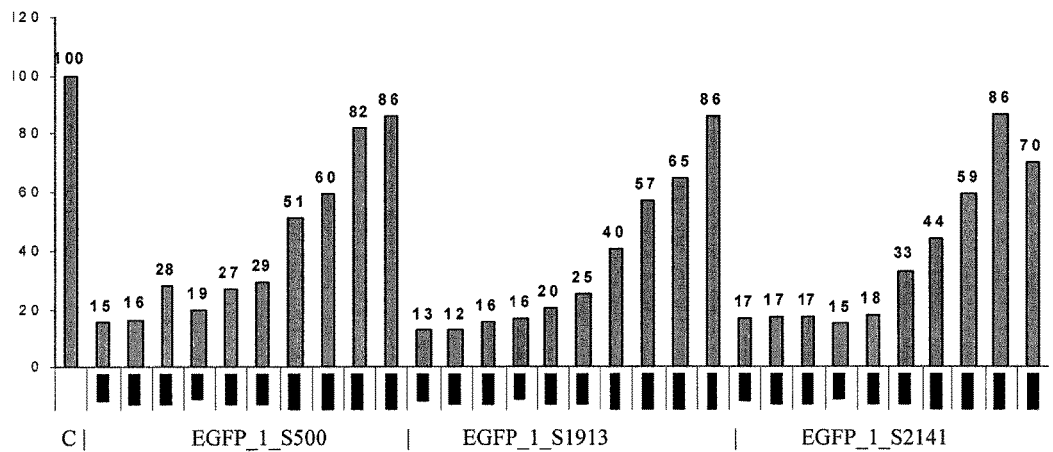
FIG. 2A shows activity (% residual mRNA) for different concentrations of the EGFP_1_S500, EGFP_1_S1913 and EGFP_1_S2141 molecules (the stability of which is shown in FIG. 1A) tested in GFP transfected RAT1 cells (example 3 hereinbelow).
Figure 2B:
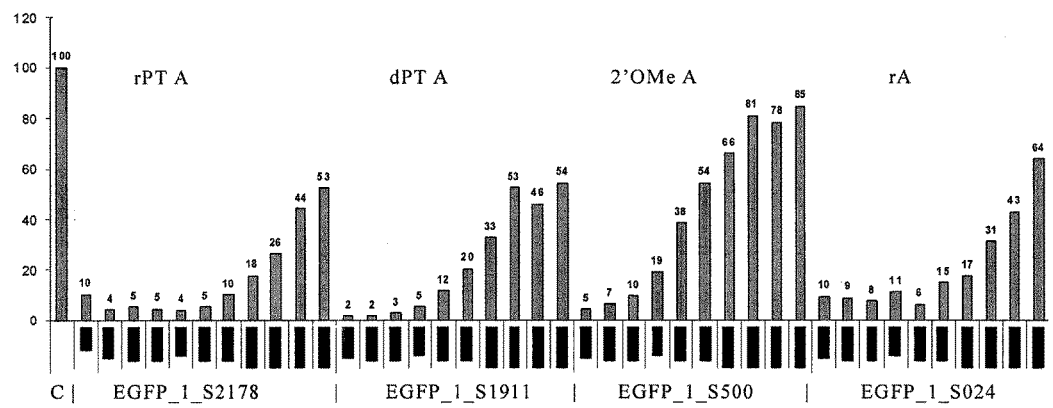
FIG. 2B shows activity (% residual mRNA) for different concentrations of dsRNA molecules EGFP_1 S2178, EGFP_1 S1911, EGFP_1 S500, EGFP_1 S024, i.e. a dsRNA molecule with deoxyriboadenosine PT moiety at position 1 in the antisense strand (EGFP_1_S1911), or a dsRNA molecule with riboadenosine PT moiety at position 1 in the antisense strand (EGFP_1_S2178) compared to dsRNA molecule with unmodified riboadenosine at position 1 in the antisense strand (EGFP_1_S024) and a dsRNA molecule with a 2'-OMethyl sugar modified riboadenosine at position 1 in the antisense strand. In general, the dsRNA molecules which include a PT moiety at position 1 in the antisense strand show enhanced knock-down activity over similarly modified dsRNA molecules with unmodified or 2'-OMethyl sugar-modified ribonucleotide in the same position
Figure 5A:
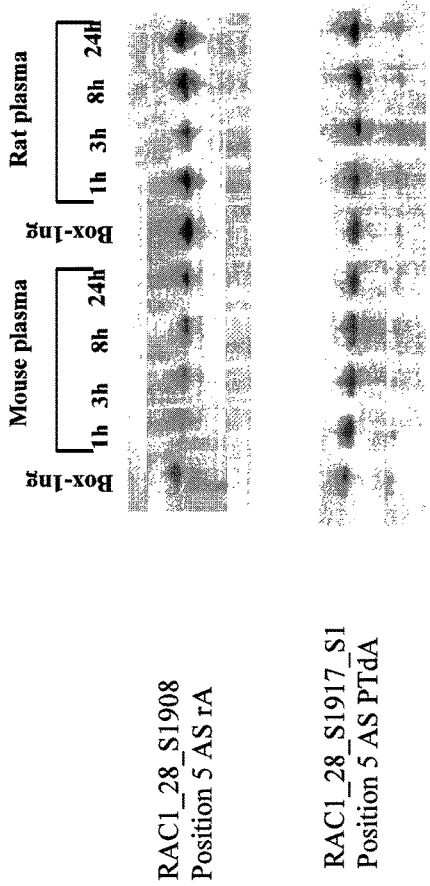
FIG. 5A shows plasma (mouse and rat) stability of pyrazolotriazine-modified RAC1_28 dsRNA molecule with a PT deoxyadenosine nucleotide analogue in position 5 of the sense strand (seed region). RAC1_28_S1917 and RAC1_28_S1908 share the same sense strand. The shared sense strand included unmodified ribonucleotides in positions 2, 4, 6, 7, 8, 9, 11, 12, 14, 15, 17 and 19 (5'>3') and 2'-OMethyl sugar modified ribonucleotides in positions 1, 3, 5, 10, 13, 16 and 18. RAC1_28_S1917 antisense strand included 2'-OMethyl sugar modified ribonucleotides in positions (5'>3') 1, 6, 9, 11, 13, 15, 17 and 19, unmodified ribonucleotides in positions 2, 3, 4, 7, 8, 10, 12, 14, 16 and 18 and a PT deoxyadenosine nucleotide analogue in position 5; RAC1_28_S1908 antisense strand included unmodified ribonucleotides in positions (5'>3') 2, 3, 4, 5, 7, 8, 10, 12, 14, 16 and 18; and 2'-OMethyl sugar modified ribonucleotides in positions 1, 6, 9, 11, 13, 15, 17 and 19 (unmodified ribonucleotide in position 5).
Figure 5B:
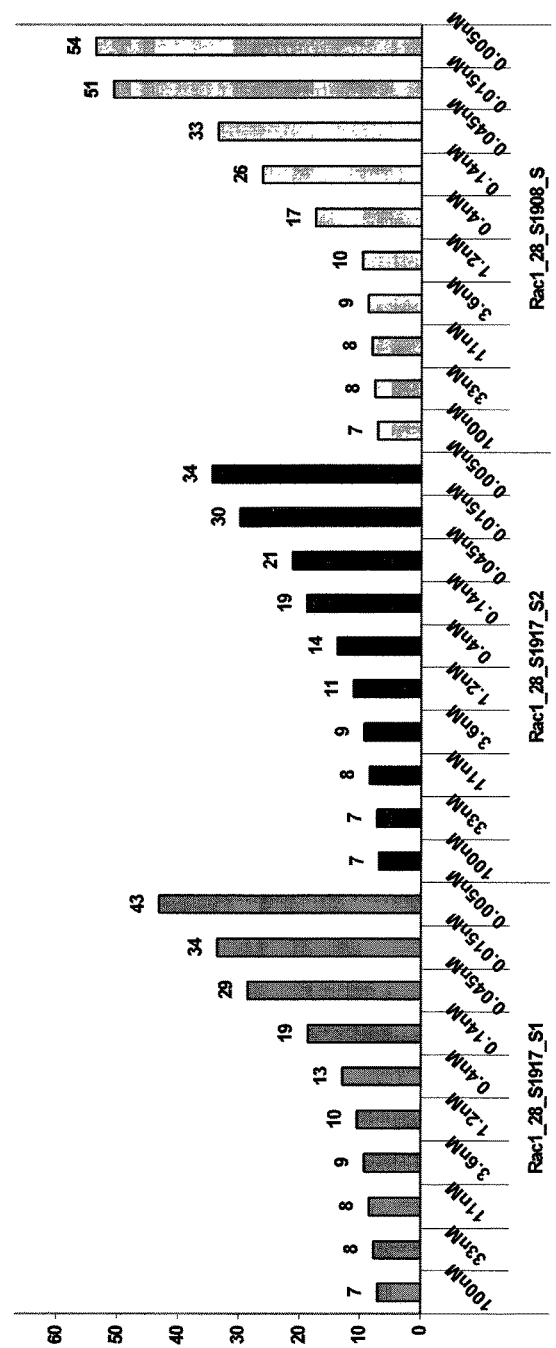
FIG. 5B shows activity (% residual mRNA) of RAC1_28_S1917 and RAC1_28_S1908 at different concentrations (Syn1 and Syn 2 refer to two different syntheses of _S1917). The knock down activity of the dsRNA with the PT deoxyadenosine nucleotide (i.e. RAC1_28_S1917) is significantly better than the dsRNA with an unmodified RNA at the same position (position 5 of the antisense strand), when compared for the low concentrations of the dsRNA compounds (i.e. 0.4 nM, 0.14 nM, 0.045 nM, 0.015 nM and 0.005 nM).
Figure 6:
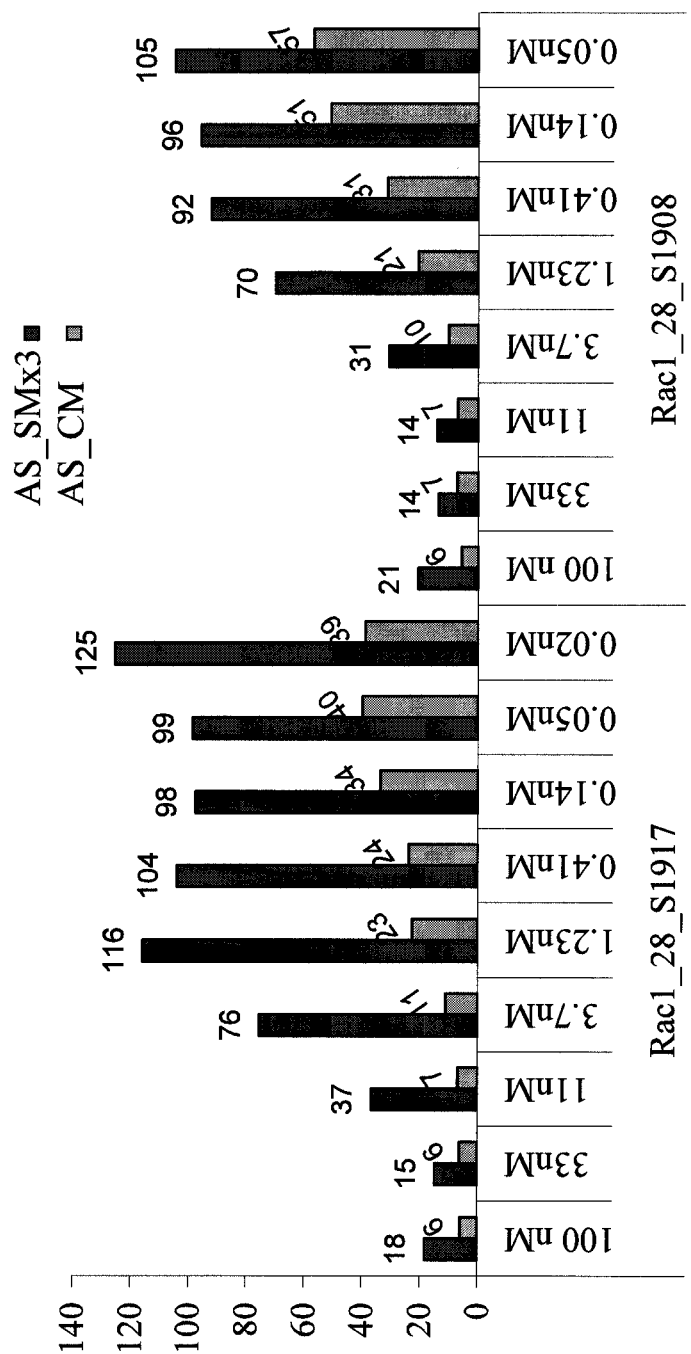
FIG. 6 shows reduced off-target activity to seed match (SMx3) of compounds described above in FIGS. 5A and 5B. The pyrazolotriazine-modified RAC1_28_S1917 shows reduced off-target activity of the antisense strand (AS_SMx3, antisense seed match 3 copies) and better on-target activity (AS_CM, antisense complete match) compared to RAC1_28 S1908.
Figure 7:
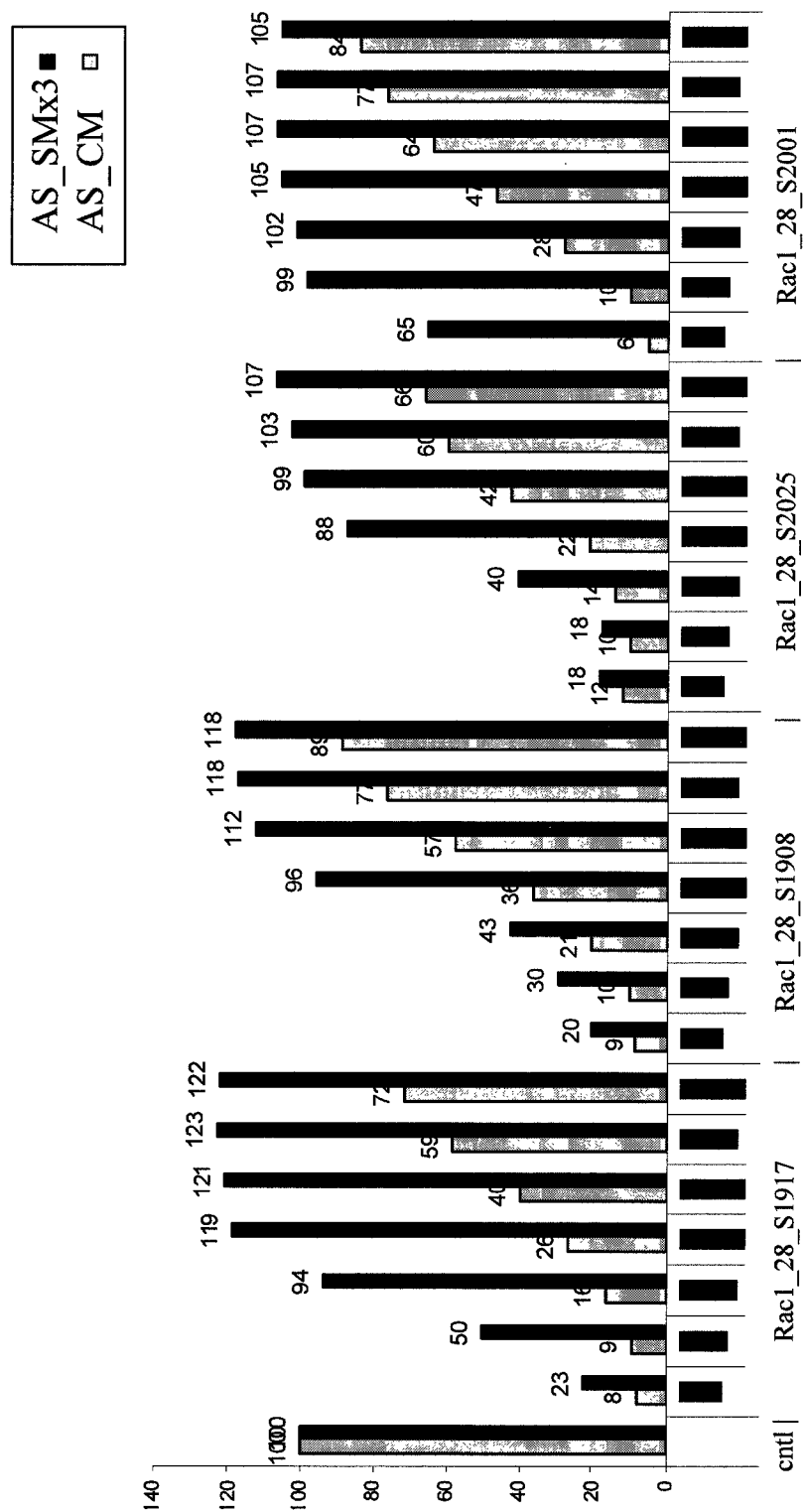
FIG. 7 shows reduced off-target activity to seed match (SMx3) of dsRNA molecules described above in FIGS. 5A and 5B (i.e. RAC1_28_S1917 and RAC1_28_S1908) and of dsRNA molecules having a RNA or standard DNA in position 5 of the antisense strand (i.e. RAC1_28_S2025 and RAC1_28_S2001). RAC1_28_S1917, RAC1_28_S1908, RAC1_28 S2025, and RAC1_28 S2001 share the same sense strand. The shared sense strand included unmodified ribonucleotides in positions 2, 4, 6, 7, 8, 9, 11, 12, 14, 15, 17 and 19 (5'>3'), 2'-OMethyl sugar modified ribonucleotides in positions 1, 3, 5, 10, 13, 16 and 18 and a 3' terminal phosphate. RAC1_28_S1917 and RAC1_28_S1908 antisense strands are described above. RAC1_28_S2025 antisense strand included 2'-OMethyl sugar modified ribonucleotides in positions (5'>3') 1, 6, 9, 11, 13, 15, 17 and 19, unmodified ribonucleotides in positions 2, 3, 4, 7, 8, 10, 12, 14, 16 and 18 and a standard deoxyadenosine nucleotide in position 5; RAC1_28_S2001 antisense strand included 2'-OMethyl sugar modified ribonucleotides in positions (5'>3') 1, 9, 11, 13, 15, 17 and 19, unmodified ribonucleotides in positions 2, 3, 4, 6, 7, 8, 10, 12, 14, 16 and 18 and a PT deoxyadenosine nucleotide analogue in position 5. The pyrazolotriazine-modified RAC1_28_S1917 and RAC1_28_S2001 show reduced off-target activity of the antisense strand (AS_SMx3, antisense seed match 3 copies) and better on-target activity (AS_CM, antisense complete match) compared to RAC1__28_S1908 (adenosine (rA) in position 5) or RAC1_28_S2025 (standard DNA in position 5).

FIGS. 1A, 1B and 5A show stability of dsRNA molecules in rat or mouse plasma over time.

Exonuclease Stability Assay

To study the stabilization effect of 3' non-nucleotide moieties on a nucleic acid molecule the sense strand, the antisense strand and the annealed dsRNA duplex are incubated in cytosolic extracts prepared from different cell types.

Extract: HCT116 cytosolic extract (12 mg/ml).

Extract buffer: 25 mM Hepes pH=7.3 at 37° C.; 8 mM MgCl; 150 mM NaCl with 1 mM DTT was added fresh immediately before use.

Method: 3.5 ml of test dsRNA (100 mM), were mixed with 46.5 ml contain 120 mg of HCT116 cytosolic extract. The 46.5 ml consists of 12 ml of HCT116 extract, and 34.5 ml of the extract buffer supplemented with DTT and protease inhibitors cocktail/100 (Calbiochem, setIII-539134). The final concentration of the dsRNA in the incubation tube is 7 mM. The sample was incubated at 37° C., and at the indicated time point 5 ml were moved to fresh tube, mixed with 15 ml of 1×TBE-50% Glycerol loading buffer, and snap frozen in Liquid N2. The final concentration of the siRNA in the loading buffer is 1.75 mM (21 ng siRNA/ml). For Analyses by native PAGE and EtBr staining 50 ng are loaded per lane. For Northern analyses ing of tested dsRNA was loaded per lane.

Figure 3A:
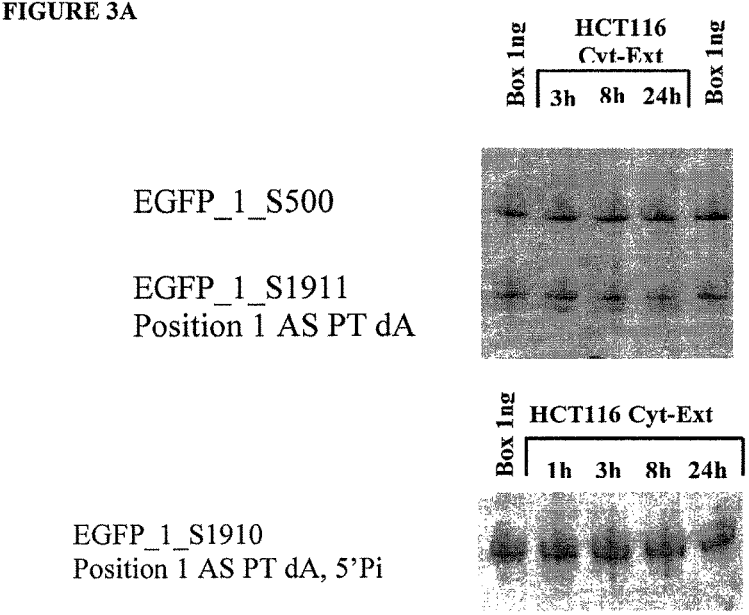
FIG. 3A shows cell extract stability (in hours) of a dsRNA molecule having an antisense strand with PT deoxyadenosine in position 1. EGFP_1_S500, EGFP_1_S1911, and EGFP_1 S1910 shared the same sense strand. The shared sense strand included unmodified ribonucleotides in positions 1, 3, 5, 7, 9, 11, 13, 15, 17 and 19 (5'>3') and 2'-OMethyl sugar modified ribonucleotides in positions 2, 4, 6, 8, 10, 12, 14, 16 and 18. EGFP_1 S500 antisense strand included 2'-OMethyl sugar modified ribonucleotides in positions (5'>3') 1, 3, 5, 7, 9, 11, 13, 15, 17 and 19 and unmodified ribonucleotides in positions 2, 4, 6, 8, 10, 12, 14, 16 and 18; EGFP_1_S1911 antisense strand included unmodified ribonucleotides in positions (5'>3') 2, 4, 6, 8, 10, 12, 14, 16 and 18; and 2'-OMethyl sugar modified ribonucleotides in positions 3, 5, 7, 9, 11, 13, 15, 17 and 19 and a PT deoxyadenosine nucleotide analogue in position 1.
Figure 3B:
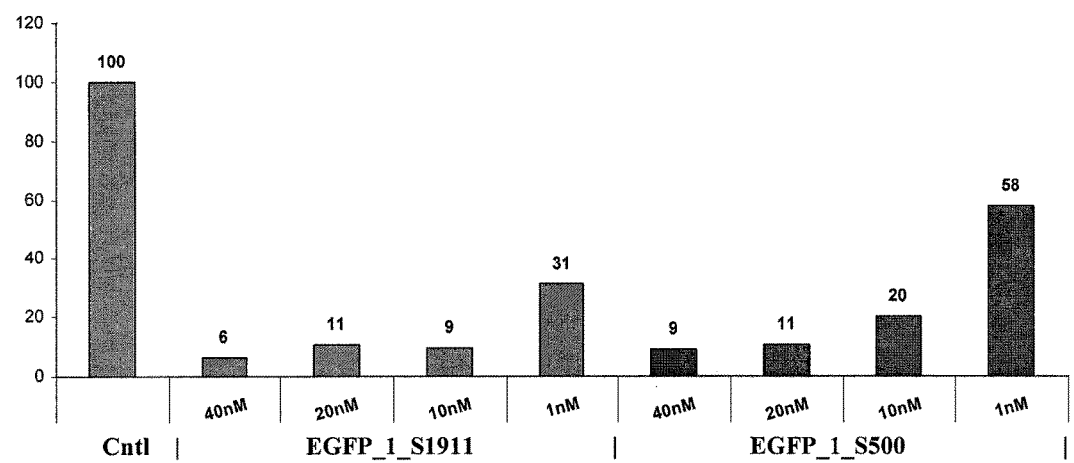
FIG. 3B shows activity (% residual mRNA) for different concentrations of two of the compounds of FIG. 3A (i.e. EGFP_1 S1911 and EGFP_1 S500).
Figure 4A:
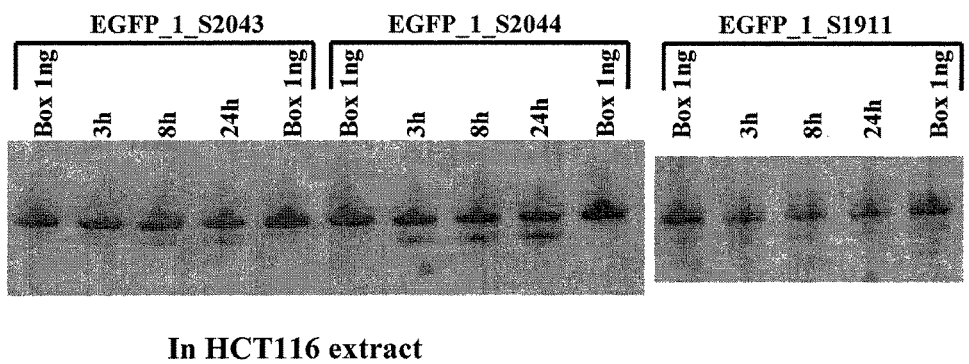
FIGS. 4A and 4B show stability of a dsRNA molecule having an antisense strand with PT deoxyadenosine in position 1 in a cell extract (FIG. 4A: HCT116 extract.
Figure 4B:
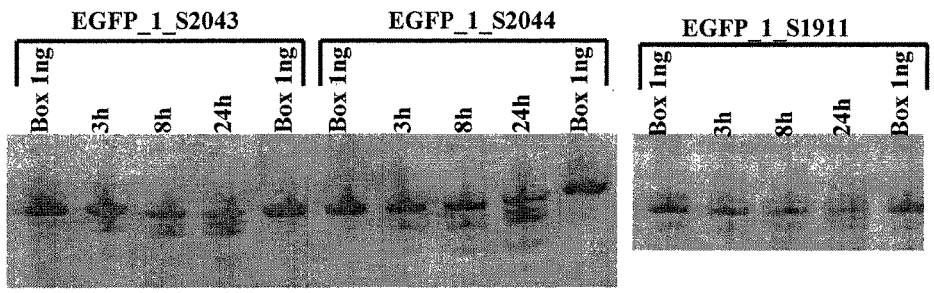

FIGS. 3A, 4A and 4B show stability of dsRNA molecules in cell extracts over time.

Example 7. Innate Immune Response to dsRNA Molecules

Fresh human blood (at RT) was mixed at 1:1 ratio with sterile 0.9% NaCl at RT, and gently loaded (1:2 ratio) on Ficoll (Lymphoprep, Axis-Shield cat#1114547). Samples were centrifuged at RT (22° C., 800 g) in a swinging centrifuge for 30 minutes, washed with RPMI1640 medium and centrifuged (RT, 250 g) for 10 minutes. Cells were counted and seeded at final concentration of $1.5 \times 10^6$ cell/ml in growth medium (RPMI1640+10% FBS+2 mM L-glutamine+1% Pen-Strep) and incubated for 1 hours at 37° C. before dsRNA treatment. Cells were then treated with the test dsRNAs at different concentrations using the Lipofectamine™2000 reagent (Invitrogen) according manufacturer's instructions and incubated at 37° C. in a 5% $CO_2$ incubator for 24 hours.

As a positive control for interferon (IFN) response, cells were treated with either polyinosinic:polycytidylic acid (poly(I:C)), a synthetic analogue of double strand RNA (dsRNA) which is a TLR3 ligand (InvivoGen Cat#tlrl-pic) at final concentrations of 0.25-5.0 μg/mL or to Thiazolaquinolone (CL075), a TLR 7/8 ligand (InvivoGen Cat#tlrl-c75) at final concentrations of 0.075-2 μg/mL. Cell treated with Lipofectamine™2000 reagent were used as negative (reference) control for IFN response.

At about 24 hours following incubation, cells were collected and supernatant was transferred to new tubes. Samples were frozen immediately in liquid nitrogen and secretion of IL-6 and TNF-α cytokines was tested using IL-6, DuoSet ELISA kit (R&D System DY2060), and TNF-α, DuoSet ELISA kit (R&D System DY210), according to manufacturer's instructions. RNA was extracted from the cell pellets and mRNA levels of human genes IFIT1 (interferon-induced protein with tetratricopeptide repeats 1) and MX1 (myxovirus (influenza virus) resistance 1, interferon-inducible protein p78) were measured by qPCR. Measured mRNA quantities were normalized to the mRNA quantity of the reference gene peptidylprolyl isomerase A (cyclophilin A; CycloA). Induction of IFN-signaling was evaluated by comparing the quantity of mRNA from IFIT1 and MX1 genes from treated cells, relative to their quantities from non-treated cells. The qPCR results are those that passed QC standards, i.e. the value of the standard curve slope was in the interval [−4,−3], R2>0.99, no primer dimers. Results that did not pass the QC requirements were disqualified from analysis.

Figure 8A:
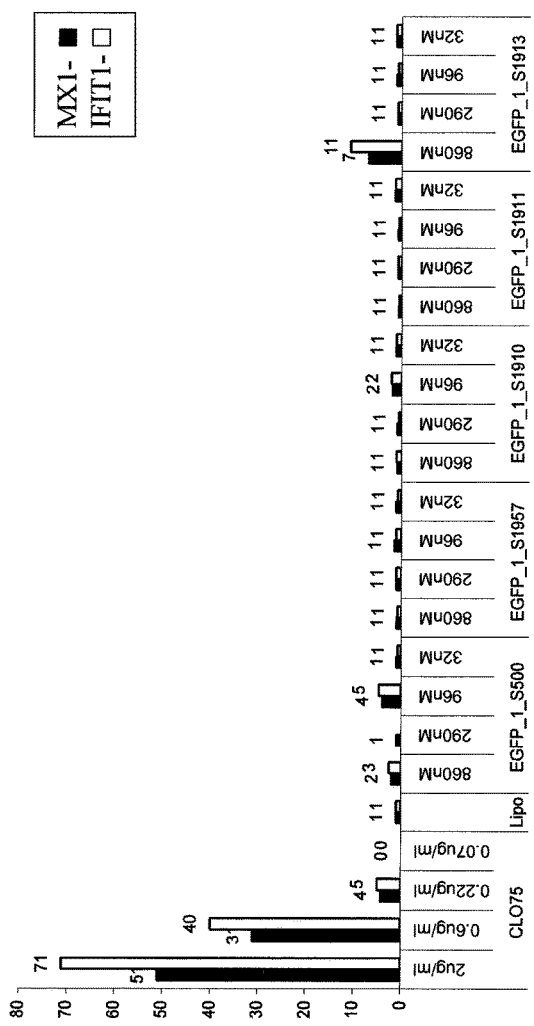
FIGS. 8A and 8B show levels of interferon responsive mRNA in response to exposure to dsRNA EGFP compounds EGFP_1_S500, EGFP_1_S1957, EGFP_1_S1910, EGFP__1__S1911 and EGFP__1_S1913 (described above for FIGS. 1A, 1B and 2A) in human plasma mononuclear cells (PMNC). White columns refer to levels of IFIT1, dark gray columns refer to levels of MX1, as described in Example 7, hereinbelow. Poly IC control values were: 1.7 ug: IFIT1-91, MX1-296; 0.56 ug: IFIT1-73, MX1-296; 0.19 ug: IFIT1-41, MX1-339.
Figure 8B:
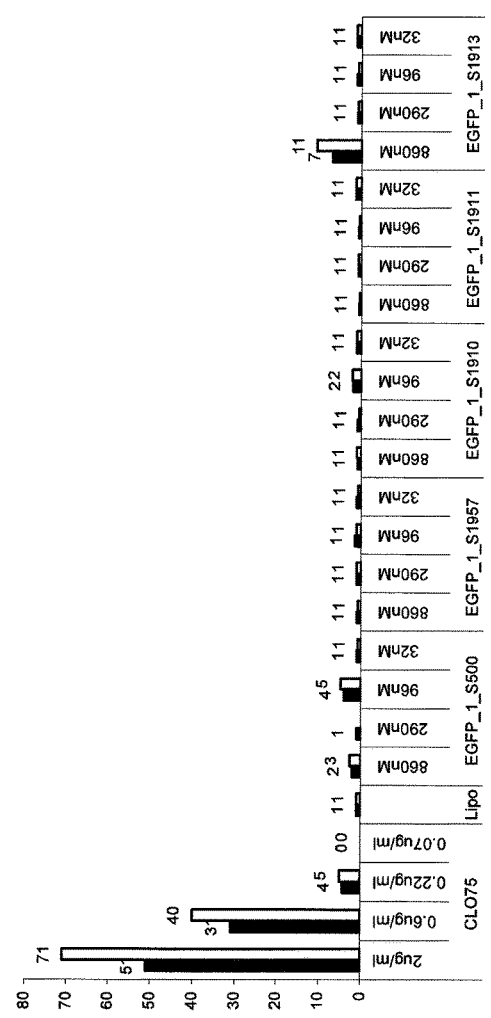
Figure 9:
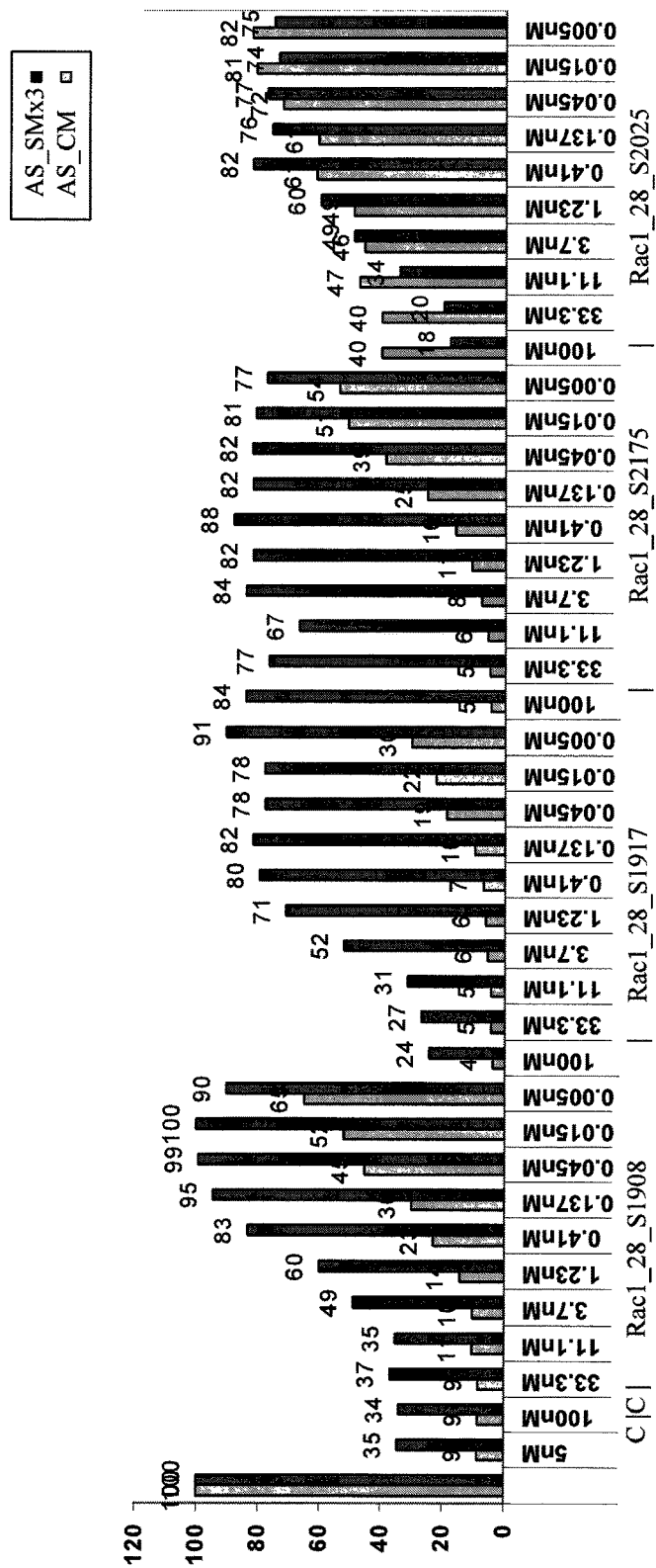
FIG. 9 shows reduced off target activity and increased on-target activity of dsRNA molecules targeting Rac1 with pyrazolotriazine RNA nucleotide analogue in the antisense strand (RAC1_28_S1917 and RAC1_28_S2001) as compared to dsRNA molecules targeting Rac1 without the PT nucleotide analogue (RAC1_28_S1908 and RAC1_28_S2025). RAC1_28_S1917, RAC1_28_S1908, RAC1_28_S2025, RAC1_28_S2001 shared the same sense strand with unmodified ribonucleotides in positions 2, 4, 6, 7, 8, 9, 11, 12, 14, 15, 17 and 19 (5'>3'), 2'-OMethyl sugar modified ribonucleotides in positions 1, 3, 5, 10, 13, 16 and 18 and a 3' terminal phosphate. The modifications of the antisense strands are provided in the description for FIGS. 5A and 7, hereinabove.
Figure 10:
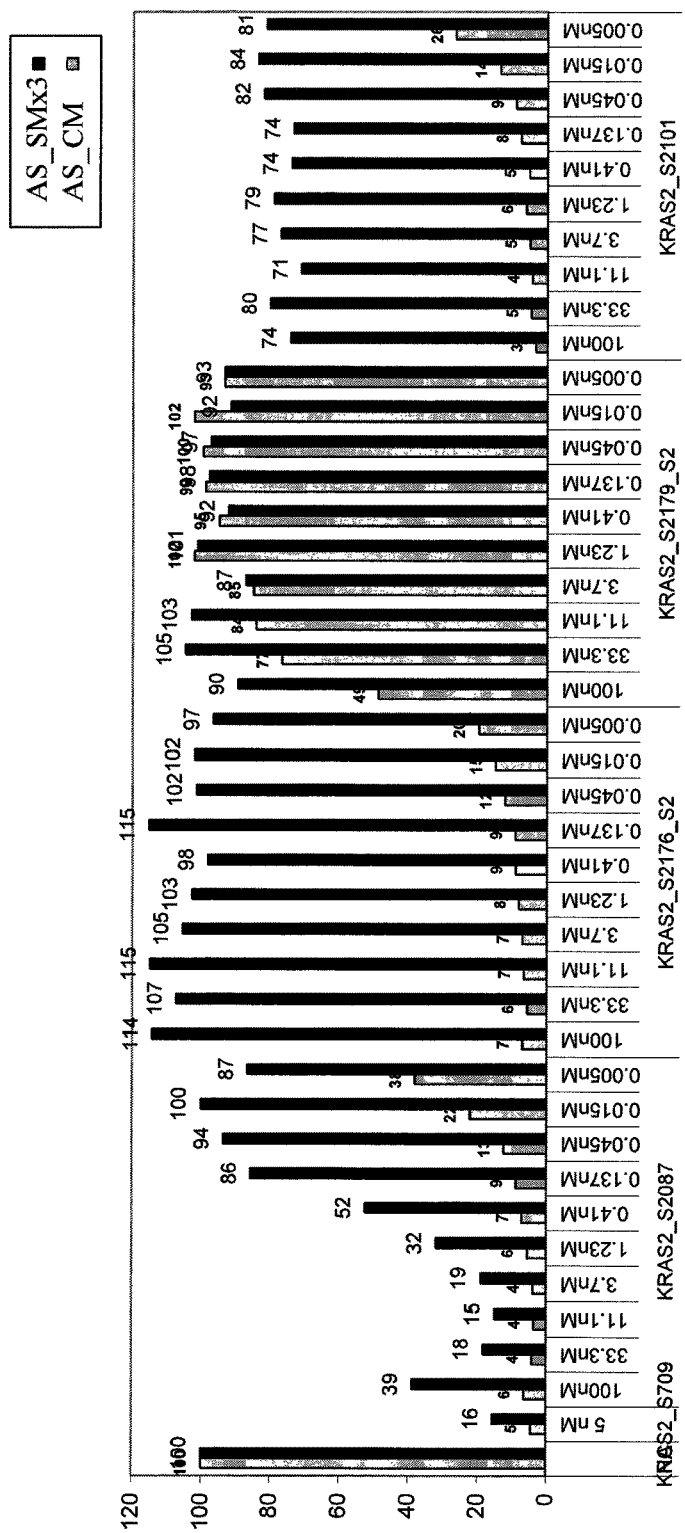
FIG. 10 shows reduced off-target activity and increased on-target activity of dsRNA molecules targeting KRAS with pyrazolotriazine RNA nucleotide analogue. KRAS_2_2101, KRAS_2_2087, KRAS__2__2176 and KRAS__2_2179 were tested. All the dsRNA share the same sense strand which included unmodified ribonucleotides in positions 1, 3, 4, 5, 6, 8, 9, 10, 11, 12, 14, 15, 17 and 19, 2'-OMethyl sugar modified ribonucleotides in positions 2, 7, 13, 16 and 18, and phosphate moiety at the 3' terminus KRAS_2_2101 and KRAS_2_2087 antisense strands included unmodified ribonucleotides in positions 2, 5, 7, 8, 9, 10, 11, 12, 13, 14, 16 and 18, 2'-OMethyl sugar modified ribonucleotides in positions 1, 6, 15, 17 and 19, and phosphate moiety at the 3' terminus KRAS_2_2101 antisense strand further included an unmodified ribonucleotide at position 3 and a pyrazolotriazine deoxyadenosine nucleotide analogue at position 4. KRAS_2_2087 antisense strand further included a 2'-OMethyl sugar modified ribonucleotide at position 3 and an unmodified riboadenosine at position 4. KRAS_2_2176 and KRAS_2_2179 antisense strands included unmodified ribonucleotides in positions 3, 5, 7, 8, 9, 10, 11, 12, 13, 14, 16 and 18, 2'-OMethyl sugar modified ribonucleotides in positions 1, 6, 15, 17 and 19, and phosphate moiety at the 3' terminus KRAS__2_2176 further included an unmodified ribonucleotide in position 2 and a pyrazolotriazine riboadenosine nucleotide analogue in position 4, while KRAS_2_2179 further included an unmodified ribonucleotide in position 4 and a pyrazolotriazine riboadenosine nucleotide analogue in position 2.

FIGS. 8A and 8B show that dsRNA molecules, which incorporate pyrazolotriazine nucleotide analogues described herein, do not induce interferon responsive genes MX1 or IFIT1.

Example 8. Duplex Melting Temperature (Tm)

All thermal denaturation studies were carried out using quartz cuvettes with an optical path length of 1 cm on a Cary 300 UV/vis spectrophotometer interfaced with a computer for data collection and analysis. Duplex siRNA with an O.D of 0.2-0.4 was placed in the cuvette and the same buffered solution was used as reference. The temperature was increased and decreased from 20° C. to 80° C. at the rate of 1° C./min. In general, Tm of the duplexes is reduced when a ribonucleotide is replaced with a pyrazolotriazine nucleotide analogue. Table G shows Tm of several control and test dsRNA molecules.

TABLE G

| Duplex name | Modification | Tm (° C.) |
|---|---|---|
| RAC1_28_S1908 | unmodified and 2'OMe and riboadenosine at position 5 in the AS | 75.2 |
| RAC1_28_S1917 | unmodified and 2'OMe and PT deoxyadenosine at position 5 in the AS | 66 |
| EGFP_1_S1911 | alternating unmodified and 2'OMe and PT deoxyadenosine at position 1 in the AS | 71 |
| EGFP_1_S1913 | alternating unmodified and 2'OMe and PT deoxyadenosine at position 18 of the SS | 71 |
| EGFP_1_S500 | alternating unmodified and 2'OMe (2'OMe at position 1 of the AS and position 18 of the SS) | 72 |

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

The invention claimed is:
1. An siRNA having the following general structure A1:

5'(N)x-Z3'(antisense strand)

3'Z'—(N')y-z"5'(sense strand)        (A1)

wherein each of N and N' is an unmodified ribonucleotide, a modified ribonucleotide, or an unconventional moiety, and at least one of N or N' comprises an adenine pyrazolotriazine (PT) nucleotide analogue of general formula IIa:

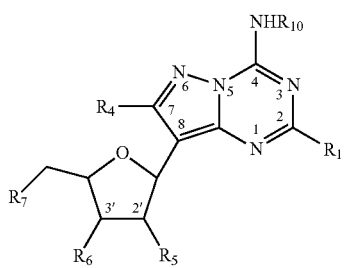

wherein
$R_1$ and $R_4$ each independently is selected from H, halogen, —CN, —SCN, —NO$_2$, —O— hydrocarbyl, —S-hydrocarbyl, —CO—H, —CO-hydrocarbyl, —NR$_8$R$_9$, heteroaryl, or hydrocarbyl optionally substituted by one or more groups each independently a halogen, —CN, —SCN, or —NO$_2$ wherein $R_8$ and $R_9$ each independently is H or hydrocarbyl, or $R_8$ and $R_9$ together with the nitrogen atom to which they are attached form a saturated or unsaturated heterocyclic ring optionally containing 1-2 further heteroatoms selected from oxygen, nitrogen or sulfur;
$R_{10}$ is H;
$R_5$ is H, halogen, —O$^-$ or —OR$_{11}$;
$R_6$ is —O$^-$ or —OR$_{11}$,
$R_7$ is OR$_{11}$, a monophosphate moiety or a phosphate linking moiety; and
$R_{11}$ each independently is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein R$_{12}$ and R$_{13}$ each independently is H or (C$_1$-C$_8$)alkyl;
wherein each of (N)x and (N')y is an oligonucleotide in which each consecutive N or N' is joined to the next N or N' by a covalent bond;
wherein each of Z and Z' is independently present or absent, but if present independently includes 1-5 consecutive nucleotides, PT nucleotide analogues or non-nucleotide moieties or a combination thereof, or a vitamin, or a drug moiety, covalently attached at the 3' terminus of the strand in which it is present;
wherein z" may be present or absent, but if present is a capping moiety covalently attached at the 5' terminus of (N')y;
wherein each of x and y is independently an integer between 15 and 40; and
wherein the sequence of (N')y is complementary to the sequence of (N)x and wherein at least a portion of the sequence of (N)x is complementary to a consecutive sequence in a target RNA;
or
a pharmaceutically acceptable salt thereof.

2. The siRNA of claim 1, wherein the sequence of (N')y is fully complementary to the sequence of (N)x.

3. The siRNA of claim 1, wherein the adenine PT nucleotide analogue comprises a PT deoxyadenosine analogue of formula IIa wherein each of $R_1$, $R_4$, and $R_5$ is H; $R_6$ is —O$^-$ or —OH; and $R_7$ is OH or a monophosphate moiety or a phosphate linking moiety.

4. The siRNA of claim 1, wherein the adenine PT nucleotide analogue comprises an adenosine PT nucleotide analogue of formula IIa wherein each of $R_1$ and $R_4$ is H; $R_5$ is —OR$_{11}$, wherein R$_{11}$ is H, (C$_1$-C$_8$)alkyl, (C$_1$-C$_8$)alkylene-OR$_{12}$, (C$_1$-C$_8$)alkylene-SR$_{12}$, or (C$_1$-C$_8$)alkylene-NR$_{12}$R$_{13}$, wherein R$_{12}$ and R$_{13}$ each is independently H or (C$_1$-C$_8$) alkyl; $R_6$ is —O$^-$ or —OH; and $R_7$ is OH or a monophosphate moiety or a phosphate linking moiety.

5. The siRNA of claim 1, wherein the 5' terminus of the sense or antisense strand comprises a PT nucleotide analogue of general formula IIa selected from the following compounds:
a compound wherein $R_{10}$ is H, $R_1$ is H, $R_4$ is H, $R_5$ is H, $R_6$ is —O$^-$, $R_7$ is —OH (compound 3),
a compound wherein $R_{10}$ is H, $R_1$ is H, $R_4$ is H, $R_5$ is H, $R_6$ is —O$^-$, $R_7$ is —OP(=O)—OO$^{2-}$ (compound 7),
a compound wherein $R_{10}$ is H, $R_1$ is H, $R_4$ is H, $R_5$ is —OH, $R_6$ is —O$^-$, $R_7$ is —OH (Compound 9),
a compound wherein $R_{10}$ is H, $R_1$ is H, $R_4$ is H, $R_5$ is —OH, $R_6$ is —O$^-$, $R_7$ is —OP(=O)—OO$^{2-}$ (compound 13),
a compound wherein $R_{10}$ is H, $R_1$ is H, $R_4$ is H, $R_5$ is —OCH$_3$, $R_6$ is —O$^-$, $R_7$ is —OH (compound 15),
a compound wherein $R_{10}$ is H, $R_1$ is H, $R_4$ is H, $R_5$ is —OCH$_3$, $R_6$ is —O$^-$, $R_7$ is —OP(=O)—OO$^{2-}$ (compound 19),
a compound wherein $R_{10}$ is H, $R_1$ is H, $R_4$ is H, $R_5$ is O(CH$_2$)$_2$—OCH$_3$, $R_6$ is —O$^-$, $R_7$ is —OH (compound 21),
a compound wherein $R_{10}$ is H, $R_1$ is H, $R_4$ is H, $R_5$ is O(CH$_2$)$_2$—OCH$_3$, $R_6$ is —O$^-$, $R_7$ is —OP(=O)—OO$^{2-}$ (compound 25),
a compound wherein $R_{10}$ is H, $R_1$ is H, $R_4$ is H, $R_5$ is F, $R_6$ is —O$^-$, $R_7$ is —OH (compound 27), and
a compound wherein $R_{10}$ is H, $R_1$ is H, $R_4$ is H, $R_5$ is F, $R_6$ is —O$^-$, $R_7$ is —OP(=O)—OO$^{2-}$ (compound 31).

6. The siRNA of claim 1, wherein the 3' terminus of the antisense strand and/or the sense strand comprises a PT nucleotide analogue of general formula IIa selected from the following compounds:
a compound wherein $R_{10}$ is H, $R_1$ is H, $R_4$ is H, $R_5$ is H, $R_6$ is —OH, $R_7$ is —OP(=O)—OO$^{2-}$ (compound 5),
a compound wherein $R_{10}$ is H, $R_1$ is H, $R_4$ is H, $R_5$ is —OH, $R_6$ is —OH, $R_7$ is —OP(=O)—OO$^{2-}$ (compound 11),
a compound wherein $R_{10}$ is H, $R_1$ is H, $R_4$ is H, $R_5$ is —OCH$_3$, $R_6$ is —OH, $R_7$ is —OP(=O)—OO$^{2-}$ (compound 17),
a compound wherein $R_{10}$ is H, $R_1$ is H, $R_4$ is H, $R_5$ is O(CH$_2$)$_2$—OCH$_3$, $R_6$ is —OH, $R_7$ is —OP(=O)—OO$^{2-}$ (compound 23), and
a compound wherein $R_{10}$ is H, $R_1$ is H, $R_4$ is H, $R_5$ is F, $R_6$ is —OH, $R_7$ is —OP(=O)—OO$^{2-}$ (compound 29).

7. The siRNA of claim 1, wherein the sense strand and/or the antisense strand comprises a PT nucleotide analogue of general formula IIa selected from the following compounds in an internal position:
a compound wherein $R_{10}$ is H, $R_1$ is H, $R_4$ is H, $R_5$ is H, $R_6$ is —O$^-$, $R_7$ is —OP(=O)—OO$^{2-}$ (compound 7), a compound wherein $R_{10}$ is H, $R_1$ is H, $R_4$ is H, $R_5$ is —OH, $R_6$ is —O⁻, $R_7$ is —OP(=O)—OO²⁻ (compound 13), a compound wherein $R_{10}$ is H, $R_1$ is H, $R_4$ is H, $R_5$ is —OCH₃, $R_6$ is —O⁻, $R_7$ is —OP(=O)—OO²⁻ (compound 19), a compound wherein $R_{10}$ is H, $R_1$ is H, $R_4$ is H, $R_5$ is O(CH₂)₂—OCH₃, $R_6$ is —O⁻, $R_7$ is —OP(=O)—OO²⁻ (compound 25), and a compound wherein $R_{10}$ is H, $R_1$ is H, $R_4$ is H, $R_5$ is F, $R_6$ is —O⁻, $R_7$ is —OP(=O)—OO²⁻ (compound 31).

8. The siRNA of claim 1, wherein the PT nucleotide analogue is present in at least one of (5'>3') position 1, position 3, position 4 and position 5 in the antisense strand.

9. The siRNA of claim 1 for use in down regulating mammalian target gene expression or non-mammalian target gene expression.

10. A composition comprising the siRNA of claim 1; and a carrier.

11. The siRNA of claim 8, wherein the PT nucleotide analogue is present at (5'>3') position 1 in the antisense strand.

12. The siRNA of claim 8, wherein the PT nucleotide analogue is present at (5'>3') position 5 in the antisense strand.

\* \* \* \* \*